United States Patent
Barnes et al.

(10) Patent No.: US 11,364,102 B2
(45) Date of Patent: Jun. 21, 2022

(54) SHORT WAVELENGTH VISIBLE LIGHT-EMITTING TOOTHBRUSH WITH AN ELECTRONIC SIGNAL INTERLOCK CONTROL

(71) Applicant: OraLucent, LLC, Long Beach, CA (US)

(72) Inventors: Mike Barnes, Dunellon, FL (US); Timothy Lawrence, Long Beach, CA (US); Greg Shepherd, Fruitland Park, FL (US)

(73) Assignee: Oralucent, Inc., Long Beach, FL (US)

( * ) Notice: Subject to any disclaimer, the term of this patent is extended or adjusted under 35 U.S.C. 154(b) by 235 days.

(21) Appl. No.: 16/076,687

(22) PCT Filed: Feb. 7, 2017

(86) PCT No.: PCT/US2017/016805
§ 371 (c)(1),
(2) Date: Aug. 8, 2018

(87) PCT Pub. No.: WO2017/139256
PCT Pub. Date: Aug. 17, 2017

(65) Prior Publication Data
US 2019/0167400 A1 Jun. 6, 2019

Related U.S. Application Data

(60) Provisional application No. 62/435,168, filed on Dec. 16, 2016, provisional application No. 62/343,471, (Continued)

(51) Int. Cl.
*A61C 17/22* (2006.01)
*A46B 15/00* (2006.01)
(Continued)

(52) U.S. Cl.
CPC ........ *A61C 17/227* (2013.01); *A46B 15/0012* (2013.01); *A46B 15/0034* (2013.01);
(Continued)

(58) Field of Classification Search
CPC . A61C 17/227; A61C 17/221; A61C 17/3481; A46B 15/0012; A46B 15/0034;
(Continued)

(56) References Cited

U.S. PATENT DOCUMENTS

| | | | |
|---|---|---|---|
| 5,653,591 A | 8/1997 | Loge | 433/118 |
| 5,894,620 A | 4/1999 | Polaert et al. | 15/22.1 |

(Continued)

FOREIGN PATENT DOCUMENTS

| | | | |
|---|---|---|---|
| CN | 202841617 U | 3/2013 | |
| EP | 2 550 935 A1 | 1/2013 | A61C 17/22 |

(Continued)

OTHER PUBLICATIONS

Sliney, David H., Biohazarads of Ultraviolet, Visible and Infrared Radiation, J. O Occupational and Environmental Medicine, 1983, vol. 25, Issue 3, Abstract only.

(Continued)

*Primary Examiner* — Paula J Stice
(74) *Attorney, Agent, or Firm* — MacCord Mason PLLC

(57) ABSTRACT

A toothbrush having one or more light sources with an electronic interlock control device preventing operation of the light source when the toothbrush is removed from the user's mouth. The electronic interlock control over operation is necessary to prevent accidental eye exposure to the high intensity light source with a wavelength in the range of about 400 nm to about 1000 nm. The light-emitting toothbrush activates upon entering the user's mouth but deacti-
(Continued)

vates immediately when removed, thus protecting the user's eyes from direct exposure to the high power light source contained in the brush head.

28 Claims, 51 Drawing Sheets

Related U.S. Application Data filed on May 31, 2016, provisional application No. 62/331,665, filed on May 4, 2016, provisional application No. 62/606,150, filed on Feb. 8, 2016.

(51) Int. Cl.
  *A61N 5/06* (2006.01)
  *A61C 19/06* (2006.01)
  *A61C 17/34* (2006.01)

(52) U.S. Cl.
  CPC ........ *A46B 15/0036* (2013.01); *A61C 17/221* (2013.01); *A61C 17/3481* (2013.01); *A61C 19/066* (2013.01); *A61N 5/0603* (2013.01); *A61N 5/0624* (2013.01); *A61N 2005/0606* (2013.01); *A61N 2005/0644* (2013.01); *A61N 2005/0651* (2013.01); *A61N 2005/0659* (2013.01); *A61N 2005/0662* (2013.01)

(58) Field of Classification Search
  CPC ............ A46B 15/0036; A61N 15/0603; A61N 15/0624; A61N 2005/0606; A61N 2005/0659; A61N 2005/0662
  See application file for complete search history.

(56) References Cited

U.S. PATENT DOCUMENTS

| | | | | |
|---|---|---|---|---|
| 6,081,957 | A | 7/2000 | Webb | 15/105 |
| 6,149,895 | A | 11/2000 | Kutsch | 424/53 |
| 6,536,068 | B1 | 3/2003 | Yang et al. | |
| 6,623,272 | B2 | 9/2003 | Clemans | 433/215 |
| 6,752,627 | B2 | 6/2004 | Lin | 433/29 |
| 6,883,199 | B1* | 4/2005 | Lundell | A61C 17/221 15/22.1 |
| 6,902,397 | B2 | 6/2005 | Farrell et al. | 433/29 |
| 7,467,946 | B2 | 12/2008 | Rizoiu et al. | 433/29 |
| 8,021,148 | B2 | 9/2011 | Goodson et al. | 433/29 |
| 2003/0232303 | A1 | 12/2003 | Black | 433/29 |
| 2004/0019990 | A1 | 2/2004 | Farrell et al. | 15/105 |
| 2004/0193236 | A1 | 9/2004 | Altshuler et al. | 607/88 |
| 2005/0064371 | A1 | 3/2005 | Soukos et al. | 433/29 |
| 2005/0172429 | A1 | 8/2005 | Russell et al. | 15/22.1 |
| 2005/0175956 | A1 | 8/2005 | Russell et al. | 15/22.1 |
| 2007/0182517 | A1 | 8/2007 | Kennish et al. | |
| 2007/0270221 | A1 | 11/2007 | Park et al. | |
| 2008/0032253 | A1 | 2/2008 | Montgomery et al. | 433/29 |
| 2008/0131834 | A1 | 6/2008 | Shepherd et al. | 433/29 |
| 2008/0183249 | A1 | 7/2008 | Kitagawa et al. | 607/79 |
| 2008/0026393 | A1 | 11/2008 | Russell et al. | 15/105 |
| 2009/0083924 | A1* | 4/2009 | Shepherd | A46B 15/0034 15/105 |
| 2010/0178252 | A1 | 7/2010 | Sagel et al. | 424/9.6 |
| 2010/0239998 | A1 | 9/2010 | Snyder et al. | 433/29 |
| 2011/0296643 | A1 | 12/2011 | Shepherd et al. | 15/167.1 |
| 2013/0025078 | A1 | 1/2013 | Heil et al. | 15/22.1 |
| 2013/0066404 | A1* | 3/2013 | Tapper | A61F 9/045 607/90 |
| 2015/0192259 | A1* | 7/2015 | Patel | F21L 15/14 362/231 |
| 2016/0220013 | A1 | 8/2016 | Barnes et al. | 15/34 |

FOREIGN PATENT DOCUMENTS

| | | | | |
|---|---|---|---|---|
| GB | 2 030 855 | | 9/1978 | ............ A46B 13/02 |
| JP | 08275961 | | 10/1996 | ............ A61C 17/22 |
| JP | 2000175745 | | 6/2000 | |
| WO | WO 2006/098719 | A1 | 9/2006 | ............ A61B 5/00 |
| WO | WO 2007/093860 | A1 | 8/2007 | ............ A61C 15/04 |
| WO | WO 2009141489 | | 11/2009 | |
| WO | WO 2015/084962 | A1 | 6/2015 | ............ A46B 15/00 |
| WO | WO 2017/137256 | | 8/2017 | ........................ 17/22 |

OTHER PUBLICATIONS

Luk, et al., "Effect of light energy on peroxide tooth bleaching," J.Am Dent Assoc, 2004; 135(2):194-201.

Dulori, et al., "Maximum permissible exposures for ocular safety (ANSI 2000), with emphasis on ophthalmic devices," J. Opt. Soc. Am A Opt Image Sci Vis, 2007 24(5), 1250-65.

Steinburg, et al., Genetic and physiological effcts of noncoherent visible light combined with hydrogen peroxide on *Streptococcus mutans* in biofilm,: Antimicrob Agents Chemothr, Jul. 2008, 52(7).

Maclean, et al., "Inactivation of Bacterial Pathogens following Exposure to Light from a 405-Nanometer Light-Emitting Diode Array," Appl Environ Microbiol. 2009, 75(7).

FDI policy statement on detal bleaching materials Adopted by the FDI General Assembly: Sep. 17, 2011—Mexico City, Mexico, Intl. Dental J. 2013, 63, 2-3.

Buchalla, et al., External bleaching therapy with activation by heat, light or laser—a systematic review; May 2007; 23(5); 586-96. Epub Jul. 3, 2006.

Search Report of Counterpart EPO application 17750623.5.

Philips Sonicare FlexCare Platinum Connected Brochure 2016 Koninklijke Philips N.V www.philips.com Healthcare, LLC.

Office Action from the China National Intellectual Property Administration dated Nov. 6, 2020 for Chinese Patent Application No. 201780010489.2, with English translation.

* cited by examiner

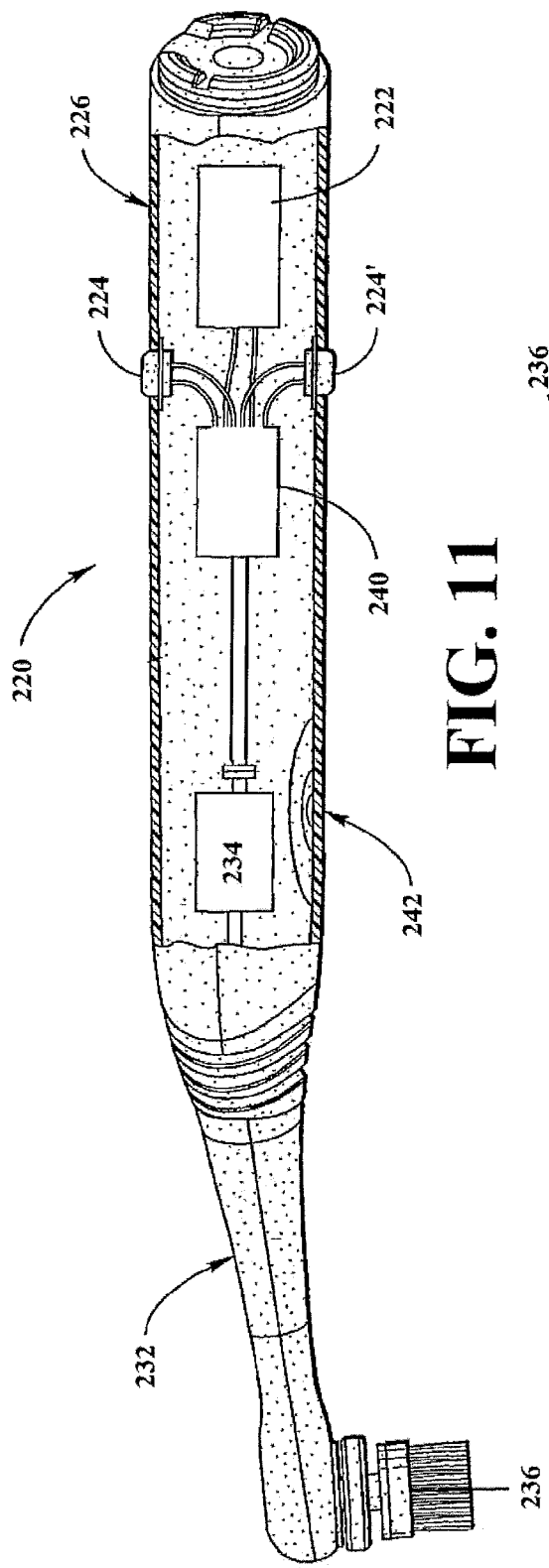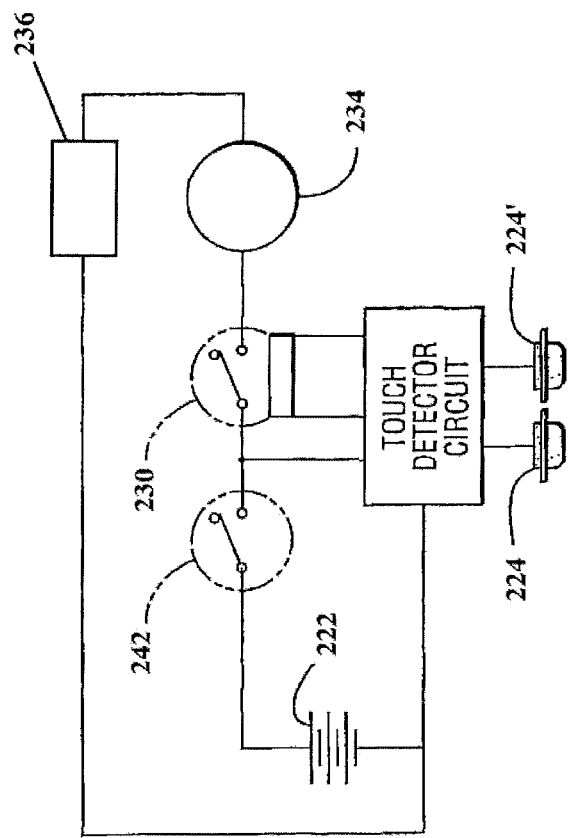
FIG. 11
FIG. 12

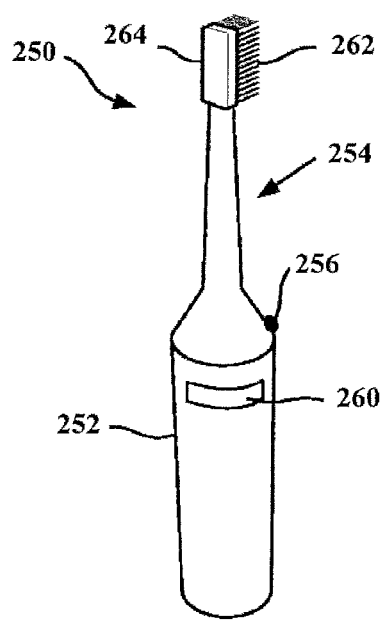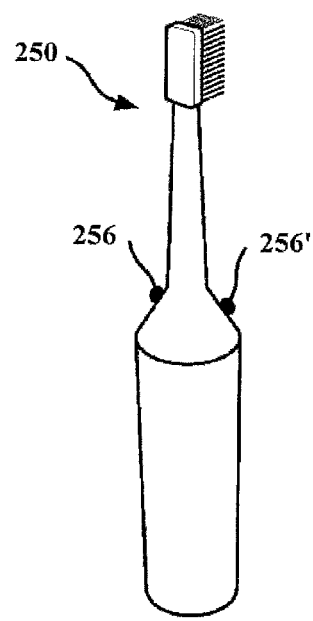
FIG. 14  FIG. 15

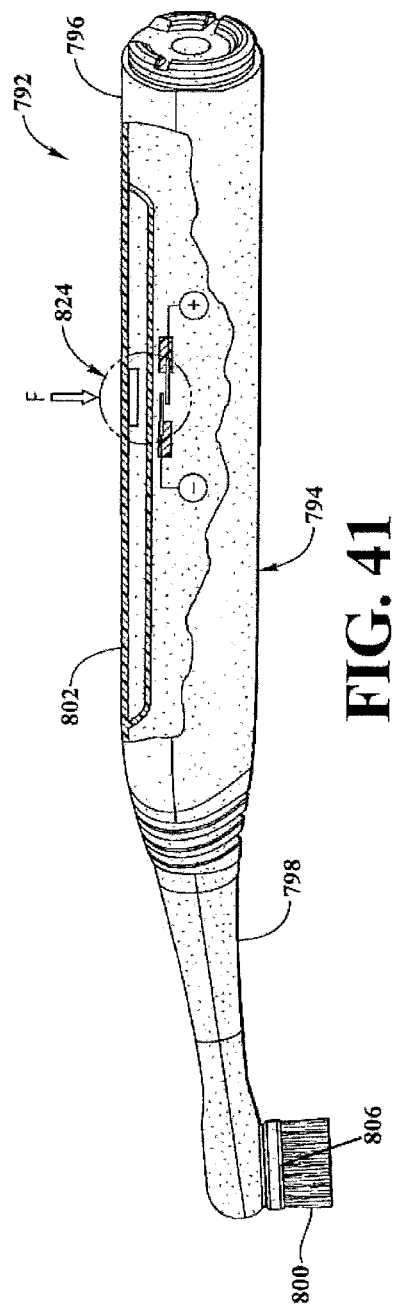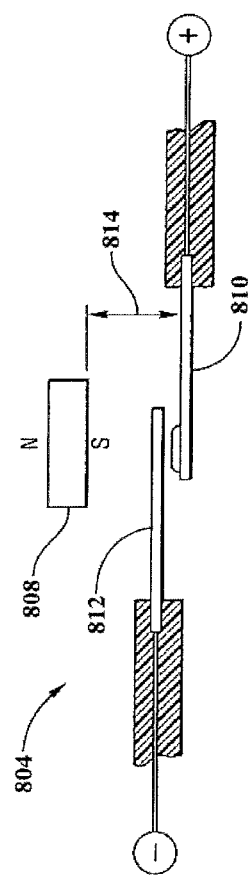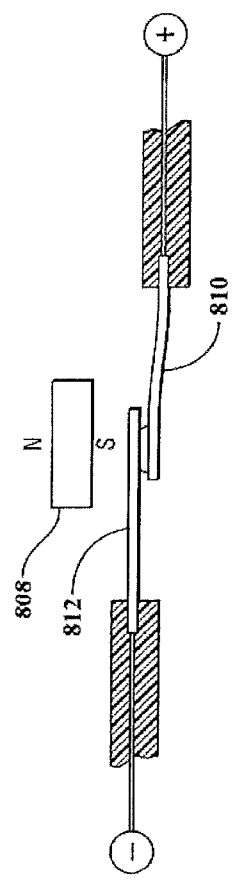
FIG. 41
FIG. 42
FIG. 43

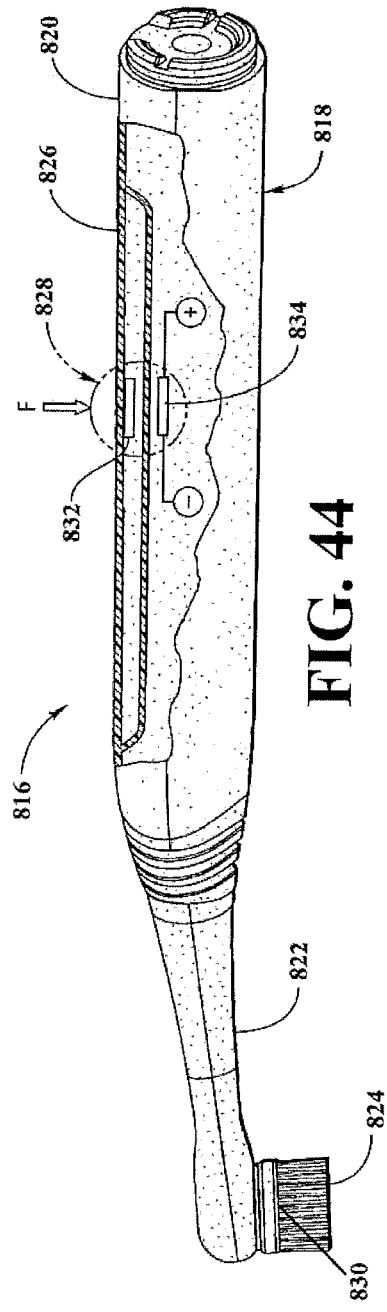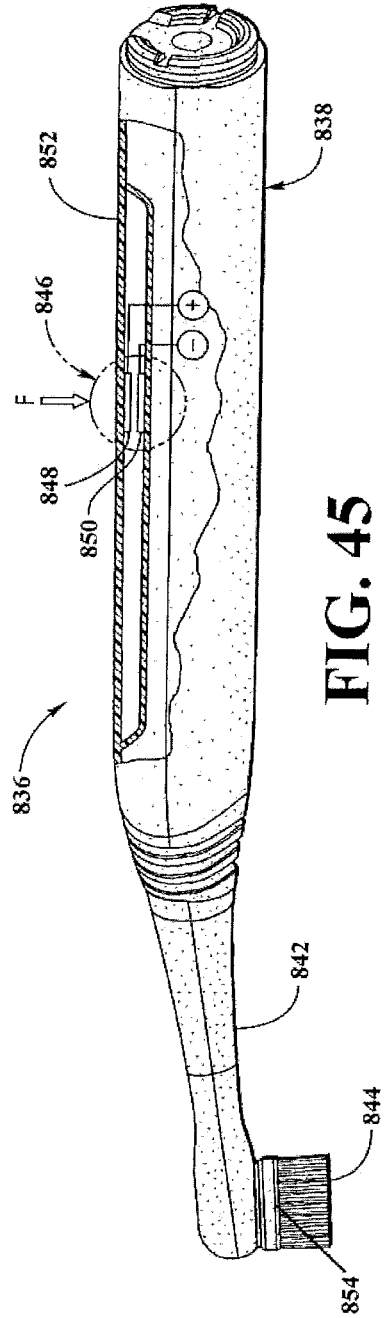

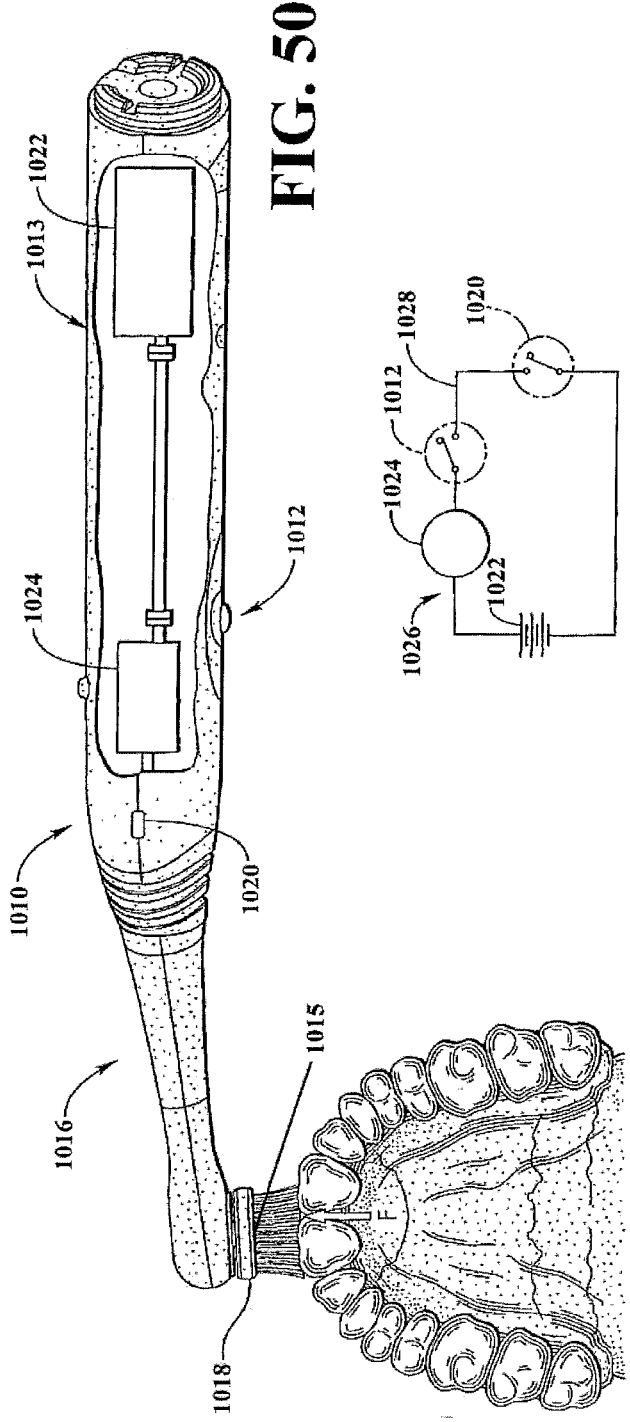

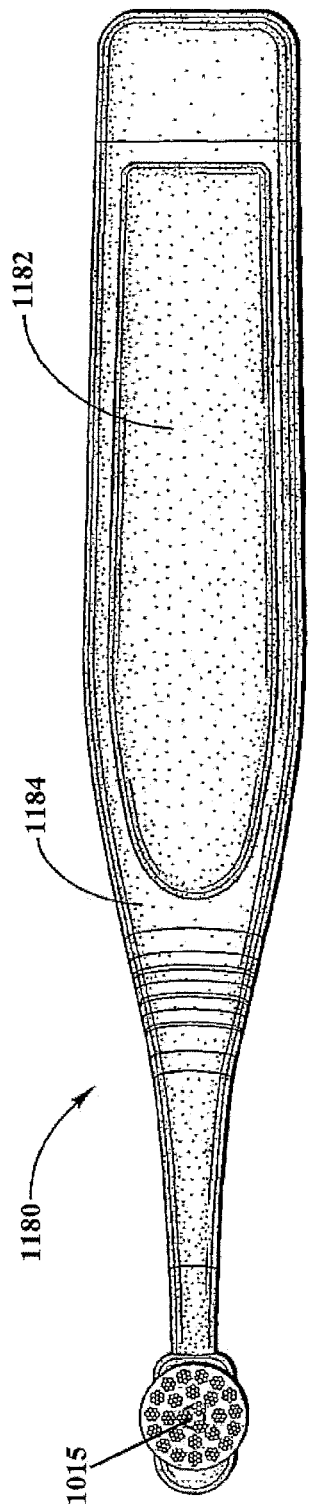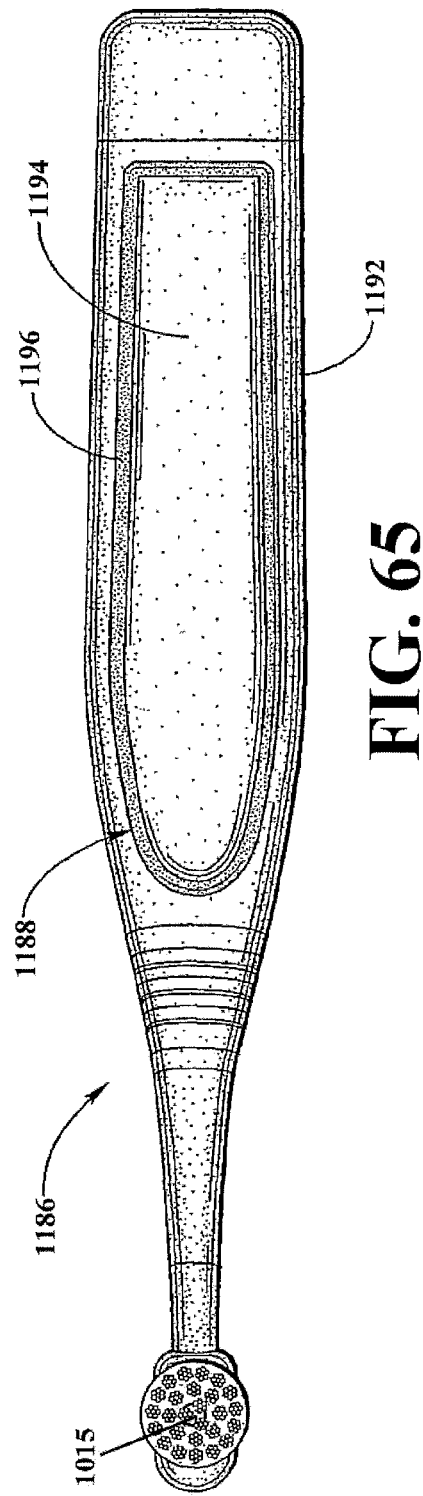
FIG. 64
FIG. 65

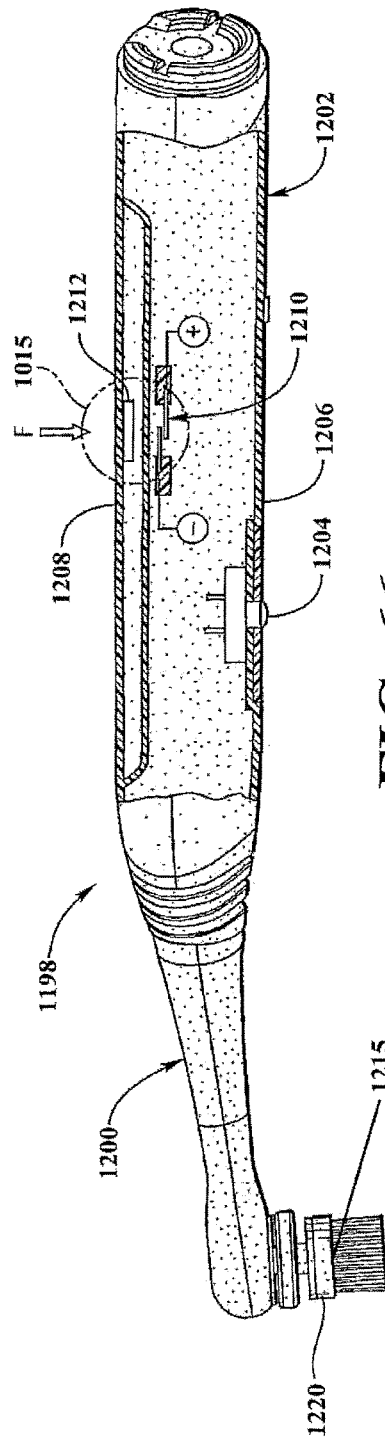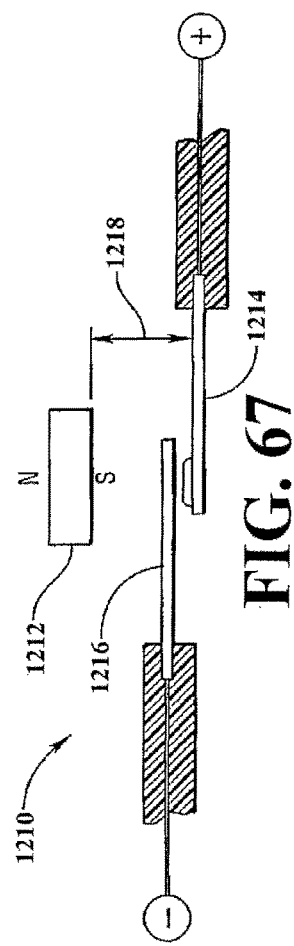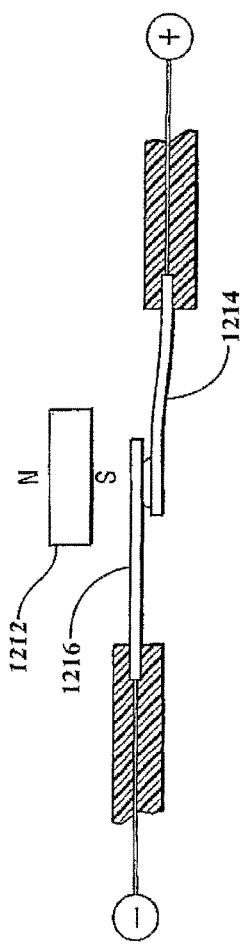
FIG. 66
FIG. 67
FIG. 68

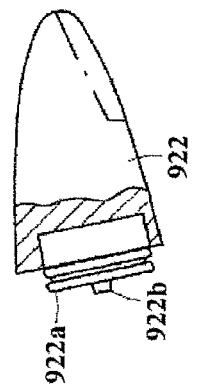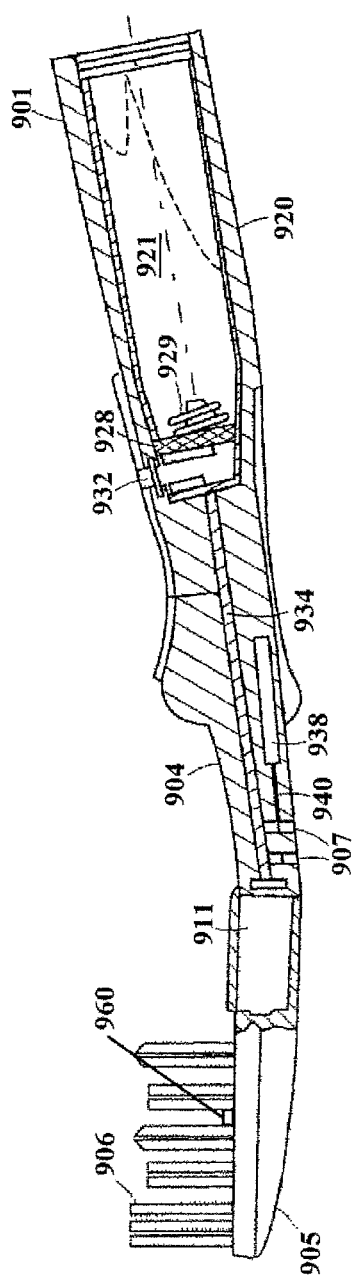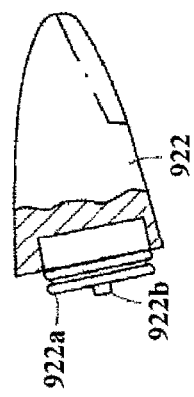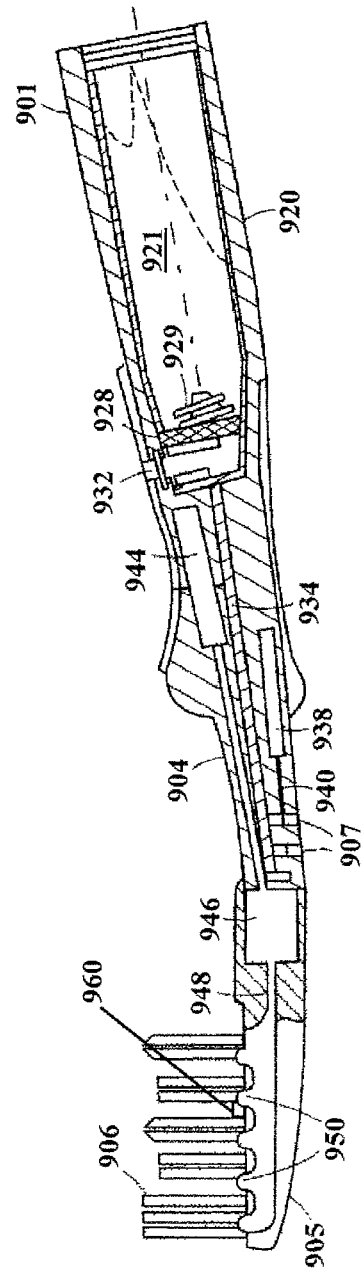
FIG. 70
FIG. 71

| Type of Sensor | Trigger Event | State Transition Event |
| --- | --- | --- |
| Current Loop | Circuit closed | Closed |
| | Circuit open | Open |
| Capacitive Sensor | Capacitance threshold exceeded | Closed |
| | Below capacitance threshold | Open |
| Inductive Sensor | Inductance threshold exceeded | Closed |
| | Below inductance threshold | Open |
| Passive Thermal Infrared Sensor | Body temperature infrared detected above threshold | Closed |
| | Body temperature infrared detected below threshold | Open |
| Active Thermal Infrared Sensor | Reflected infrared from IR emitter detected above threshold | Closed |
| | Reflected infrared from IR emitter detected below threshold | Open |
| Passive Photo Sensor | Dark, ambient light below threshold | Closed |
| | Dark, ambient light above threshold | Open |
| Active Photo Sensor | Reflected light from emitter detected above threshold | Closed |
| | Reflected light from emitter detected below threshold | Open |
| Pressure Sensor | Pressure threshold exceeded | Closed |
| | Below pressure threshold | Open |
| Cantilever switch sensor | Switch closed | Closed |
| | Switch open | Open |
| Moisture sensor | Moisture threshold exceeded | Closed |
| | Below moisture threshold | Open |

FIG. 78

Example 1: Output diameter = 2.3 x Input Diameter

Example 2: Output diameter = 4.4 x Input Diameter

| Input Diameter | 1 | 1 |
|---|---|---|
| Output Diameter | 2.3 | 4.4 |
| Length | 3.3 | 11.4 |
| Half Cone Angle | 41.3 | 20 |
| NA (sinθ) | 0.66 | 0.34 |

SHORT WAVELENGTH VISIBLE LIGHT-EMITTING TOOTHBRUSH WITH AN ELECTRONIC SIGNAL INTERLOCK CONTROL

BACKGROUND OF THE INVENTION

The present invention relates to increasing the safety of a dental hygiene implement such as a light-emitting manual or an electrically operated motorized toothbrush which emits radiation in the violet and/or blue region of the visible spectrum, between 400 nm and 500 nm (referred to herein as "visible therapeutic light"), in order to:

- oxidize and destroy potentially harmful bacteria and/or other contaminants or compounds contained within the mouth without harming or destroying human cells;
- exert a phototoxic effect on pathogenic periodontal and oral bacteria such as; *P. gingivalis* and *F. nucleatum*, and *S. mutans;*
- activate a photo catalyst that may be deposited on the teeth and the gums of the person utilizing the toothbrush during normal brushing; and/or
- accelerate the whitening effects of a tooth bleaching agent added to toothpaste or toothgel such as carbamide peroxide or hydrogen peroxide.

The electronic interlock control mechanism in this toothbrush will reduce the possibility of accidental direct eye exposure to high flux visible light radiation emitted from this toothbrush when it is removed from the mouth.

Light-emitting toothbrushes have been developed over the past several years for teeth whitening applications in addition to the known oral hygiene benefits of regular brushing. When combined with a teeth whitening agent such as carbamide peroxide or hydrogen peroxide, studies have shown that light in the 400-500 nm range accelerates the whitening effect of these agents. Wolfgang Buchallaa, Thomas Attina: *External bleaching therapy with activation by heat, light or laser—A systematic review*; Karen Luk, D.D.S.; Laura Tam, D.D.S., M.Sc.; Manfred Hubert, Ph.D.: *Effect of light energy on peroxide tooth bleaching*.

In addition, violet light in the 400 nm-420 nm range has been shown to have a phototoxic effect on pathogenic oral bacteria such as *P. gingivalis, S. mutans* and others. Michelle Maclean, Scott J. MacGregor, John G. Anderson, and Gerry Woolsey: *Inactivation of Bacterial Pathogens following Exposure to Light from a 405-Nanometer Light-Emitting Diode Array*. Doron Steinberg, Daniel Moreinos, John Featherstone, Moshe Shemesh, and Osnat Feuerstein: *Genetic and Physiological Effects of Noncoherent Visible Light Combined with Hydrogen Peroxide on Streptococcus mutans in Biofilm*. The inventors have previously shown the use of a light-emitting diode (LED) within a toothbrush provides anti-microbial properties of benefit to the oral hygiene of the end-user.

Other studies have shown that red and infrared light in the range of 600 nm-1000 nm ("infrared therapeutic light") provides various oral health benefits and can be useful for treating sensitive teeth, tooth and bone damage, reduction of tooth decay causing bacteria, oral thrush/candidiasis, gum inflammation and oral wounds in soft tissue, ulcers, cold sores, tonsillitis, and other viral/bacterial infections. However, the application of light in this range is generally performed in a controlled laboratory environment or under the supervision of an oral care professional and involves the use of expensive equipment requiring specialized handling to avoid over-exposure, burns or eye-damage.

Current light-emitting toothbrushes have a manual on/off switch which activates the light-emitting device. This manual activation mechanism may lead to a safety risk because the user may activate the light and expose his or her eyes to high levels of light that may be harmful to the retina or optic nerve. The potentially harmful properties of visible light and maximum exposure levels are documented in ANSI standards. François C. Delori, Robert H. Webb, David H. Sliney: *Maximum permissible exposures for ocular safety (ANSI 2000), with emphasis on ophthalmic devices*. David H. Sliney, M. S.: *Biohazards of Ultraviolet, Visible and Infrared Radiation*. For example, the maximum permissible radiant power (thermal and photo-acoustic) entering a dilated pupil is $1.5 \times 10^{-4}$ Watts. This limit would be exceeded if a user were to stare at a 420 nm LED of 250 mW radiant flux at a distance of 10 cm for a period of 0.5 seconds. To prevent accidental eye exposure, a special electronic interlock control mechanism has been implemented to keep the optical source turned off if the toothbrush is not inserted in the user's mouth. The control mechanism will turn the optical source off immediately if the toothbrush is removed from the mouth prior to completing the brushing cycle.

A toothbrush is typically used in close proximity to the eyes of the user, and if ocular exposure to the light lasts several seconds, eye damage may occur. Furthermore, the ocular safety risk of manually activated light precludes the use of more powerful light-emitting devices such as high-powered LEDs, laser diodes, or vertical cavity surface emitting lasers, which would increase the teeth-whitening and antimicrobial benefits in proportion to the energy delivered. For example, studies show that effective whitening treatments require a minimum energy density of 30-50 J $cm^{-2}$ to produce noticeable shade whitening. However, such energy levels would not be readily achievable with a typical two minute brushing interval using a low-powered LED that would also be safe when directly placed in front of the eyes, even when used over a period of several weeks. Similar limitations exist for the anti-microbial properties of violet light as well.

It is therefore desirable to control the "on" state of the light-emitting device to a time period when it is in use in the oral cavity but to shut "off" this high power light source immediately, when it is removed from the mouth to prevent direct eye exposure. This feature would also extend battery life of a battery operated brush since power is only used to illuminate the light source when in direct contact with the oral cavity.

Ionic toothbrushes operate on the principal of electrostatic attraction. The theory holds that positively charged bacteria as well as acidic compounds with an H+ ion adhere to the surface of negatively charged teeth. By introducing a negatively charged anode in the brush head and a positively charge cathode in the brush handle, the polarity is reversed allowing positively charged bacteria to be attracted to the brush head so that plaque can be more easily dislodged during brushing. Some clinical studies of such ionic therapies have demonstrated beneficial results using an ionic toothbrush.

Another challenge that people face is establishing a proper brushing routine, including brushing their teeth consistently, correctly and for a sufficient time, which is why many commercial toothbrushes incorporate brush timers which alert the end user (for example, every 30 seconds) to ensure each quadrant is brushed thoroughly. Furthermore, if an adult suffers from periodontal disease and the dentist has recommended visible therapeutic light therapy to treat this disease, it would be useful for a dentist or treating physician to monitor this activity to ensure the patient is conducting the prescribed visible therapeutic light therapy during their twice daily brushing regimen.

Thus, Applicants desire a mechanism for a safe in-home consumer device that protects the end user from these risks and allows a physician and the end user to monitor brushing behavior and progress of a prescribed therapy.

SUMMARY OF THE INVENTION

This invention relates to increasing the safety of a dental hygiene implement that emits visible therapeutic light, i.e. radiation in the violet and/or blue region of the visible spectrum, between 400 nm and 500 nm, by determining whether the implement is within the user's mouth or outside of the user's mouth. Direct eye exposure to such light can be avoided using a sensor or combination of sensors that deactivate the light source whenever it is outside the environment of the mouth and permits activation only when inside the mouth of the user.

In one embodiment, the dental hygiene implement may be a light emitting toothbrush. The light emitting toothbrush, according to the present invention, will typically further include a control circuitry which will typically be located in the handle and normally include functions such as a timer circuitry (which times the duration(s) of use of the toothbrush while brushing), an on/off duty cycle of the visible therapeutic light source or sources, a battery replacement indicator, and so on.

Preferably the driver for driving the visible therapeutic light source is equipped with constant electrical current control electronics and a suitable driver is supplied by Linear Technology, of San Jose Calif., as part no. LTC3454 which is an integrated circuit high current LED driver. The control circuitry may also include visible therapeutic light source control circuitry, which may be connected with one or more sensors located in the brush head, for detecting when the brush head is actually located within a user's mouth, thereby reducing the possibility of the visible therapeutic light being inadvertently emitted except when the toothbrush is actually located within the mouth of the user. In another embodiment, the control circuitry may alternatively include one more sensors located on the handle to determine whether the brush head is actually located within a user's mouth.

In one embodiment, an AC or DC signal loop sensor establishes a signal loop through the user's mouth to the user's hand grasping the handle of the toothbrush to verify if the toothbrush head is within the user's mouth. If the sensor establishes a signal loop, the light source remains on until the toothbrush head is removed from the user's mouth breaking the signal loop. Once the signal loop is broken, the light source may be extinguished as soon as the brush head is removed from the mouth.

In another embodiment, the dental hygiene implement uses a capacitive sensor to determine whether the implement is within the user's mouth or outside of the user's mouth. The capacitive sensor may use a current loop which detects current flowing through the body of the end user when the brush head or bristles are in contact with the mouth and the handle is in contact with the hand.

In another embodiment, the dental hygiene implement uses a capacitive displacement sensor to determine whether the implement is within the user's mouth or outside of the user's mouth. The capacitive displacement sensor can detect change of position of any conductive target such as the human body.

In another embodiment, the dental hygiene implement uses an inductive sensor to determine whether the implement is within the user's mouth or outside of the user's mouth. The inductive sensor uses an inductance loop to measure the proximity of conductors such as the human body.

In another embodiment, the dental hygiene implement uses a passive thermal infrared sensor to determine whether the implement is within the user's mouth or outside of the user's mouth. The passive thermal infrared sensor detects the warmth of the human mouth to determine whether the implement is within the user's mouth.

In another embodiment, the dental hygiene implement uses an active thermal infrared sensor to determine whether the implement is within the user's mouth or outside of the user's mouth. The active thermal infrared sensor uses a photoelectric sensor that detects reflected IR light emitted and absorbed by the sensor itself. This could be used to detect proximity inside the mouth.

In another embodiment, the dental hygiene implement uses a passive optical sensor to determine whether the implement is within the user's mouth or outside of the user's mouth. The passive optical sensor is a light sensor that triggers the LED when it detects darkness when present inside the user's mouth. For increased sensitivity to changes in light intensity, the light sensor may be sensitive to a wavelength at least 50 nm different from the LED.

In yet another embodiment, the dental hygiene implement uses a photocell to determine whether the implement is within the user's mouth or outside of the user's mouth. A photocell is a light sensor that detects the reflection of light from a second light source on the implement when the implement is turned on. In one embodiment, the photocell may turn on the LED when it detects the reflection of light from a second light source while in the user's mouth.

In another embodiment, the dental hygiene implement uses an ultrasonic sensor to determine whether the implement is within the user's mouth or outside of the user's mouth. The ultrasonic sensor may use echo location to detect the confines of the mouth.

In another embodiment, the dental hygiene implement uses a passive optical sensor to determine whether the implement is within the user's mouth or outside of the user's mouth.

In yet another embodiment, the dental hygiene implement uses a magnetic sensor to determine whether the implement is within the user's mouth or outside of the user's mouth. In one embodiment of the present invention, the magnetic sensor may turn on the LED when it detects the proximity of metals such as the hemoglobin present in blood.

In yet another embodiment, the dental hygiene implement uses a pressure sensor to determine whether the implement is within the user's mouth or outside of the user's mouth. In one embodiment, the pressure sensor may be located under the brush head to detect movement and pressure of the brush head being pressed against the teeth. The type of pressure sensor such may be piezoelectric, cantilever switch, capacitive, potentiometric, optical or electromagnetic. In another embodiment, the pressure sensor may be located on the handle—detects torque and tension in the handle of the brush due to brushing action. The pressure sensor could be Piezoelectric, Cantilever Switch, Capacitive, Potentiometric, Optical or Electromagnetic.

In yet another embodiment, the dental hygiene implement uses a moisture sensor to detect a highly moist environment such as the mouth. This can be accomplished through various types of moisture sensors for example; capacitive or chilled mirror dew point sensors.

In one embodiment, the dental hygiene implement may include electronics having a control circuit to couple the battery and the source of light and the sensor. The sensor may have a closed state when detecting the visible therapeutic light source is inside the mouth of the user, and an open state at other times. In this embodiment, the control circuit may have four states: 1) a light off state when the sensor is in the open state and the visible therapeutic light source is off; 2) a ramp-up sequence when the sensor switches from the open state to the closed state; 3) a light on full state wherein the control circuit supplies about 100% power to the visible therapeutic light source when the sensor remains in a closed state for a duration of time; and 4) a ramp-down sequence when the sensor switches from the closed state to the open state. The control circuit may return to the light off state and cease to supply power to the visible therapeutic light source when the sensor remains in an open state for a duration of time. The control circuit may return to the light off state when the sensor switches from the closed state to the open state during a ramp-up sequence.

In another embodiment, the dental hygiene implement may further include an ionic potential in combination with a light source for use in ionic therapy. The visible therapeutic light and ionic plaque removal have entirely different modalities and in combination provide synergistic advantages above and beyond the benefits of the therapies applied individually. This is because in combination the two modalities target different strains of bacteria thus providing a more holistic approach to oral hygiene and because they affect bonding within bacterial biofilms in different ways.

In another embodiment, the toothbrush may include a communications system for exchanging data with a computing device. The toothbrush generates data about a brushing event and/or light therapy event while a person uses the toothbrush to brush his or her teeth, and the data about the event can be exchanged with the computing device. The computing device may include a tablet, desktop, laptop, tablet and smartphone, and the communications system may be a Bluetooth® communications module that pairs to the computing device using a Bluetooth® protocol. The toothbrush may exchange data with the computing device while paired, and may store data when the computing device is not within a range to be paired with the toothbrush. Once the computing device is within range for pairing, the toothbrush can upload the stored data to the computing device. The data exchanged between the toothbrush and the computing device may include brushing and light therapy habits of the user.

A software application may be installed on the computing device for modifying the settings of the toothbrush and analyzing brushing and light therapy habits of the user. For example, modification of the settings of the toothbrush may include modifying the intensity of the light source. Similarly, analyzing the brushing and light therapy habits of the user may include displaying analyzed results on the computing device. For instance, the analyzed results may include the user's average brushing time and average number of brushes per day. The analyzed results may be shared to a second computing device. Data on the number of joules (or other measures) of light energy may also be collected, analyzed, transmitted, stored and/or displayed.

In another embodiment, the toothbrush may include a second light source that emits light with a wavelength in the range of about 600 nm to about 1000 nm, wherein the second light source is activated when the second light source is in the mouth of the user and the sensor has a closed circuit forming a signal loop.

In another embodiment, the toothbrush may include a light assembly comprising a light source with a light source concentrator installed within the handle. The light source concentrator directs light through a light pipe installed on the distal end and emits light out of an aperture. One example of a light source concentrator is a parabolic concentrator. The parabolic concentrator can emit light at an angle of incidence to create total internal reflection within the light pipe, thereby enabling light to travel along the light pipe while minimizing losses. In one embodiment, the light pipe and light source concentrator are less than about 8 mm in diameter. A concentrator may not be needed if the LED light source were replaced with an unfocussed laser diode with a sufficiently narrow inherent beam width. The light source may be activated by the current signal loop discussed herein, or other sensors as discussed herein.

In certain embodiments, the light source of the light assembly may comprise an array of LEDs on a PCB board. The light source may emit at a wavelength in the range of 400 nm to 500 nm. The toothbrush may further include a beam-steering component to direct emitted light from the light source concentrator to the aperture; for example, a lens. In some instances, the light pipe may comprise a curved surface to guide the emitted light to the aperture. In other instances, the light pipe may comprise a non-conductive plastic.

In another embodiment, the toothbrush handle and the distal end are separable, and the light pipe may align with the light source concentrator when the distal end is mounted on the handle. For example, the distal end may mount on the handle with a bayonet mount. In another example, the distal end mounts on the handle with a press fit. In another example, the handle has a female fitting light source concentrator and the distal end mounts on the handle by insertion in the female fitting. Another example may include an embodiment wherein the handle has a male fitting light source concentrator and the distal end mounts on the handle by insertion of the handle into a female fitting on the distal end.

Other embodiments of the present invention may include combinations of two or more of these sensor types as disclosed above. Furthermore, the sensor examples listed above is not intended to be a complete list of the sensors available for use with the present invention. Therefore, the present invention is not to be limited to the use of the specific sensors or oral care instruments described herein.

BRIEF DESCRIPTION OF THE DRAWINGS

The invention will be better understood by a reading of the Detailed Description of the Examples of the Invention along with a review of the drawings, in which:

FIG. 11 is a partial cross-sectional view of an embodiment of the invention where the sensor is a capacitive displacement sensor placed on the handle;

FIG. 12 is a circuit view of an embodiment of the invention where the sensor is a capacitive displacement sensor;

FIG. 14 shows an embodiment where the sensor is a passive thermal sensor placed near the upper portion of the handle of a toothbrush;

FIG. 15 shows an embodiment where two passive thermal sensors are placed near the upper portion of the handle of a toothbrush;

FIG. 41 is a partial fragmentary perspective view of another embodiment of the invention;

FIG. 42 is a detail view of a switch shown in FIG. 41;

FIG. 43 is a detail view of the switch shown in FIG. 42, the switch being shown in a closed position;

FIG. 44 is a partial fragmentary perspective view of another embodiment of the invention where the oral care instrument is a toothbrush having a Hall effect sensor;

FIG. 45 is a partial fragmentary perspective view of a toothbrush in accordance with another embodiment of the present invention;

FIG. 50 shows a simplified descriptive view of a toothbrush in accordance with another embodiment of the present invention where the sensor is a pressure sensor;

FIG. 51 shows a simple wiring schematic for the toothbrush shown in FIG. 50;

FIG. 52 shows a simple wiring schematic for a toothbrush that includes a three position switch;

FIG. 53 shows a simple wiring schematic for a toothbrush with only one switch;

FIG. 64 shows a perspective view of a toothbrush having a one-piece compressible portion in the handle in accordance with another embodiment of the present invention;

FIG. 65 shows a perspective view of a toothbrush having a two-piece compressible portion in the handle in accordance with another embodiment of the present invention;

FIG. 66 shows a simplified descriptive view of a toothbrush in accordance with another embodiment where the sensor is a pressure sensor;

FIG. 67 shows an enlarged detail of a switch shown in FIG. 66, the switch being shown in a first position;

FIG. 68 shows the switch from FIG. 67 in a second position;

FIG. 70 depicts a toothbrush illustrating various aspects of another embodiment of the present invention wherein the sensor is a moisture sensor;

FIG. 71 depicts another embodiment of a toothbrush wherein the sensor is a moisture sensor;

FIG. 78 is a table showing various sensor types compatible with the interlock sensor software and examples of triggering conditions;

DETAILED DESCRIPTION OF EXAMPLES OF THE INVENTION

Exposing the mouth to light in the visible therapeutic light (i.e. violet and/or blue region of the visible spectrum, between 400 nm and 500 nm) can be useful for a variety of purposes, including destroying bacteria and accelerating the whitening effects of a tooth bleaching agent. However, direct eye exposure should be limited in order to prevent eye damage. Thus, an aim of the present invention is to determine whether an oral care instrument is within the user's mouth or outside of the user's mouth. If the instrument is within the user's mouth, then a light source such as an LED is turned on to emit light. However, if the instrument is outside the user's mouth, the LED shuts off to prevent light exposure to the eyes. As used herein LED includes LED arrays unless otherwise specified. Laser diodes can also be used within the scope of the invention.

Aspects of the invention are illustrated in the remainder of this disclosure with reference to a manual or electric motorized toothbrush, although it is understood that the operation of any number of light-emitting oral care instruments, together with the associated advantageous features and/or beneficial effects described herein, could likewise be achieved. Other oral care instruments may include those used in dental curing lamps, oral flossing implements, water-based flosser, hand-held blue light facial acne treatment devices, and oral surgical instruments, etc.

Figure 1:
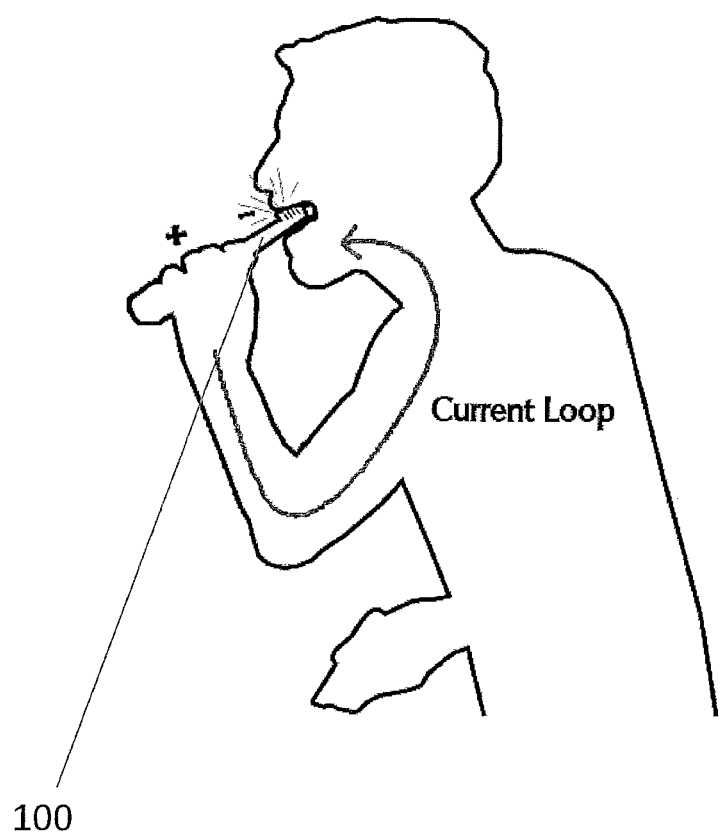
FIG. 1 shows the completion of a signal loop by a user inserting a toothbrush into his mouth.

In one embodiment, as shown in FIG. 1, a light-emitting oral care instrument 100 activates upon the completion of an electrical circuit between the brush handle in contact with the user's hand and contact of the brush head with the user's mouth.

Figure 2:
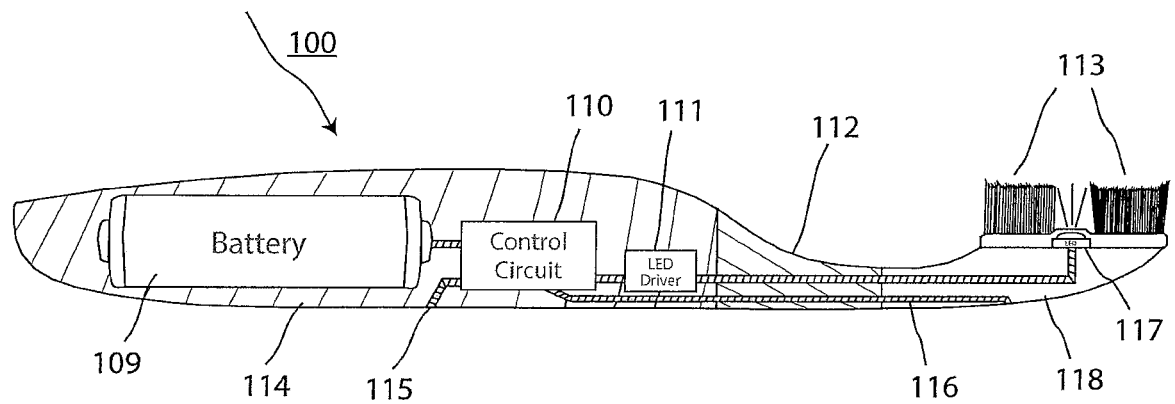
FIG. 2 depicts a representative oral care instrument, a toothbrush, illustrating various aspects.

In the embodiment of the light-emitting toothbrush 100 shown in FIG. 2, the brush head 118 and the handle 114 are injection molded of an electrically-conductive plastic with a non-conductive hydrophobic plastic spacer 112 located between the brush head 118 and the handle 114. The nonconductive plastic spacer 112 electrically insulates the brush head 118 and the handle 114 from each other. The brush head 118 and handle 114 are electrically connected, via a lead 116, to a control circuit 110 that can produce a low level electrical signal. While DC current is likely easiest with a battery source, the signal could be AC. The control circuit 110 can include a high sensitivity current sensor, such as Linear Technology LTC1440 Ultralow Power Single/Dual Comparator with Reference located on the control circuit 110. That comparator is available from Linear Technology Corporation, 1630 McCarthy Blvd., Milpitas, Calif. 95035-74171(408) 432-1900, linear-tech.com.

Figure 6:
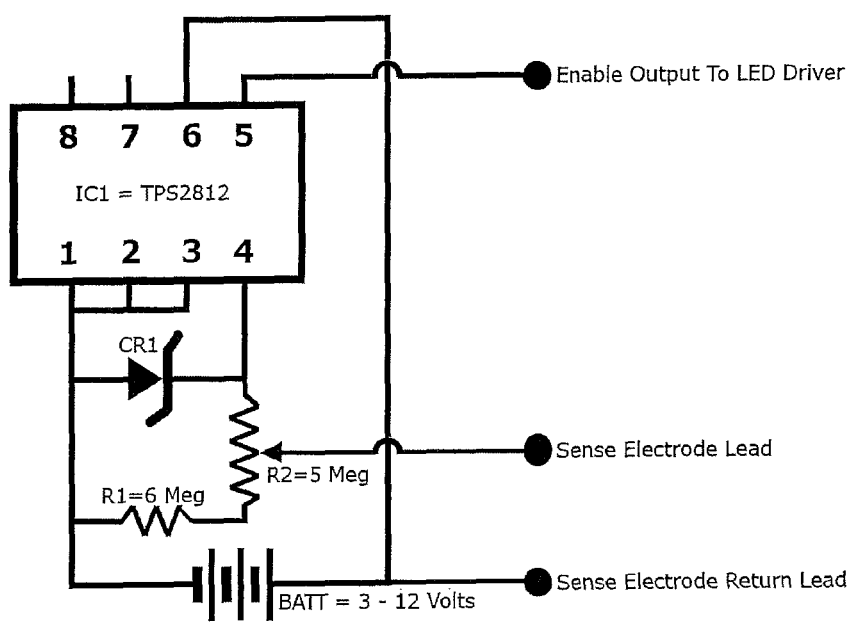
FIG. 6 is a schematic of an exemplary control circuit.

Alternatively, the signal loop sensor circuit can be the one seen in FIG. 6, implemented with off the shelf components. An integrated circuit (IC1) shown in FIG. 6 can be a TPS2812 Dual High-Speed Mosfet Driver available from Texas Instruments, Inc. of Dallas, Tex. One of the sensor electrodes 116 is connected through a battery supplying from three to twelve volts, to pins 1-3 and 6 of IC1. The other sensor electrode 115 is connected across and adjustment bridge variable resistor R2 and to pin 4 of IC1 across resistor R1 to pins 1-3. Pin 4 is tied through Zener diode CR1 to pins 1-3. Pin 5 of IC1 is tied as the output to the LED driver. When the signal loop through electrodes 115 and 116 is completed, the current is sensed in IC1, outputting a signal on pin 5 to activate the driver for the LED.

Prior art toothbrush sensors were implemented with older bipolar transistor technology and required high currents in the signal loop and higher voltages, producing undesirable tingling sensations for the user. The preferred signal loop sensor uses ultra-low-power CMOS technology to reduce the detection current threshold to a sub-microampere level at around one volt of potential difference, preventing any tingling sensation. Another advantage is an ultra-low battery consumption current.

A signal loop is formed through the body of the user by holding the brush handle 114 and placing the brush head 118 or wet bristles of the brush 113 in contact with the mouth. A voltage across the handle and the brush head results in a small signal current that flows through the loop and is detected by the current sensor. The current sensor outputs a signal through the control circuit 110 to the LED driver 111, which delivers current to the LED 117 within the user's mouth, causing the LED 117 to illuminate the mouth of the user. The LED preferably emits short wave length light in the band between 400-500 nm, more preferably 400-450 nm, and more preferably yet of 400-420 nm.

Figure 3:
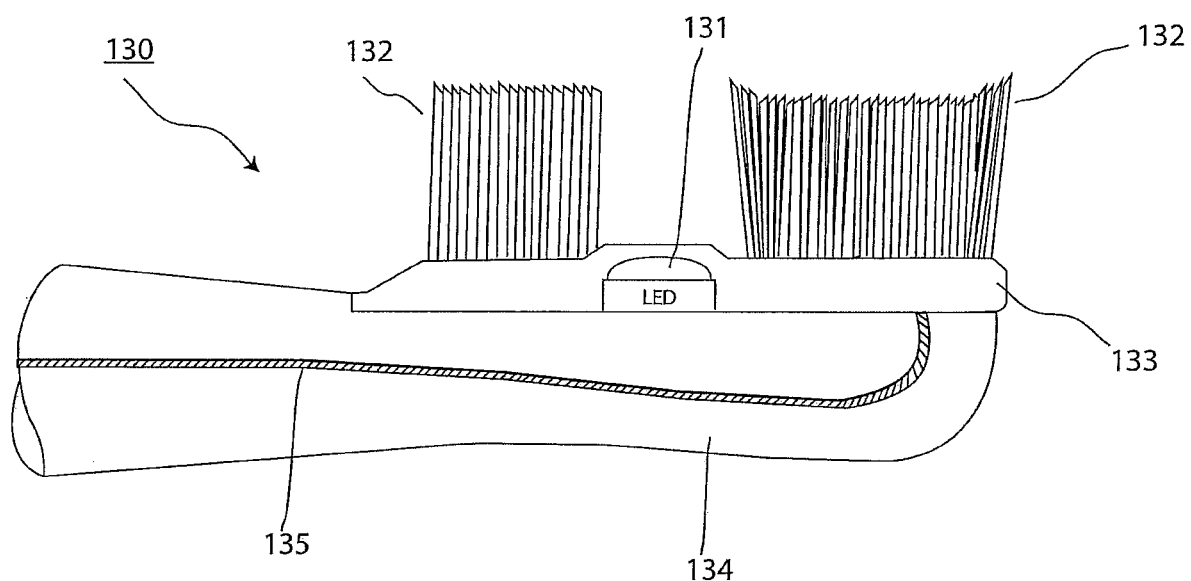
FIG. 3 depicts an alternate embodiment in which the wet bristles of the brush head are conductive to form a contact for completion of the signal loop.

In an alternate embodiment 130 shown in FIG. 3, conductive plastic is used in the part 133 of the brush connecting the bristles 132 to a sheet of conductive plastic 133, instead of the entire brush head. Alternatively, but also possibly in combination, as shown in FIG. 3, the bristles 132 of the brush may also be conductive. When wet bristles 132 come in contact with the mouth of the user during normal brushing operations a circuit is formed via a sense electrode 135 connected to the control circuit 110, which can be used to detect the completion of the electrical signal loop and signals the driver 111 to supply electricity to the LED 131. The remainder of the brushhead 134, is composed of nonconductive plastic.

Typically when brushing teeth, a user will grasp the handle 114 of toothbrush 100, apply toothpaste to the bristles 113 and place the brush head 118 in the mouth and proceed to brush their teeth. While the toothbrush handle 114 is in contact with the user's hand and the brush head 118 is located in the mouth of the user, contact between the electrically conductive plastic of the brush head 118 and mouth of the user completes the signal loop, enabling a small DC or AC current (sensor current) to be initiated and detected by the control circuit 110. The receipt of the sensor current is signaled to the LED driver which, in turn, controls illumination of the LED 117, in this case, turns on the LED 117. When contact between the brush head 118 and the mouth is broken, i.e., when the brush head 118 is withdrawn from the mouth, the signal loop is broken, the flow of sensor current stops, and the LED 117 is turned off. It is to be appreciated that the sensor current required to control the LED 117 will preferably be in the 10 and 100 nanoampere range and would only be detectable with a high sensitivity current meter associated with the control circuitry 110. Due to the use of such a low electrical current, the user will be safe from harm and will not be exposed to danger. The galvanic current generated when a person touches a wet metal object is far greater than the current used in our application, so the current passing through the user's body is harmless and imperceptible.

The electronics, i.e. the LED driver and control circuitry 110 are configured to regulate or adjust the sensor current so that the brush head 118 must be in contact with the user's mouth to turn on the LED 117. Merely contacting the dry skin from hand to hand will not turn the LED 117 on since the dry hand is not as conductive as the wet mouth. This reduces the possibility of turning the LED 117 on merely by handling the toothbrush 100 with bare hands and inadvertently activating the LED 117 while the brush head 118 is not in the user's mouth.

Figure 4:
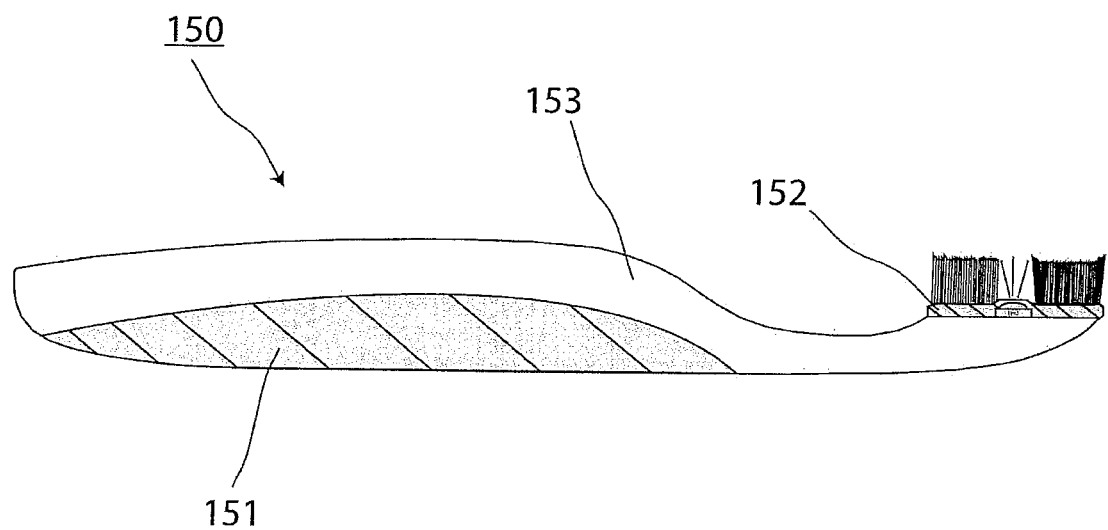
FIG. 4 shows a toothbrush with conductive metal pads.

In a further embodiment of the toothbrush 150 as illustrated in FIG. 4 which is similar to the prior embodiment, the brush head and handle 153 could be formed from a hydrophobic, nonconductive plastic instead of the electrically conductive plastic. In this embodiment, electrically conductive metal pads 151, 152 are located on the exterior surface of the toothbrush 150. One or more metal pads 151 are located on the handle 112' and one or more metal pads 152 are located on the brush head. The metal pads 151 are positioned on the toothbrush 150 for optimal contact with the skin of the hand and pad 152 is mounted for contact with the mouth or bristles of the toothbrush. When the wet tips of the brush bristles are in contact with incisor teeth or mouth and the pad 151 is in contact with the user's hand, an electrical circuit is formed through the body of the user. It is to be understood that the metal pads 152 of the brush head should be spaced apart from the metal pads 151 of the handle.

In use, while the metal pads 151 of the toothbrush handle are in contact with the user's hand and when the brush head 152 is located in the mouth of the user or wet bristles are in contact with any wet portion of the mouth or teeth, contact between the metal pads 152 of the brush head and mouth of the user completes a signal loop, enabling a small DC current (sensor current) to be initiated and detected by the control circuit 110. The sensed current causes the control circuit to activate the LED driver to turn on the LED 126. When contact between the brush head and the mouth is broken, i.e., when the brush head is withdrawn from the mouth, the signal loop is broken, the flow of sensor current stops, and the control circuit turns off.

Figure 5:
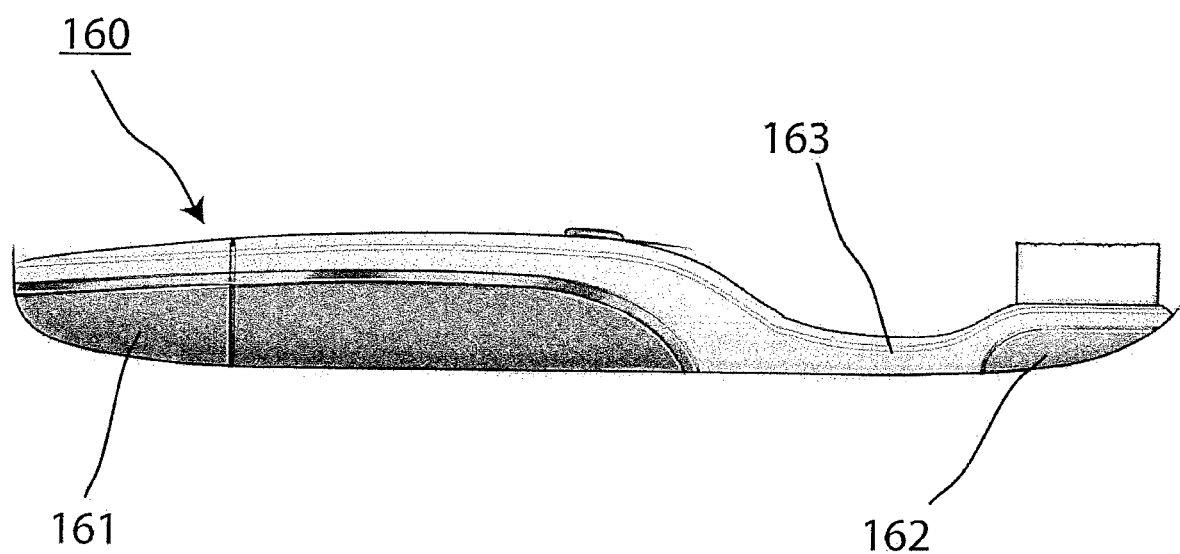
FIG. 5 shows a toothbrush with conductive plastic pads.

A further embodiment 160 is shown in FIG. 5. The handle has a portion 161 of conductive plastic, and the head has a portion 162 of conductive plastic. Portion 163 is nonconductive. The conductive plastic areas are connected internally to circuits as described in connection with FIG. 2 and so the toothbrush of FIG. 5 can be used in like manner to the toothbrush of FIG. 2.

Many electric toothbrushes employ a timer to alert the user of the end of a preset brushing time, for example, two minutes, as recommended by the American Dental Association. These timer circuits are commonly combined with vibration or noise to alert the end user to the completion of a recommended brushing period. The signal loop sensor disclosed herein can be combined with such a timing circuit in a manner that causes elapsed time to be recorded only when the sensor is activated (i.e. light is on). This would facilitate the assurance that the brush timer was actually measuring elapsed time in the mouth of the user and not simply elapsed time of the manual activation of the brush. The control circuit can also include a timer to turn off the LED at a preset time, such as two minutes, signaling to the user that tooth brushing has lasted two minutes. Other ways to signal the user of the completion of two minutes can be substituted.

A conventional make/break switch can be included in one of the conductors 115 or 116 or elsewhere in the electrical circuit, if desired. Thus, the signal loop is completed only if the user closes that switch AND inserts the toothbrush head into the mouth. This can provide a further safety and convenience feature. Alternatively, a make/break switch could be located elsewhere in the circuit from the battery, to the control circuit through the LED driver to LED.

Since the LED will be on only when the light from the LED is safely and effectively used, the life of a charge on the battery should be longer.

The battery can be rechargeable or replaceable, as will be apparent to those of ordinary skill in the art. The toothbrush can be a power toothbrush such as a vibrating, sonic or spin brush or a manual toothbrush.

The brush head and/or neck can be replaceable, as long as the replacement part has the correct electrical contact and a conductor that can reliably connect to a mating conductor in the brush handle. The design can allow the sensor current to flow across the junction of the permanent part and the replaceable part through either two sheets of conducting plastic or a metal connector such as a pin connector. Examples are seen in FIGS. 7 and 8.

Figure 7:
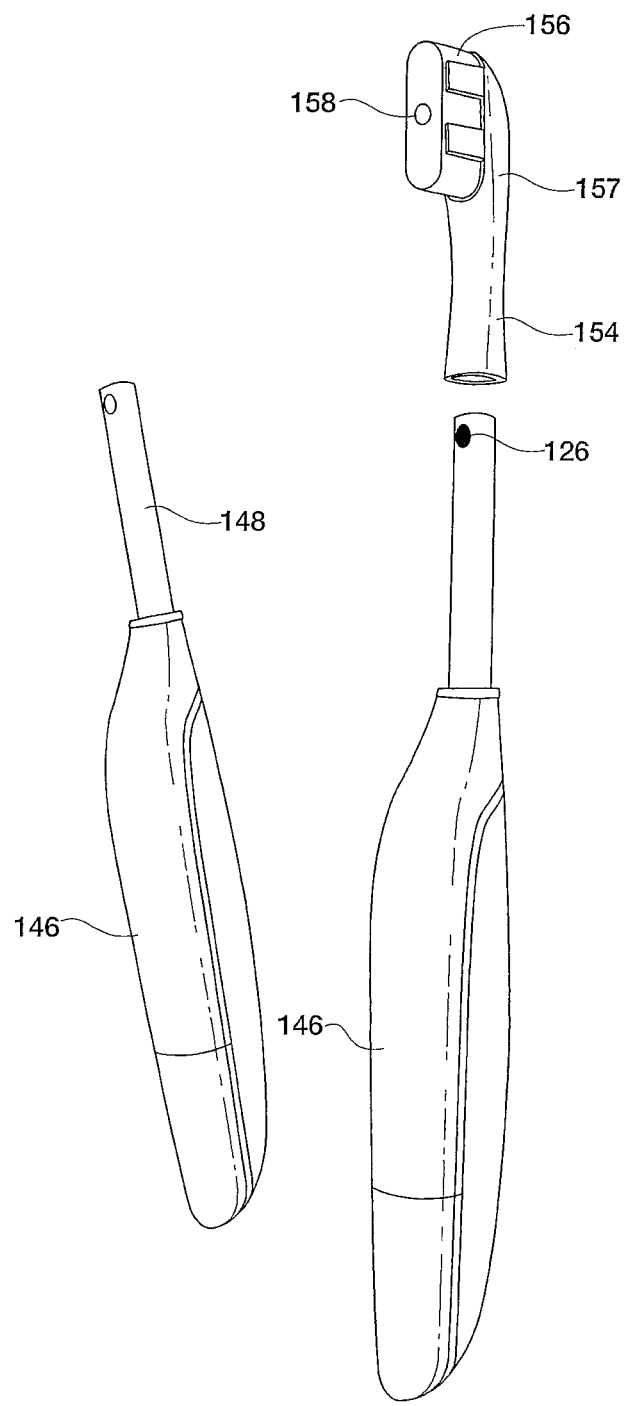
FIG. 7 is a schematic of an exemplary oral care instrument that has a replaceable head and neck.
Figure 8:
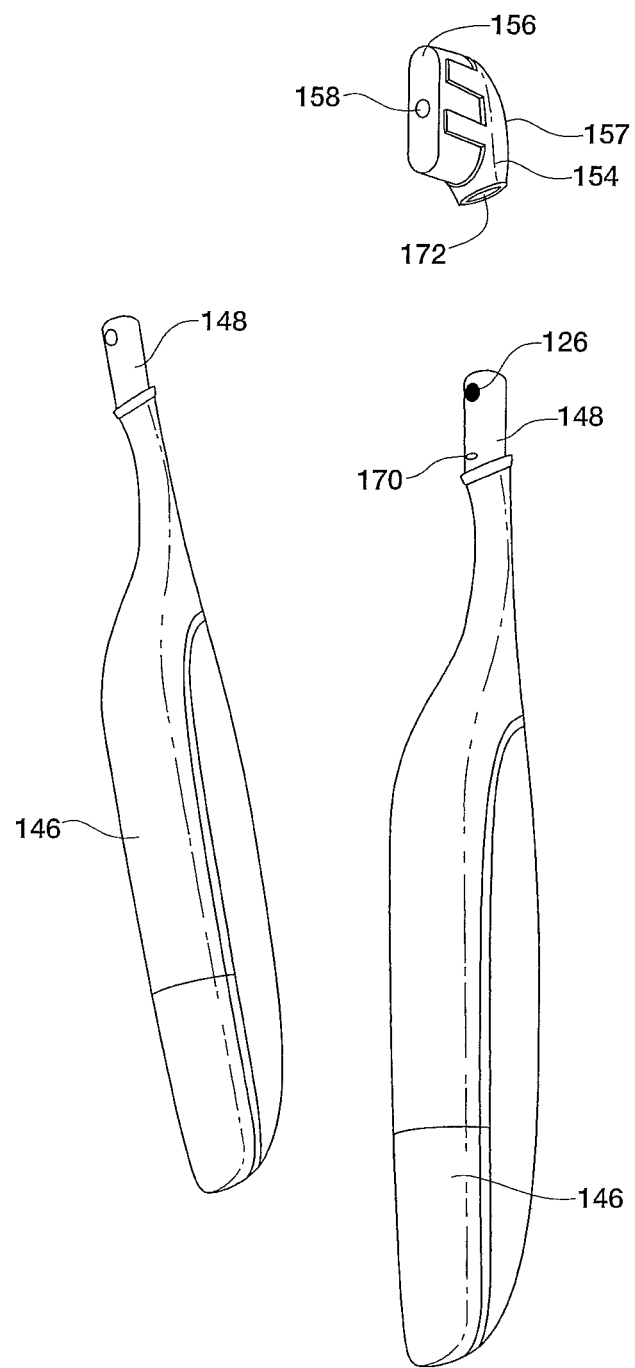
FIG. 8 is a schematic of an exemplary oral care instrument that has a replaceable brush head.

As seen in FIGS. 7 and 8, a brush handle 146 is provided having the necessary battery, charging electronics and LED, all self-contained and water-tightly encapsulated within the handle. The handle includes a stem 148 in which the LED 126 is mounted. FIGS. 7 and 8 show two different embodiments, with the stem 148 in FIG. 7 being longer than the stem 148 of FIG. 8. The replaceable brush head 157 has a hollow shaft 154 of an internal diameter slightly larger than the diameter of the stem 148, so the stem 148 can be inserted into the hollow shaft 154. The brush head has an array of bristles 156 and an opening 158 to allow the light from the LED 126 to pass toward the teeth as they are brushed by the bristles. Preferably the stem and hollow shaft have complementary, non-circular shapes so that the bristles do not rotate around the stem, but stay in a fixed orientation. When the bristles are spent, the brush head 157 can be removed from the stem 148 and replaced with a new brush head. Other appliances appropriate for a tooth whitening brush pattern, light curing of gum infections, tongue scraper, flosser, etc can be configured with similarly shaped hollow shafts so they can also be mounted onto the stem 148.

In the embodiment shown in FIG. 7 the plastic of the stem 148 and the head 157 are made electrically conductive, so that the signal loop can be completed as the user puts the head 157 (as installed on the stem 148) into his or her mouth and grasps the handle 146.

In the embodiment shown in FIG. 8 a conductor in the plastic of the stem 148 has an electrical contact 170; the head 157 has an electrical contact 172 within the shaft 154 positioned to mate with contact 170 when the head is mounted on the stem. The signal loop can be completed as the user puts the head 157 (as installed on the stem 148) into his or her mouth and grasps the handle 146.

A further enhancement of the interlock control feature of this toothbrush can be realized using an AC control signal in place of the DC loop sensor current. A low-frequency 200 Hz to 10 kHz square or sinusoidal waveform AC signal with a peak to peak voltage of no greater than 1 V will be applied to the toothbrush handle. This AC signal will be conducted through the user's body in much the same way as a DC current, as described above. One way to implement this is through selective tone filtering in which a Controlled Oscillator in the handle puts off a square wave form in the low audio band of 1 to 2 kHz. A narrow band tone filter only allows one tone to come through in the brush head. This Selective Tone Filter in the brush head is looking for one certain tone. When it receives that tone, it turns on the LED.

Figure 9:
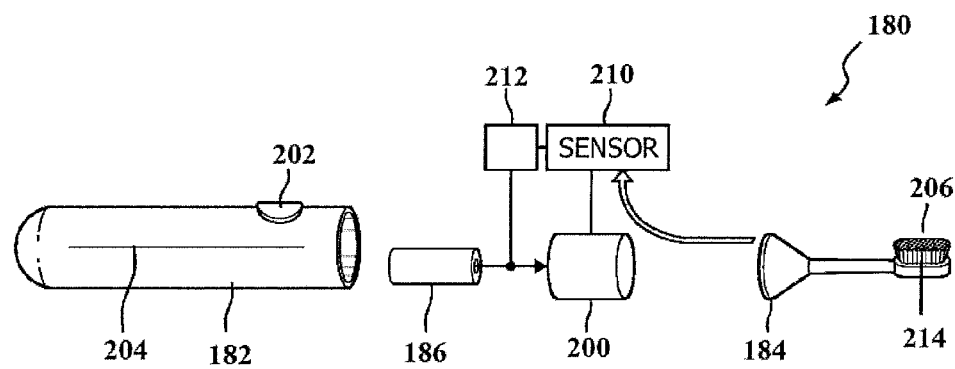
FIG. 9 is an exploded view of a toothbrush with a capacitive sensor.
Figure 10:
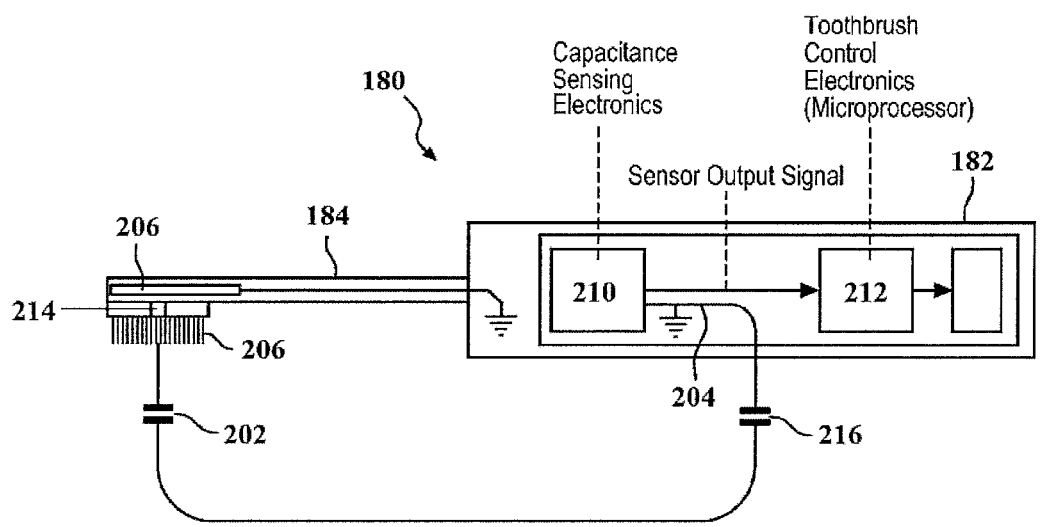
FIG. 10 is a circuit view of the embodiment shown in FIG. 9.

In another embodiment of the present invention, as shown in FIGS. 9 and 10, the sensor used to detect whether the oral care instrument 180 is within the user's mouth is a capacitive sensor. The oral care instrument may be a toothbrush 180 with a battery 186, a LED driver 200, and an on/off switch 202. An electronics ground 204 is located on the handle 182 of the brush. A conductive electrode sensing element 206 is installed preferably on the brush head 184. A sensor system 210 measures the capacitance 216 between the sensing element 206 and the electronics ground 204. A microprocessor/controller 212 determines whether the measured capacitance 216 is above a threshold value, which indicates that the toothbrush 180 is inside the user's mouth. If the measured capacitance exceeds the threshold value, then the LED driver 200 receives a signal and turns on the LED 214. If the measured capacitance drops below the threshold value, then the LED driver turns off the LED 214.

In yet another embodiment, the sensor of the present invention may be a capacitive displacement sensor. One or more tactile sensors are preferably placed on the handle portion of the oral care instrument, and measure capacitance of a conductive target such as the human body. As shown in FIG. 11, the oral care instrument is a toothbrush 220 with a battery 222 and tactile sensors 224, 224' placed on opposing sides of the handle 226. A switch 230 is off when in its first position. When a user grips the handle 226 at both tactile sensors 224 and 224', preferably when the brush head 232 is inserted inside the user's mouth, the capacitive sensor 240 senses an increase in capacitance. As shown in FIG. 12, the capacitive sensor 240 causes switch 230 to move to its second position, signaling the LED drive 234 to turn on the LED 236. An additional on/off switch 242 operated by the user may be installed onto the oral care instrument.

Figure 13:
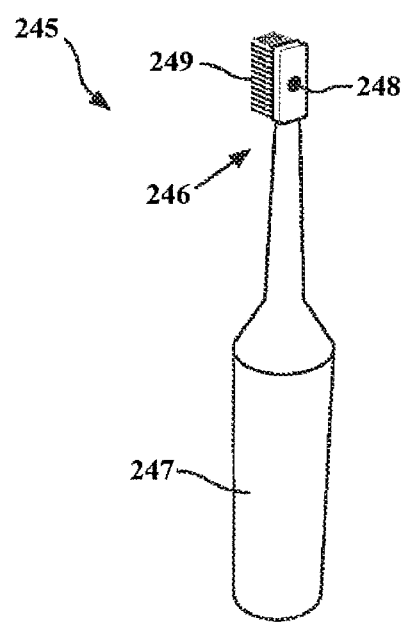
FIG. 13 is depicts an alternate embodiment where the sensor is an inductive proximity sensor.

In another embodiment of the invention, the sensor is an inductance proximity sensor which uses a radio frequency loop to sense the proximity of conductors such as the human body. In one embodiment, as shown in FIG. 13, the dental hygiene implement is a toothbrush 245 having a brush head 246 and handle 247. In this embodiment, the proximity sensor 248 is on the back of brush head 246. The inductance proximity sensor 248 is comprised of an LC oscillating circuit with a signal evaluator. The LC oscillating circuit is comprised of a coil and a capacitor that emits a high-frequency electromagnetic alternating field at the sensing face of the sensor. When the brush head is inserted into the user's mouth, Eddy currents are generated that reduces the oscillations within the LC oscillating circuit. The signal evaluator detects this change in oscillation frequency, and the resulting reduction in oscillations sends a signal to the LED driver to turn on LED 249. When the brush head is removed from the user's mouth, the oscillations from the LC oscillating circuit return to normal and the LED driver turns LED 249 off. Different types of inductor circuits may be used in other embodiments of the present invention.

In another embodiment of the invention, the sensor is a passive thermal infrared sensor. The passive thermal infrared sensor may be placed anywhere on an oral care instrument. In the embodiment shown in FIGS. 14 and 15, the oral care instrument is a toothbrush 250 with a handle 252 and brush head 254. At least one passive thermal infrared sensor 256 is placed near the upper portion of the handle 252 toward the brush head 254. As the user inserts the brush head into the mouth, the microprocessor 260 detects a change in infrared light as detected by the passive IR sensor 256. The resulting increase in IR light causes the microprocessor 260 to turn on LED 262. As the user removes the brush head out of the mouth, the resulting decrease in IR light sensed by the passive IR sensor 256 causes the microprocessor 260 to turn off LED 262.

Figure 16:
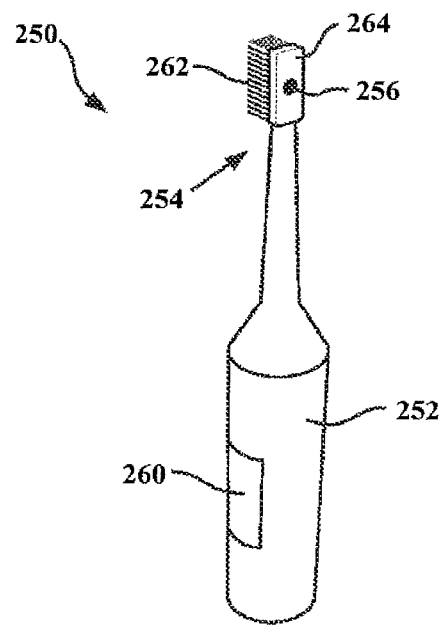
FIG. 16 shows an embodiment where the sensor is a passive thermal sensor placed on the back of the bristle plate of a toothbrush.

In another embodiment, the passive thermal infrared sensor is placed on the brush head as opposed to the handle. In the embodiment shown in FIG. 16, the passive IR sensor 256 is placed on the back of the bristle plate 264. Like the embodiment in FIGS. 14 and 15, if the user places the brush head in his mouth, then the microprocessor 260 will turn on LED 262 due to the increase in IR light as sensed by passive IR sensor 256. As the user removes the brush head out of the mouth, the resulting decrease in IR light sensed by the passive IR sensor 256 causes the microprocessor 260 to turn off LED 262. The change in infrared light as the brush head enters the mouth is understood to be a result of the change in temperature. Thus, it is understood that the passive IR sensor disclosed herein may be substituted with other means for detecting changes in temperature.

Figure 17:
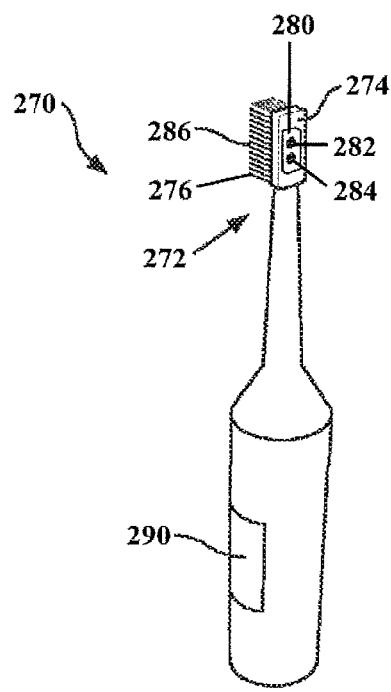
FIG. 17 shows an embodiment where the sensor is an active thermal infrared sensor placed on the back of the bristle plate of a toothbrush.

In another embodiment of the invention, the sensor is an active thermal infrared. This sensor uses a photoelectric sensor that detects reflected IR light emitted and absorbed by the sensor itself. This could be used to detect proximity inside the mouth. The active thermal IR sensor 280 is typically comprised of a light source 282 that emits IR light and a photo diode 284 that detects changes in the sensing environment as the IR emitted from the light source is redirected. In one embodiment, an active thermal infrared sensor is placed on the brush head 272 of a toothbrush 270. The active thermal infrared sensor may be placed either on the front face of the plate with the bristles 276 and LED 286. Alternatively, as shown in the embodiment in FIG. 17, the active thermal infrared sensor 280 may be placed on the back of the bristle plate 274. If the user places the brush head in his mouth, then the microprocessor 290 will turn on LED 286 due to the change in IR light as sensed by photo diode 284. As the user removes the brush head out of the mouth, the IR light returns to a default value as detected by photo diode 284 which causes the microprocessor 290 to turn off LED 286.

Figure 18:
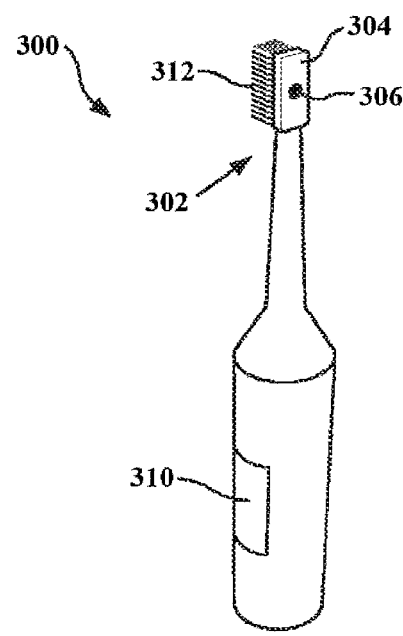
FIG. 18 shows an embodiment where the sensor is a passive optical sensor placed on the back of the bristle plate of a toothbrush.

In another embodiment of the invention, the sensor is a passive optical sensor where the darkness caused by inserting the oral care instrument into the mouth triggers the short wavelength LED to turn on. FIG. 18 shows an embodiment wherein the passive optical sensor is installed on a toothbrush 300. In this embodiment, the passive optical sensor 306 is preferably on the brush head 302 of the toothbrush. In the embodiment shown in FIG. 18, the passive optical sensor 306 is placed on the back of the bristle plate 304. If the user places the brush head in his mouth, then the microprocessor 310 will turn on LED 312 due to the decrease in light as sensed by passive optical sensor 306. As the user removes the brush head out of the mouth, the resulting increase in light sensed by the passive optical sensor 306 causes the microprocessor 310 to turn off LED 312.

In another embodiment of the invention, the sensor is a photocell 314 that detects the reflection of light from a second light source 316 on the oral care instrument. In one embodiment, a photocell is placed on the brush head 322 of a toothbrush 320. The photocell 314 and accompanying light source 316 may be placed either on the front face of the plate with the bristles 324 and LED 330. Alternatively, as shown in the embodiment in FIG. 19, the photocell 314 and secondary light source 316 may be placed on the back of the bristle plate 326. If the user places the brush head in his mouth, then the light emitted by light source 316 will reflect and be detected by the photocell 314. As the reflected light is detected by photocell 314, the microprocessor 332 will turn on LED 330. As the user removes the brush head out of the mouth, the photocell 314 will no longer detect the reflected light which causes the microprocessor 332 to turn off LED 330.

Figure 20:
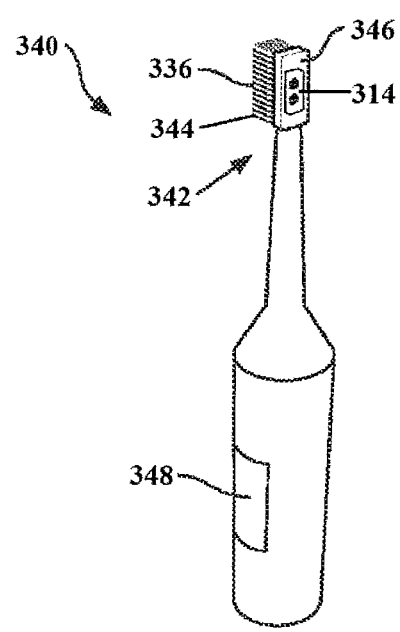
FIG. 20 shows an embodiment where the sensor is an ultrasonic sensor placed on the brush head of a toothbrush.

In another embodiment of the invention, the sensor is an ultrasonic sensor that emits sound waves and uses echo location to detect whether the oral care instrument is within the confines of the mouth. In one embodiment, an ultrasonic sensor 334 is placed on the brush head 342 of a toothbrush 340. The ultrasonic sensor 334 may be placed either on the front face of the plate with the bristles 344 and LED 336. Alternatively, as shown in the embodiment in FIG. 20, the ultrasonic sensor 334 may be placed on the back of the bristle plate 346. If the user places the brush head 342 in his mouth, then the duration that it takes for the sound emitted by ultrasonic sensor 334 to be received back will decrease. The decrease in durational response will cause the microprocessor 348 will turn on LED 336. As the user removes the brush head out of the mouth, the duration that it takes for the sound emitted by ultrasonic sensor 334 to be received back will increase causing the microprocessor 348 to turn off LED 336.

Figure 21:
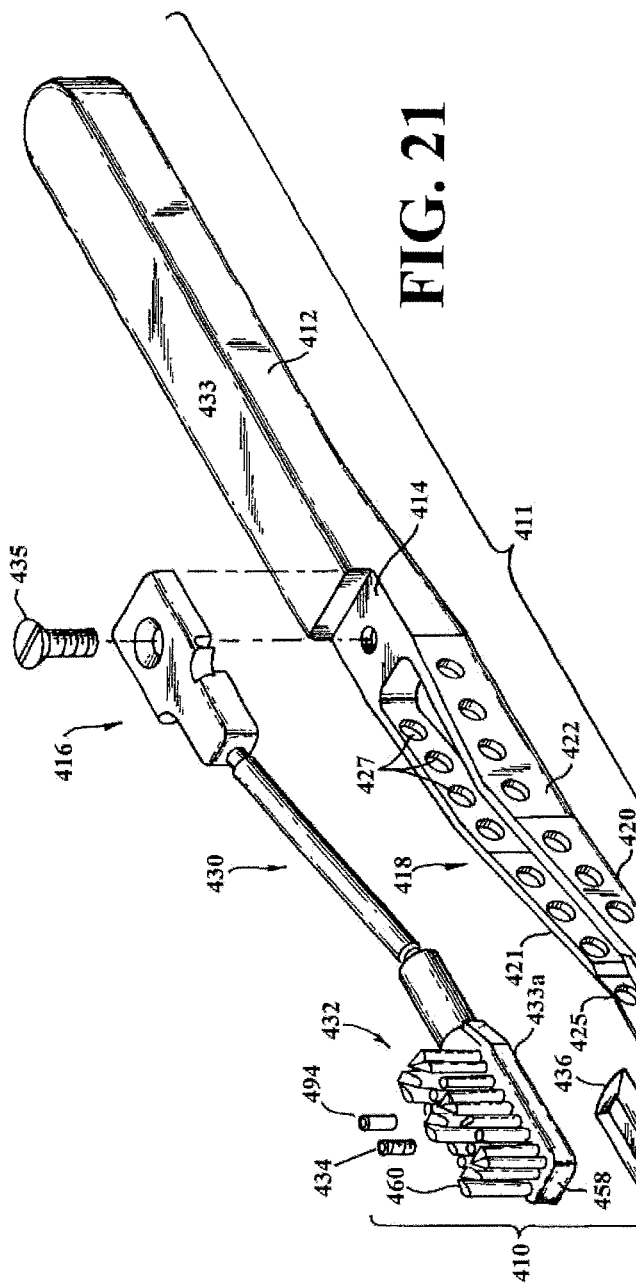
FIG. 21 is a partially exploded view of another embodiment of the present invention, where the sensor is a pressure sensing system.

In another embodiment of the invention, the sensor is a pressure sensor under the brush head that detects movement and pressure of the brush head being pressed against the teeth. FIG. 21 shows the pressure sensing system 410 of the present invention 410 and a toothbrush body referred to generally at 411. Generally, toothbrush body 411 will be a manual toothbrush. The toothbrush body 411 includes a handle portion 412, which is configured to be grasped by the hand of the user. In the embodiment shown, handle 412 is approximately 3.75 inches long, while the entire toothbrush body 411 is approximately 7.5 inches long. In the embodiment shown, toothbrush body 411 is made of a filled nylon, but could be other materials as well, including polypropylene and other plastics. Handle portion 412 is in the embodiment shown approximately 0.5 inches wide and approximately s-inch high. The handle portion 412 is closed about all four sides and its two ends.

Figure 22:
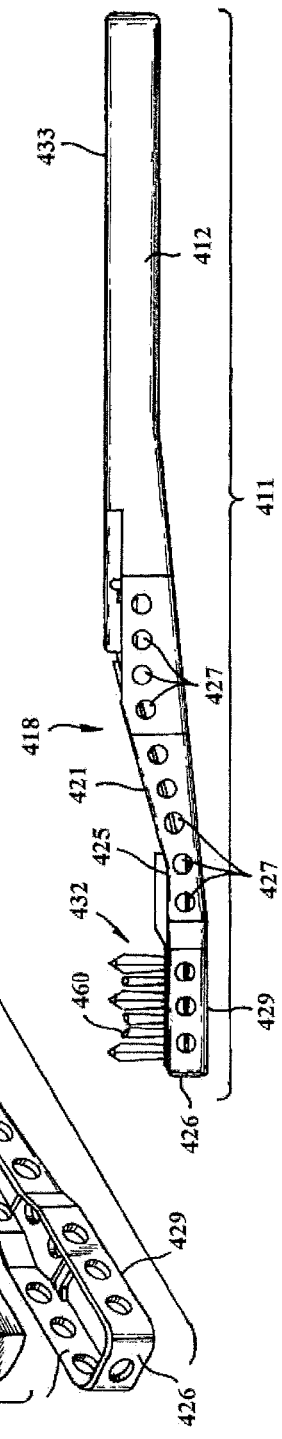
FIG. 22 is a side view of a portion of the pressure sensing system of FIG. 21.

At the distal end of handle 412 is a portion 414 which in the embodiment shown is adapted to receive a hinged member portion 416 of the pressure sensing assembly 410. The remaining portion of the toothbrush body is referred to at 418, and is generally U-shaped in cross-section, open at the top. The remaining portion 418 comprises a base 420, two upstanding sides 421, 423 and a forward end wall 426. This arrangement provides rigidity for the toothbrush body. From the receiving portion 414, toothbrush body 411 begins to taper inwardly at both sides over a short distance until the width of the toothbrush body is approximately 0.25 inches. Over this distance, the top edges of the sides 421, 423 toothbrush body are flat for a small distance and then angle downwardly until point 425 on the toothbrush body. Over this distance, base 420 angles slightly downwardly. The drawings show this structural arrangement, in particular FIG. 22.

From point 425 to forward end wall 426, the toothbrush body is flat and is adapted to receive a conventional toothbrush brushhead 432. The distance from the lower surface 429 of the flat section 431 to the upper surface 433 of handle portion 412 is approximately 0.75 inches, while the height of the toothbrush body in the flat section 431 is approximately 0.28 inches.

The sides 421 and 423 and the base 420 over the length of the toothbrush body from receiving portion 414 to the forward end wall 426 have a plurality of openings 427-427 therethrough. In the embodiment shown, these openings are circular, approximately 0.125 inches in diameter, spaced approximately 0.25-0.35 inches apart. In base 420 of flat section 431 is an elongated slot 437, which is discussed in more detail below. The openings could have other shapes and spacing, however. The use of openings, with an entirely open top, has several advantages. It allows fluid to easily escape the brush, without trapping oral tissue in the openings. This arrangement further permits the use of the hinged arm pressure sensing assembly 411 without the use of seals between the arm and the body. The openings further are large enough to not only allow rinsing water to move freely in and through the toothbrush body during cleaning, but also allows the unit to dry out thoroughly between uses.

Figure 24:
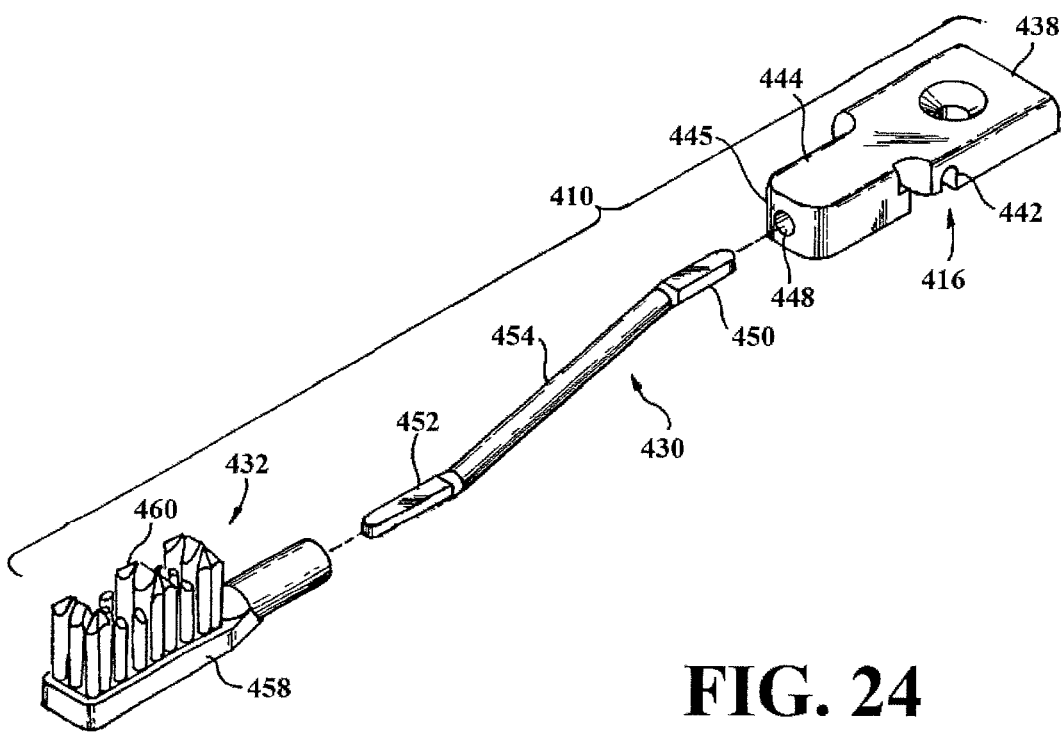
FIG. 24 is an exploded view of the pressure sensing system of FIG. 21.
Figure 25:
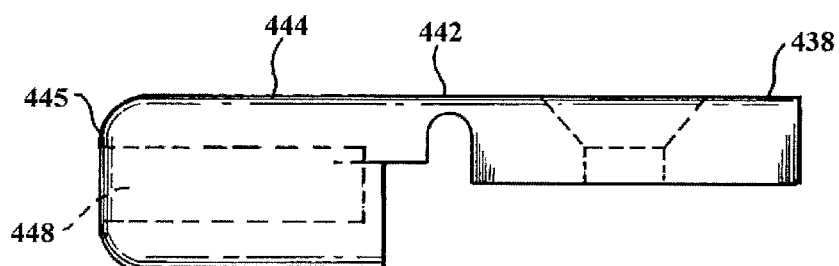
FIG. 25 is a side elevational view of a portion of the pressure sensing system of FIG. 21.
Figure 26:
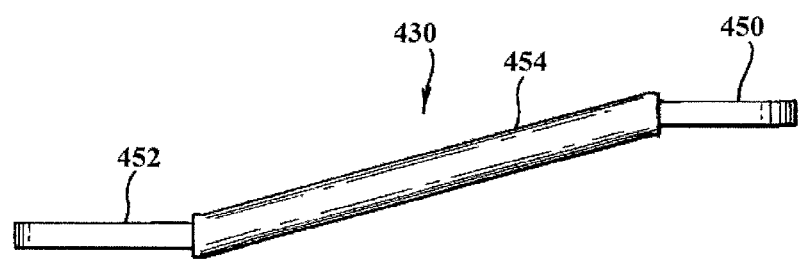
FIG. 26 is a side elevational view of another portion of the pressure sensing system of FIG. 21.

The pressure sensor assembly 410 is shown in relation to the toothbrush body 411 in FIG. 21, and in an exploded view by itself in FIG. 24. Two of the component parts thereof are furthermore shown in more detail in FIGS. 25 and 26. The pressure sensor assembly/system includes a hinged member 416, an elongated arm 430, a brushhead 432 which includes a striking element 434 extending away from a rear surface 433 of the brushhead, and a deformable dome element 436, conventionally referred to as a "snappy" member, since it makes a snap-like sound when deformed past a threshold point. Most round snap domes cannot be moved beyond a "flat" position without turning inside out. The rectangular snap dome shown and described herein can be moved to a "beyond flat" position, thereby providing a longer collapsing distance and greater tactile feel.

Hinged member 416 is attached to toothbrush body 411 at receiving portion 414, by means of a screw 435 or the like. It could also be a quick disconnect arrangement to allow convenient replacement of the brushhead. Hinged member 416 in the embodiment shown is made from polypropylene or acetal resin (Delrin) or similar plastic. The hinged member 416 (FIG. 25) includes a rear portion 438 which is approximately square in the embodiment shown and approximately ⅛-inch thick. Forward of base portion 438 is a narrow hinge portion 442 which in the embodiment shown is approximately 0.015 inches thick, which is sufficiently thin to permit a hinge-like action, and approximately one-half inch wide.

Forward of hinge portion 442 is a receiving portion 444, which is approximately 0.25 inches thick. The receiving portion 444 is approximately 0.3-0.5 inches wide at hinge portion 442 and tapers to approximately 0.3 inches at a forward end 45 thereof. The longitudinal edges of the receiving portion 444 are in the embodiment shown rounded. The receiving portion 444 is configured to fit within the toothbrush body, near a rear end of the remaining open portion 418 thereof. An octagonal (in cross-section) central opening 448 extends longitudinally inward of receiving portion 444 from forward end 445 and receives one end of an arm 430.

Elongated arm 330 in the embodiment shown (FIG. 24) includes proximal and distal portions 450 and 452, connected by an intermediate rod-like portion 454. In the embodiment shown, arm 430 is made from stainless steel, but other materials could be used as well, such as various plastic materials. Proximal portion 450 is approximately 0.4 inches long and is configured to snugly fit into opening 448 in receiving portion 444 of the hinged member, while distal portion 452 upon which brushhead 432 is mounted is approximately 0.5 inches long. The intermediate portion 454 is approximately 1.328 inches long in the embodiment shown.

The arm 430 has a total length of 2.245 inches, because the intermediate portion is arranged such that it angles downwardly between the proximal and distal portions. The distance between the centerlines of the proximal and distal portions is approximately 0.35 inches. The angle of the intermediate portion of the embodiment shown is approximately within the range of 5°-20°, preferably 15°. The intermediate portion 454 is configured to closely follow the portions of the toothbrush body in which it fits.

Although the hinged member 416 and arm 430 are shown as two pieces in the present embodiment, they could be made, i.e. molded, as a single unit.

Mounted on distal end portion 452 of arm 430 is a brushhead 432. Brushhead 432 includes a base portion 458 and a bristle portion 460 which is mounted in base 458 and extends upwardly therefrom in conventional fashion. The bristle portion can take various configurations, including conventional arrangements or special configurations to accomplish particular brushing effects. In the arrangement shown, the tops of the bristles are in approximately the same plane as the hinge portion 442 of the hinged member to prevent in/out brushing forces at the bristle tips from causing turning moments around the hinge member and distorting the accuracy of the force sensing system. The combination of the hinged member 416, arm 430 and brushhead 432 can be replaceable as a unit if desired.

Mounted in the base of the brushhead, approximately central thereof in the embodiment shown, is a set-screw which is the striking element 434. The set-screw extends through the base portion 458 and below the lower surface 433 of the brushhead, approximately 0.08 inches in the embodiment shown. The setscrew in the embodiment shown is approximately 3/32 inches in diameter and ⅝ s inch long and is made from stainless steel. Alternatively a bump could be molded into the toothbrush base portion 458. Further, the hinged element, the arm and the brushhead could be a single piece. The brushhead 432 could also be made removable from the arm portion.

When hinged member 416 is secured to the receiving portion 414 of the toothbrush body, application of force against the brushhead 432 toward the toothbrush body will result in the brushhead moving about hinged portion 442 of hinged member 416.

Figure 27:
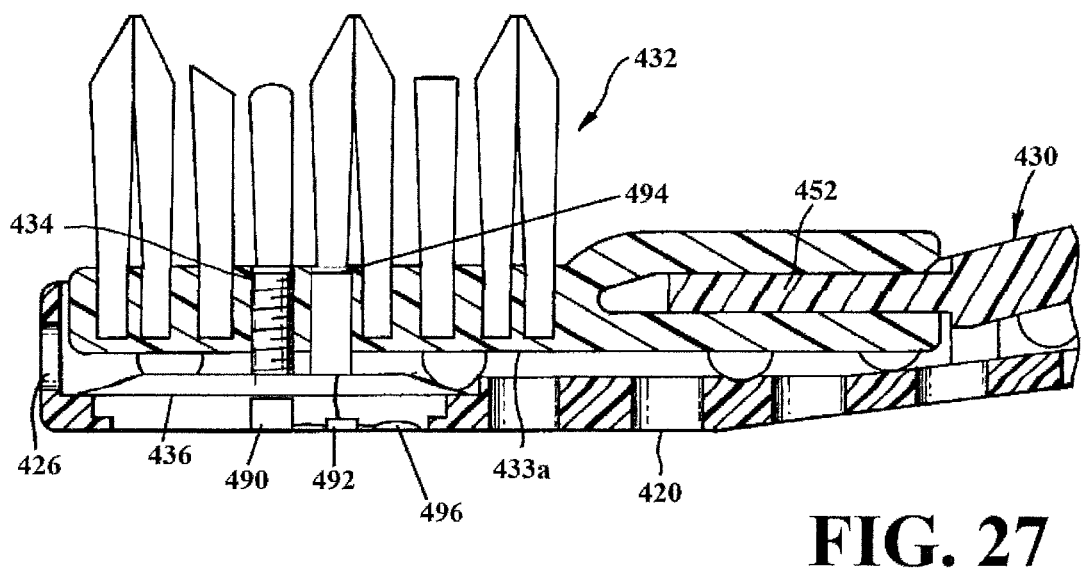
FIG. 27 is a cross-sectional view of a portion of the pressure sensing system of FIG. 21.

A thin dome element 436 is secured to interior surface of flat section 431 of the toothbrush body, directly beneath base portion 458 of the brushhead. Dome element 436 in the embodiment shown is a conventional snap dome member having an obround configuration, similar generally to a child's "cricket" toy. The obround snap dome element 436 is capable of moving "beyond flat" when it suddenly collapses due to pressure against it exceeding a particular value by action of the striking element 434. This is shown by the dotted lines in FIG. 27. The "beyond flat" capability, as discussed above, is important to provide a sufficient collapsing distance that the user can recognize the collapse of the element. The snap dome is mounted on a ridge within the brushhead receiving portion to permit the center portion of the snap dome element to go beyond flat.

In the embodiment shown, the dome element collapses approximately 1/16 inch, and beyond flat by approximately 0.045 inches. The force necessary to collapse the dome is preferably under 200 grams, since selected force values above this range are generally considered as a threshold for excessive pressure. Snap dome elements are available with various collapse forces.

By default, a switch 490 is in an "off" state. In one embodiment, when the snap dome 436 collapses it mechanically triggers the switch 490 to an "on" state. Turning the switch onto its "on" state closes the circuit containing battery 496 and causes the LED driver 492 to turn on the LED 494. While the snap dome 436 remains collapsed due to the pressure applied when a user brushes his teeth, the LED 494 remains on. Other types of switches may be used, including a magnetic sensor where the striking element 434 causes a first magnetic plate to come into contact with a second magnetic plate.

Figure 23:
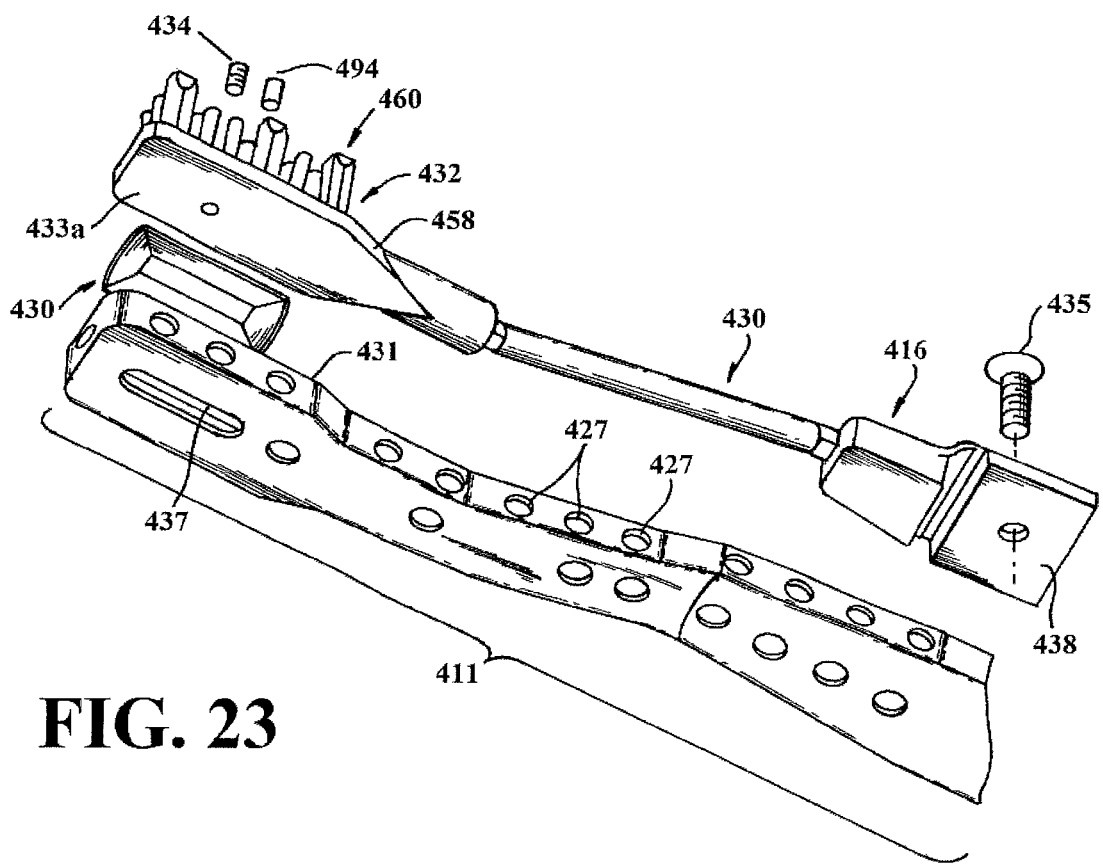
FIG. 23 is a perspective view of the pressure sensing system of FIG. 21.

The snap dome is secured to the toothbrush body beneath the brushhead by means of an adhesive or tape or a trapping element. Slot 437 (FIG. 23) in the base portion of the toothbrush body extends beneath the snap dome, and prevents the possible damping of the snap dome action due to fluid being trapped beneath the dome when it collapses. The slot allows the ready escape of the fluid from the toothbrush body and allows for complete rinsing and drying of the toothbrush between uses.

In the embodiment shown, the snap dome element is secured to the toothbrush body beneath the brushhead and the striking element extends from the brushhead. In another embodiment, the snap dome element could be positioned on a lower surface of the brushhead and the striking element could be positioned on the toothbrush body beneath the brushhead.

Other pressure sensors may be used with the present invention. Toothbrush 510 for sensing pressure applied during brushing and for indicating when the pressure exceeds a predetermined value is shown in partial cross-section in FIG. 29. Toothbrush 510 includes a piezoelectric film 524 disposed within brush head 512 and an indicator circuit 530, including LED 534, disposed within handle 508. A pressure sensor can use a cantilever switch located in the brush head connected to a moving segment of the bristle bed.

Figure 30:
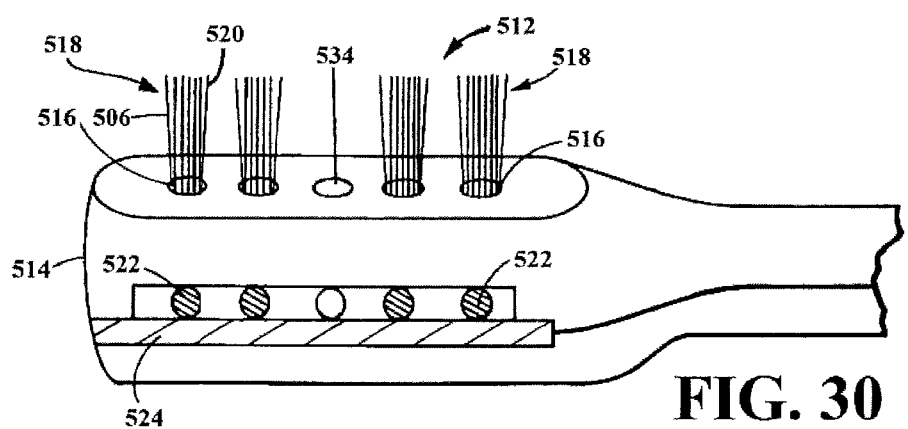
FIG. 30 is an enlarged detail view of a portion of the toothbrush shown in FIG. 29.

Referring to FIG. 30, an enlarged cross-sectional view of brush head 512 is shown. Tufts 518 of bristles 506 extend through openings 516 in member 514 of head 512. Each tuft has a crest end 520 extending outward from opening 516 and a root end 522 disposed beneath opening 516 in member 514. The length of bristles extending between crest end 520 and root end 522 of tuft 518 has a cross-sectional dimension that is less than the cross-sectional dimension of opening 516 so that tuft 518 can move axially through opening 516 and retract downwardly toward piezoelectric film 524. The cross-sectional dimension of root end 522 is greater than the cross-sectional dimension of opening 516, which inhibits root end 522 from passing through opening 516 and retains tuft 518 within head 512.

Piezoelectric film 524 is disposed within head 512 beneath root ends 522 of tufts 518 so that film 524 will experience strain when pressure is applied to tufts 518. When pressure is applied to tufts 518, root ends 522 are forced into contact with piezoelectric film 524. The pressure exerted by root ends 522 on film 524 causes a change in the strain of film 524, which causes film 524 to generate voltage. As is well known in the piezoelectric art, piezoelectric films carry a permanent dipole moment that, when the film is at rest, is cancelled out by charges in the atmosphere. Deforming the film, i.e., applying a force to the film that generates a strain, changes the orientation of the polymer backbone of the film, which causes the strength of the dipole to change and generates an electrical voltage. If the piezoelectric film comes to rest in its deformed position, i.e., the pressure applied is constant and no new strain is generated, the new dipole will again be cancelled out by atmospheric charges and the voltage will cease. As long as the orientation of the polymer is being changed by application of a varying degree of pressure to the film, voltage will be generated.

Figure 28:
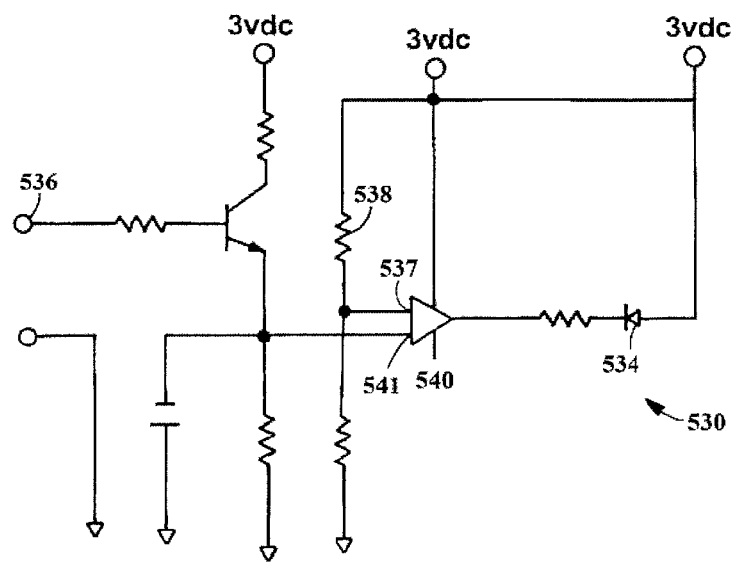
FIG. 28 is a schematic drawing showing a circuit according to another embodiment of the invention where the sensor is a pressure sensing system.
Figure 29:
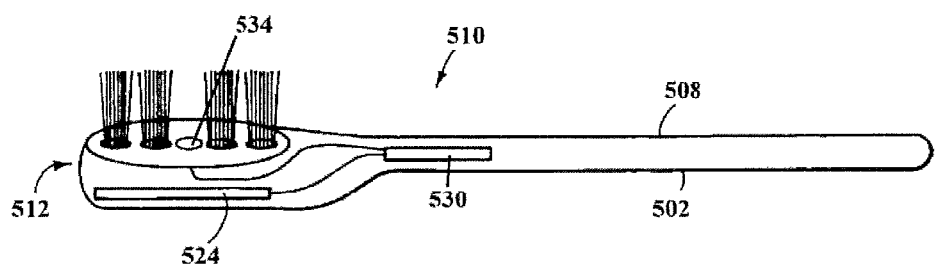
FIG. 29 is a schematic perspective view, in partial cross-section, of a toothbrush having a pressure sensing system according to another embodiment of the invention.

Referring to FIGS. 28 and 29, indicator circuit 530, located within the handle 508 of toothbrush 510, senses the voltage generated in piezoelectric film 524 and determines whether the voltage generated is greater than a predetermined value, e.g., a value that represents a level of brushing pressure. If the voltage is greater than the predetermined value, then indicator circuit 540 turns LED 534 on. If the voltage drops below the predetermined value, then the indicator circuit 540 turns LED 534 off. Any circuit capable of receiving a signal from the piezoelectric film, determining if the signal is greater than a predetermined value, and subsequently turning on the LED 534 can be used as the indicator circuit. Such circuits can be readily constructed by those skilled in the art.

One example of a suitable indicator circuit is shown in FIG. 28. The voltage generated in piezoelectric film is transferred via lead 536 to an indicator circuit 530 that includes comparator 540 and a single LED 534. LED 534 turns on when the output voltage from the piezoelectric film (applied to variable input 541 of comparator 540) exceeds the voltage drop across resistor 538 as applied to reference input 537 of comparator 540.

The LED of the indicator circuit is preferably located on the toothbrush in such a way that it is not seen by the user when brushing. Thus, the LED is preferably located at the brush head 512.

Figure 31:
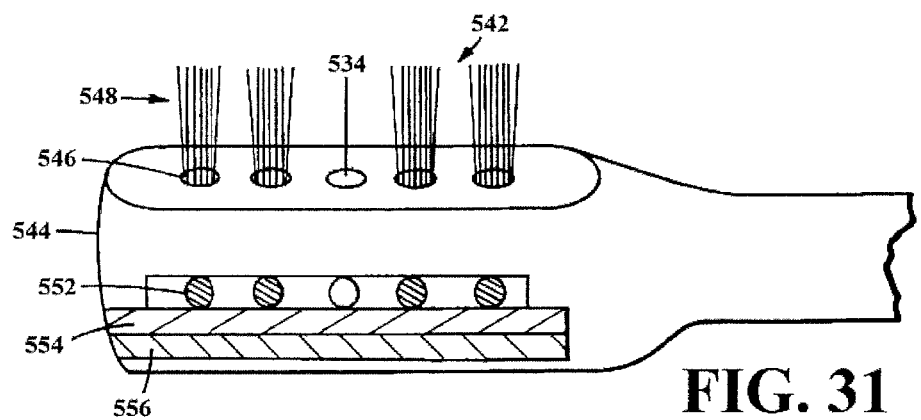
FIG. 31 is an enlarged detail view, in partial cross-section, of a toothbrush head according to another embodiment of the invention where the sensor is a pressure sensing system.

Referring to FIG. 31, an alternate embodiment of toothbrush head 542 is shown in which a resiliently deformable membrane material 556 capable of resilient spot deformation, i.e, a membrane that has highly localized zones which can be resiliently displaced relative to the rest of the membrane without affecting the zones immediately adjacent to the displaced zone, is disposed beneath piezoelectric film 554. Such a membrane material is described, e.g., in U.S. Pat. No. 4,633,542 (Taravel), the disclosure of which is hereby incorporated herein by reference.

When the toothbrush is at rest, i.e., when no pressure is applied to tuft 548 urging it against piezoelectric film 554, membrane 556 is taut and resiliently biases root end 552 of tuft 548 against member 544. When pressure is applied to tuft 548, tuft 548 retracts into contact with piezoelectric film 554 by sliding through opening 546 and causing resilient spot deformation of membrane 556 at the point where tuft 548 is urged against piezoelectric film 554, without displacing the contact zones between the root ends of the respective immediately adjacent tufts and the membrane. Once the strain is released from the membrane, the membrane material regains its original structure. When the toothbrush is removed from the oral surface, i.e., the pressure is removed, tufts 548 return to their initial position with their respective root ends 552 abutting against member 544 by virtue of resilient membrane 556 returning to its initial position. Membrane 556 is preferably under tension since tension facilitates this spot deformation.

Membrane 556 is preferably formed from an isotropic elastomeric material selected for its ability to behave anisotropically in that it gives the membrane the property of being able to exhibit resilient deformation in localized spots. The choice of material for the membrane and the appropriate thickness are readily determined by the person skilled in the art as a function of the mechanical characteristics and, in particular, the elasticity required for the membrane. Suitable membrane materials include, e.g, natural or synthetic latex type elastomers (e.g., polychloroprenes), natural rubber, and silicones.

The thickness of the membrane in the relaxed state will generally vary in the range of 0.10 mm to less than 1 mm. Such a thickness will enable localized or spot resilient deformation with an amplitude of 0.5 mm to 5 mm for a force of about 1 Newton (N) to 7.5 N (i.e., about 150 grams-force to about 750 gf) applied in a distributed manner over the set of tufts of bristles.

Figure 32:
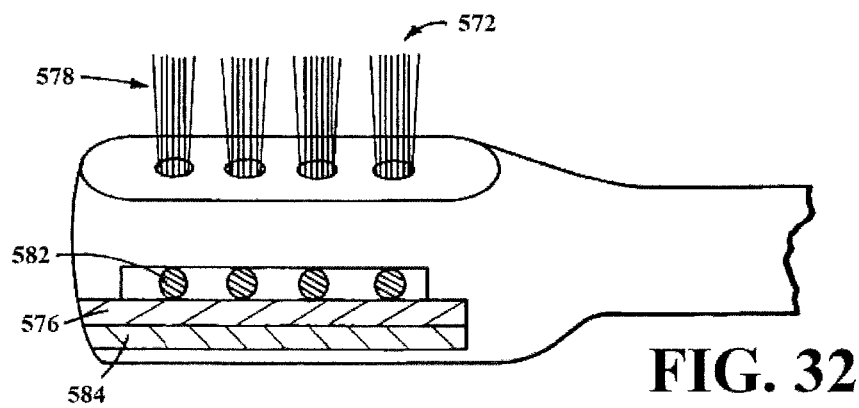
FIG. 32 is an enlarged detail view, in partial cross-section, of a toothbrush head according to another embodiment of the invention where the sensor is a pressure sensing system.

Alternatively, membrane 576 may be disposed above piezoelectric film 584 between root ends 582 of tufts 578 and piezoelectric film 584, as shown in FIG. 32.

Figure 33:
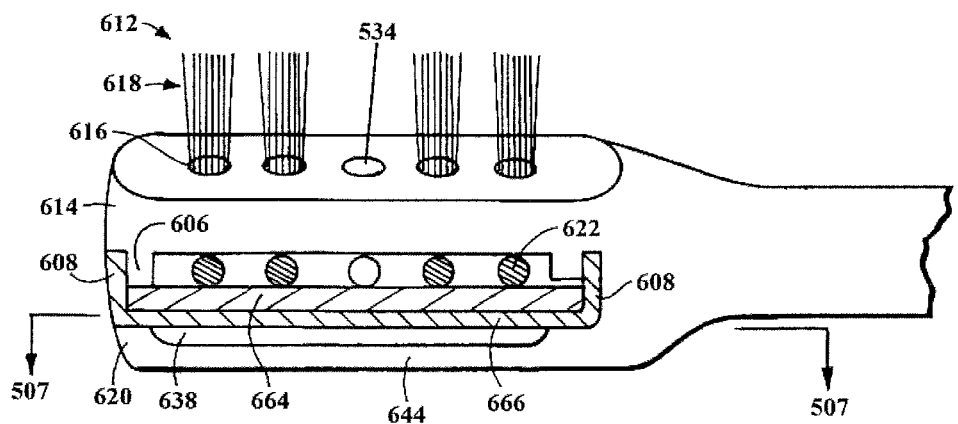
FIG. 33 is an enlarged detail view, in partial cross-section, of a toothbrush head according to another embodiment of the invention where the sensor is a pressure sensing system.

Referring to FIG. 33, in another embodiment, membrane 666 extends across a cavity 638 defined by member 644 in head 612 so as to seal cavity 638. The toothbrush also includes piezoelectric film 664. During assembly of the toothbrush membrane 666 is fixed, while taut, to head 612 at the periphery of cavity 638. Cavity 638 and membrane 666 enclose a cushion of air, the presence of which facilitates vertical spot deformation of membrane 666 in response to axial retraction of a tuft of bristles. Member 614, which is made of rigid material, e.g., a plastic material, like the remainder of the brush head, is fixed to the brush head and together therewith clamps the membrane in continuous manner all around the periphery of cavity 638. Member 614 may be a separate piece forming a rigid extension of the head or may be integrally molded with the head.

Figure 34:
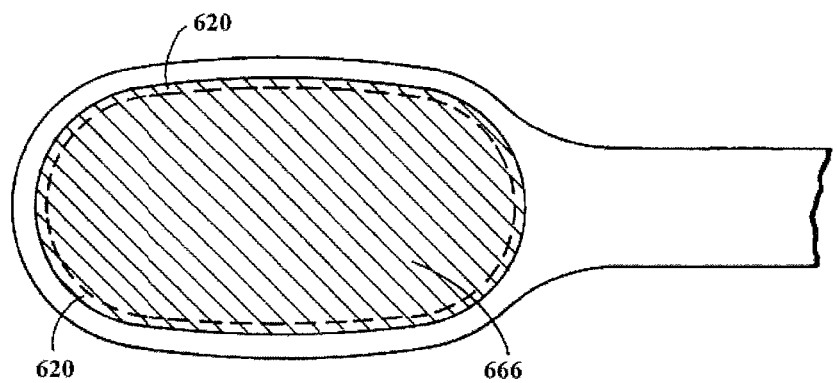
FIG. 34 is a detail view of the toothbrush head of FIG. 33 taken along 507-507.

A continuous rim 606 projects substantially perpendicularly from an area near the perimeter of member 614. A continuous peripheral zone 608 of membrane 666 is clamped between the side of head 612 and rim 606 thereby fixing membrane 666 to the head and ensuring that membrane 666, member 614 and head 612 are fixed relative to one another. In addition or alternatively, membrane 666 may be affixed to rim 620 around the edge of cavity 638, e.g., by glue or a heat weld, as shown in FIG. 34.

Any method may be used to fix the periphery of the membrane to member 614 or rim 620, provided the portion of the membrane that contacts the root ends 622 of tufts 618 remains resiliently deformable. Tufts 622 retract into and are biased by membrane 666 in the same manner as discussed above with reference to FIGS. 31 and 32.

Other embodiments are within the claims and include, for example, an embodiment in which the piezoelectric film extends across a cavity, e.g., the cavity shown in FIG. 33, in the absence of a membrane. In another embodiment, the indicator circuit is located external to the toothbrush.

In another embodiment of the invention, the sensor is a pressure sensor in the neck that detects torque and tension in the neck of the brush due to brushing action. The pressure sensor could be Piezoelectric, Cantilever Switch, Capacitive, Potentiometric, Optical or Electromagnetic. Such a pressure sensor is disclosed in US 20030205492 to Ferber et al, and is hereby incorporated by reference.

Figure 35:
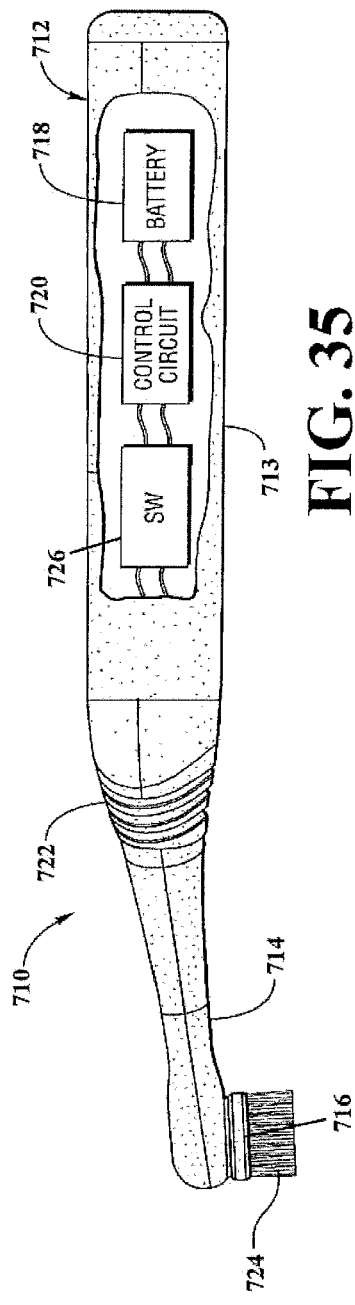
FIG. 35 is a simplified descriptive view of another embodiment of the invention where the sensor is a pressure sensing system.

FIG. 35 shows a simplified descriptive view of a light emitting toothbrush 710 in accordance with the present invention. The toothbrush 710 includes a toothbrush body 712 that has a handle portion 713 and a brush head portion 714. Within the brush head portion 714 is light source 716. The light sources 716 are powered by a battery 718, and controlled by electrical circuitry, or a control circuit 720. Although only one battery 718 is illustrated in FIG. 35, it is contemplated that more than one battery may also be used. The toothbrush body 712 includes a flexible portion 722 that facilitates some movement of the brush head portion 714 when a force is applied to the brush head portion 714, for example, when bristles 724 are applied to an operator's teeth. A switch 726, which is configured to activate the light source 716, is actuated when a first predetermined force is applied to the brush head portion 714.

The interaction of the switch 726 and the movement of the brush head portion 714 exemplifies one of the benefits of the present invention. It has been shown that effective brushing occurs when a force of 2N-3N is applied in a direction normal to the teeth. When the brushing force is significantly less than 2N, cleaning of the teeth may not be adequate. When a brushing force of significantly more than 3N is applied to the teeth, unacceptably high levels of enamel abrading may occur.

For example, referring to the toothbrush 10 illustrated in FIG. 35, the brush head portion 714 moves slightly as the bristles 724 contact an operator's teeth. As more force is applied, the movement of the brush head portion 714 will increase. It is contemplated that as the force reaches the level of a predetermined force, for example, a force of approximately 2N, the movement of the brush head portion 714 will actuate the switch 726 and the light source 716 will be activated. To ensure that the brushing force meets the minimal level desired, the switch 726 may be configured with a spring actuator having a known stiffness. Thus, the switch 726 could be configured such that it is actuated only when a force of at least 2N is applied to the brush head portion 714. Of course, the predetermined force, or minimum required brushing force, can be changed by configuring the switch 726 with a spring actuator having a different stiffness.

As an alternative to configuring the switch 726 with a spring actuator to control activation of the light source 716, a load cell, or force sensor 728 (illustrated in FIG. 38 and discussed in more detail below), can be included in the toothbrush 710 to ensure that the light source 716 is activated upon application of the predetermined force.

Figure 37:
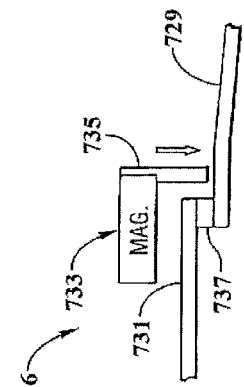
FIG. 37 is a partial fragmentary view of the switch shown in FIG. 36, the switch being shown in a second position.
Figure 36:
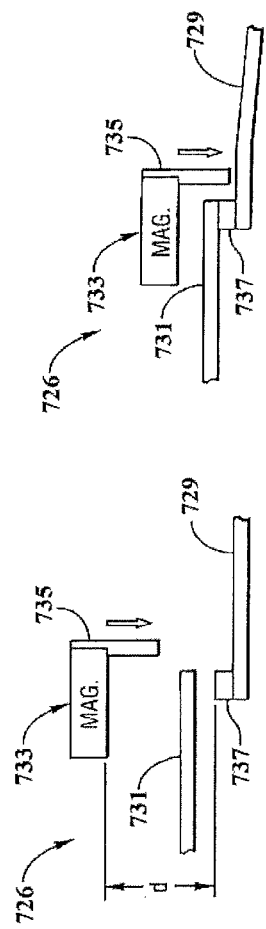
FIG. 36 is a partial fragmentary view of a switch used in the toothbrush shown in FIG. 35, the switch being shown in a first position.

FIGS. 36-37 illustrate one possible configuration for the switch 726. As seen in FIG. 36, the switch 726 comprises first and second contact plates 729, 731, and a magnet 733 having a limiting device 735. In FIG. 36, the switch 726 is in a first position, configured to prevent activation of the light sources 716. With no force being applied to the brush head portion 714, the magnet 733 is at a distance (d) from a magnetic contact 737 disposed on the first contact plate 729. The magnetic contact 37 is separated from the second contact plate 731, such that the two contact plates 729, 731 are not electrically connected.

As a force is applied to the brush head portion 714, the magnet 733 begins to move toward the two contact plates 729, 731, until the attraction from the magnet 733 causes the magnetic contact 737 to move toward the magnet 733. The magnetic contact 737 then makes contact with the second contact plate 731, thereby placing the switch 726 in a second position and activating the light sources 716 (see FIG. 37). The switch 26 can be configured so that the magnetic contact 737 is impelled toward the second contact plate 731, only after the first predetermined force has been applied to the brush head portion 714.

By adjusting various parameters such as the distance between the contact plates 729, 731, the strength of the magnet, and size of the limiting device 735, the predetermined force can be adjusted. Thus, the switch 726 can be configured to require different amounts of force to activate or stop the light sources 716.

The toothbrush body 712 has a generally cylindrical shape, though it could be made in almost any shape desired. For example, the translucent portion 742 could be beveled or faceted to create a prismatic affect as the emitted light passes through it. The minimal space required by the light source 716 and the control circuit 720, allows for design flexibility. Indeed, the present invention contemplates the use of more traditional toothbrush bodies, for example, ones having rectangular cross sections. In addition, the light source need not be an LED, but rather, may be a light bulb. As explained below in conjunction with other embodiments of the invention, the light source is not limited to only one particular kind—e.g., LED.

In addition to varying the arrangement of the light sources, the pattern of light generated by any set of light sources may be varied, depending on the configuration of the control circuit. For example, the toothbrush 710 may be configured with a control circuit that allows the LED to varying in intensity of the light emitted.

Figure 38:
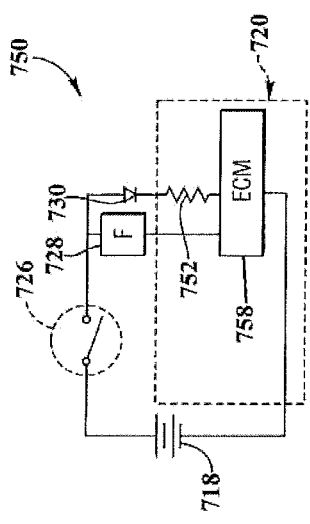
FIG. 38 is a simplified wiring schematic for the toothbrush shown in FIG. 35.

FIG. 38 shows a simple wiring schematic of a circuit 750 that can be used in the embodiment illustrated in FIG. 35. The circuit 750 includes the battery 718, the switch 726, the LED 730 and the control circuit 720. The control circuit 720, includes resistors 752 and an electronic control module (ECM) 758. Any suitable ECM may be used with a control circuit such as the control circuit 720, though a Philips 51 LPC is one type of ECM known to work in this application. As discussed above, activation of the light sources in a light emitting toothbrush, such as the toothbrush 710, may be controlled by a switch that includes a spring having a known stiffness. Alternatively, a load cell, such as the force sensor 728 may be used to sense the force being exerted on the brush head portion 714, and provide a brush force input signal to the ECM 758. This allows the ECM 758 to appropriately control the LED 730 based on the brush force input signal. It is readily understood by those skilled in the art that the circuit 50 shown in FIG. 8, represents but one of many circuits that can be used with the present invention. For example, a separate power supply, along with capacitive and additional resistive elements, can be added to the circuit to provide greater control of the power being delivered to the LED.

Figure 39:
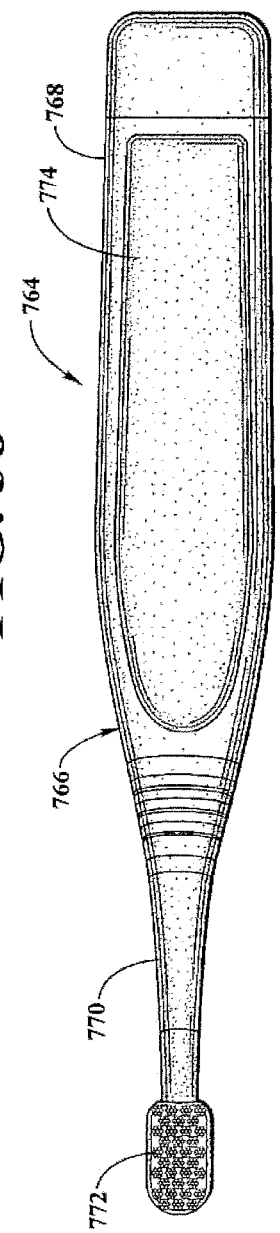
FIG. 39 is a perspective view of another embodiment of the invention where the sensor is a pressure sensing system including a one-piece compressible portion.
Figure 40:
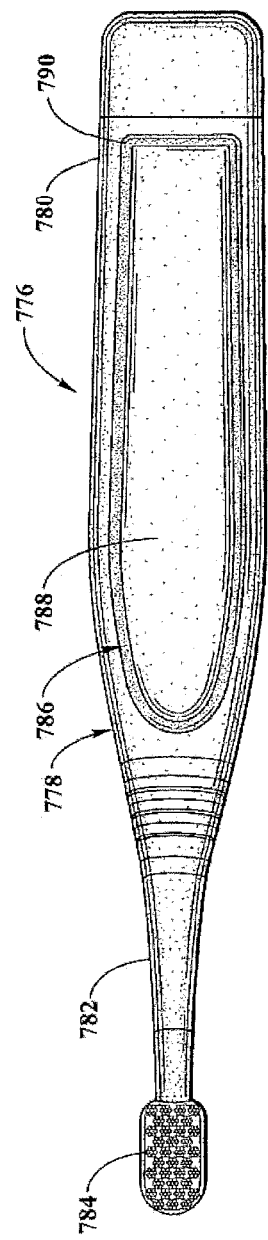
FIG. 40 is a perspective view of another embodiment of the invention where the sensor is a pressure sensing system including a two-piece compressible portion.

The embodiments described thus far have each included a switch that is actuated by a force applied to a brush head portion of a toothbrush body, such as the brush head portion 714 shown in FIG. 35. This configuration may be particularly useful when an object of the toothbrush is to train an operator to apply a proper amount of force during brushing. There are however, other ways in which a switch, such as the switch 726, may be actuated. For example, FIG. 39 shows a toothbrush 764 comprising a toothbrush body 766 that includes a handle portion 768 and a brush head portion 770 including bristles 772. The handle portion 768 includes a compressible portion 774 that is configured to be compressed when an operator uses the toothbrush 764. The compressible portion 774 comprises a non-rigid material, such as an elastomer. Alternatively, FIG. 40 shows a toothbrush 776 comprising a toothbrush body 778 including a handle portion 780 and a brush head portion 782, including bristles 784. The handle portion 780 includes a compressible portion 786 that comprises a rigid portion 788 surrounded by a non-rigid portion 790. This configuration may provide a compressible portion having greater stiffness than the compressible portion 774 shown in FIG. 39.

The embodiments shown in FIGS. 39 and 40 have compressible portions 774, 786 disposed on the same side of the toothbrush body as the bristles 772, 784. Of course, a compressible portion of a toothbrush handle portion may be located virtually anywhere on a toothbrush body, for example, on a side of the toothbrush body opposite the bristles. FIG. 41 shows a toothbrush 792 comprising a toothbrush body 794 including a handle portion 796 and a brush head portion 798, having bristles 800. The handle portion 796 includes a compressible portion 802 that is disposed on a side of the toothbrush 792 opposite the bristles 800. A switch 804 is disposed in relation to the compressible portion 802 such that compressing the compressible portion 802 actuates the switch 804. Actuating the switch 804 activates light source 806 which may be an LED as described above, or may be a light bulb. The switch 804 is shown in detail in FIGS. 42 and 43. The switch 804 includes a magnet 808, a magnetic plate 810, and a nonmagnetic plate 812. When a force (F) is exerted on the compressible portion 102, the force causes the magnet 808 to move in close proximity to the magnetic and nonmagnetic plates 810, 812. When the distance between the magnet 808 and the magnetic plate 810 drops below a fixed distance 814, the two plates 810, 812 contact each other (see FIG. 43), thereby activating the light sources 806.

Other types of switches may be used with a toothbrush having a compressible portion, two of which are shown in FIGS. 44 and 45. FIG. 44 shows a toothbrush 816 comprising a toothbrush body 818 including a handle portion 820 and a brush head portion 822, including bristles 824. The handle portion 818 includes a compressible portion 826. A switch 828 is disposed in relation to the compressible portion 826 such that compressing the compressible portion 826 actuates the switch 828, which activates light sources 830. The switch 828 comprises a magnet 832 and a Hall effect sensor 834. The magnet 832 is located beneath the compressible portion 826 such that application of a force (F) to the compressible portion 826 causes the distance between the magnet 832 and the Hall effect sensor 834 to decrease. When this distance is small enough, current flows through the Hall effect sensor 834 and the light sources 830 are activated.

Another type of switch that can be used in conjunction with a compressible portion on a toothbrush handle is shown in FIG. 45. A toothbrush 836 comprises a toothbrush body 838 including a handle portion 840 and a brush head portion 842, including bristles 844. A switch 846 comprises first and second contact plates 848, 850 disposed in relation to a compressible portion 852 of the handle portion 838 such that compressing the compressible portion 852 causes the two contact plates 848, 850 to move closer to each other until they contact, thereby actuating the switch 846 and activating light sources 854.

Figure 46:
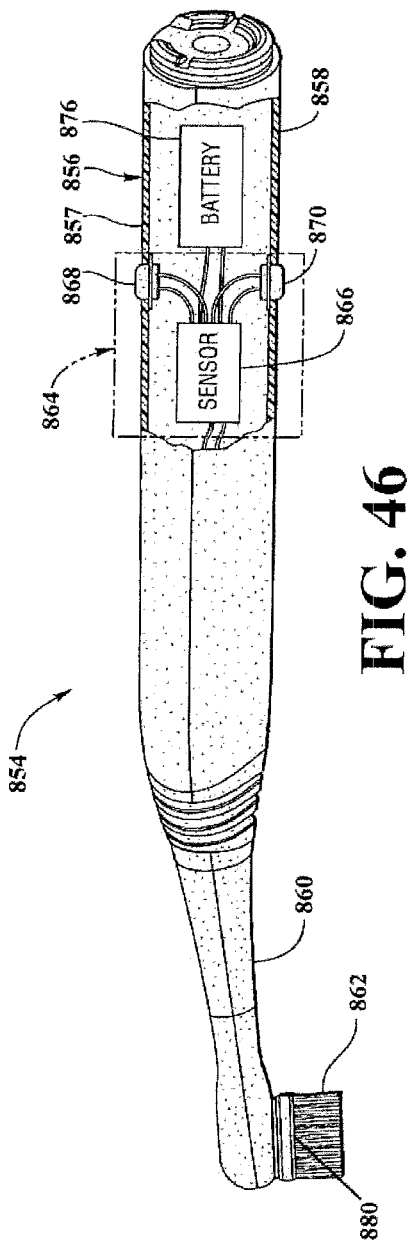
FIG. 46 is a partial fragmentary perspective view of another embodiment of the invention.
Figure 47:
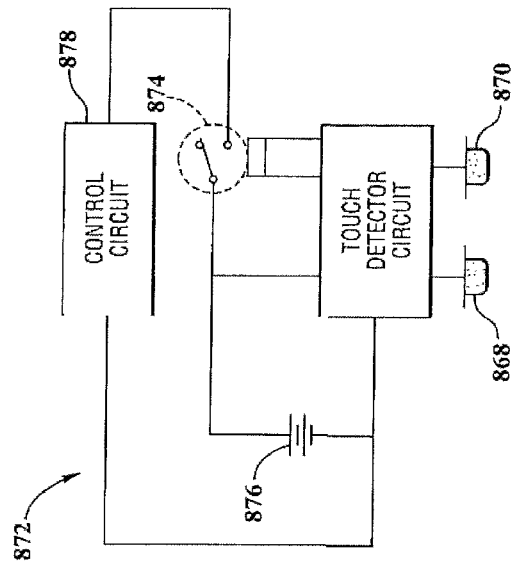
FIG. 47 is a simplified wiring schematic illustrating an electrical circuit that can be used with the toothbrush shown in FIG. 46.

FIG. 46 illustrates another way by which the light source in a toothbrush may be activated. A toothbrush 854 comprises a toothbrush body 856 including a handle portion 858 and a brush head portion 860, including bristles 862. The toothbrush 854 includes a sensing device 864 which comprises a capacitive sensor 866 attached to a pair of tactile sensors 868, 870 partially disposed on an external portion 871 of the toothbrush body 856. The presence of an operator's hand on the tactile sensors 868, 870 closes a switch 874 (see FIG. 47) that allows current to flow from a battery 876 to a control circuit 878 for controlling light source 880. The control circuit 878 may be configured similarly to the control circuit 750 shown in FIG. 38, or may have any configuration suitable to its use in the circuit 872. Thus, the mere presence of an operator's hand on the tactile sensors 868, 870 causes the light source 880 to emit light according to the programming and configuration of the control circuit 878.

Figure 48:
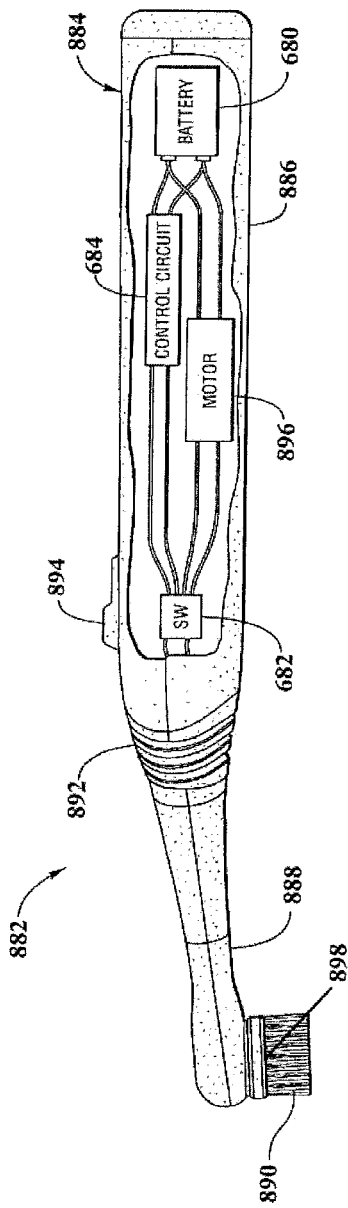
FIG. 48 is a partial fragmentary perspective view of another embodiment of the invention.

The embodiments thus far described include only manual—i.e., not motorized—toothbrushes. It is important to note that the present invention can be easily utilized with motorized electric toothbrushes as well. FIG. 48 shows a simplified descriptive view of a motorized electric toothbrush 882 in accordance with the present invention. The toothbrush 882 comprises a toothbrush body 884 including a handle portion 186 and a brush head portion 888. The brush head portion 888 includes a bristle head 890. A flexible portion 892 is provided that facilitates some movement of the brush head portion 888 when a force is applied to it. A first switch 894 is disposed on the handle portion 886, and is configured to connect a motor 896 and light source 898 to an electric source, such as battery 680. When engaged, the motor 896 drives the bristle head 890. The first switch 892 has a first position for preventing activation of the light source 898 and the motor 896, and a second position for facilitating automatic activation of the light source 898 and the motor 896.

A second switch 682 is disposed within the toothbrush body 884. The second switch 682 has a first position for preventing activation of the light sources 898 and the motor 896, and a second position for activating the light sources 898 and the motor 896 when the first switch is in the second position. The second switch 682 is placed in the second position when a predetermined force is applied to the brush head portion 888. The force may be applied during use, when the bristle head 890 is brought into contact with a user's teeth.

As in the previous embodiments, the predetermined force may be set by using a spring having a known stiffness. Specifically, such a spring may be used to resist a force applied to the brush head portion 888. In this way, the spring force will need to be at least partially overcome—i.e., a force equal to the predetermined force will need to be applied to the brush head portion 888—in order to place the second switch 682 in the second position.

Figure 19:
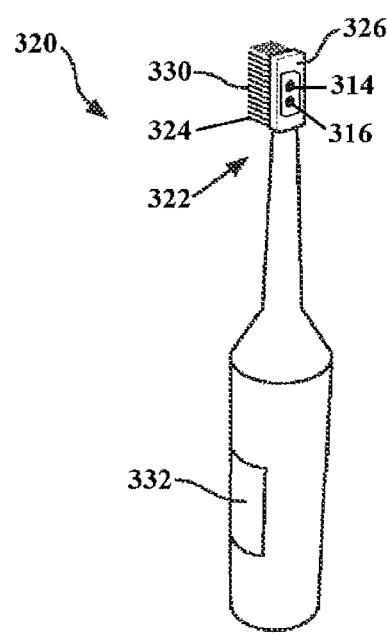
FIG. 19 shows an embodiment where the sensor is a photocell placed on the brush head of a toothbrush.
Figure 49:
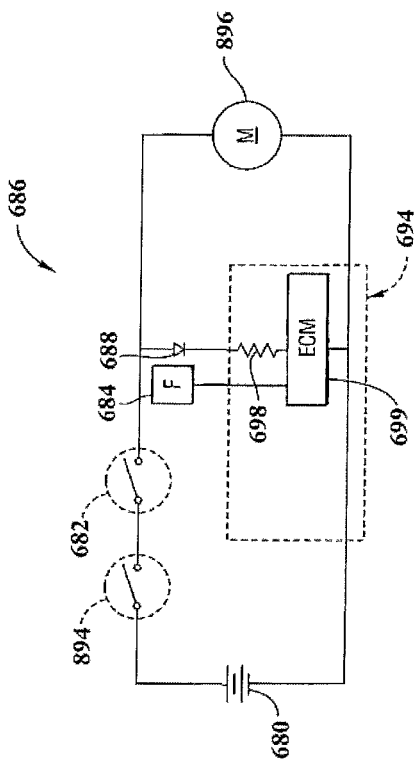
FIG. 49 is a simplified wiring schematic illustrating a circuit that can be used with the toothbrush shown in FIG. 48.
Figure 54:
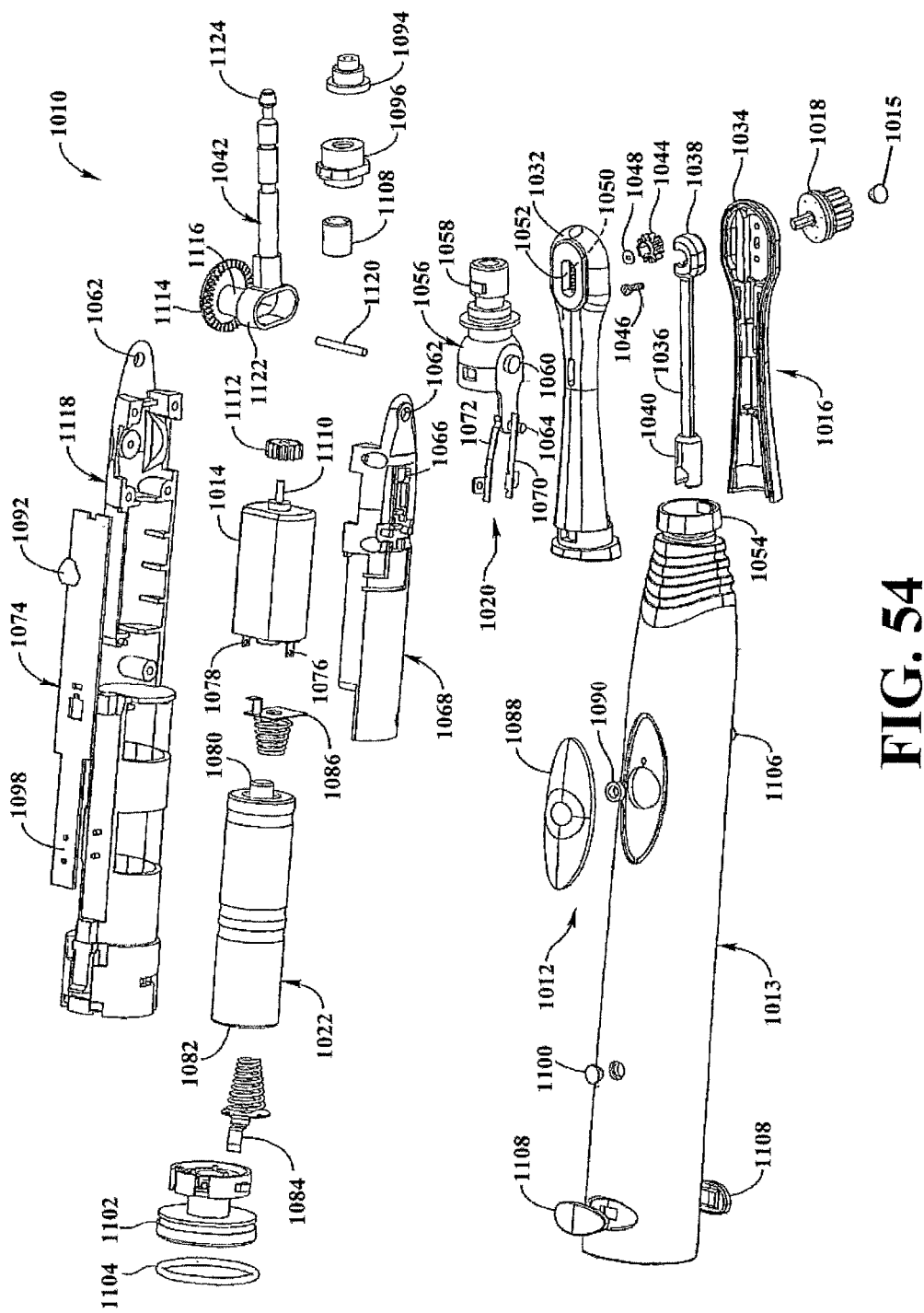
FIG. 54 shows an exploded view of the toothbrush shown in FIG. 50.

As an alternative to using a spring to control the predetermined force, a separate load cell, or force sensor 684 may be utilized (see FIG. 49). FIG. 49 shows a simple wiring schematic of a circuit 686 that can be used with a motorized toothbrush 882. As shown in FIG. 19, the light source 898 comprises LED 688 and is controlled by electrical circuitry, or a control circuit 694. The control circuit 694 includes resistor 698 and an electronic control module (ECM) 699.

Another useable pressure sensor is disclosed in US2003/0135940 to Lev et al. FIG. 50 shows a simplified descriptive side view of a motorized electric toothbrush 1010 in accordance with another embodiment of the present invention. A first switch 1012, located in a handle portion 1013, has a first or "off" position, and a second or "automatic" position, which places the toothbrush 1010 in an automatic mode. While the toothbrush 1010 is in the automatic mode, a LED 1015 is engaged only when a force (F) is exerted on a removable head portion 1016. This occurs when a bristle head 1018 sufficiently contacts an operator's teeth. As used here and throughout, the term "sufficiently contacts" implies a contact that is sufficient to cause a slight movement of at least a part of the removable head portion 1016 in the direction of the force. The force exerted by an operator (a user of the toothbrush) during normal brushing typically constitutes a sufficient contact. Thus, as the user begins brushing, a second switch 1020 automatically moves from a first position to a second position, an electric circuit is completed, and current flows from a battery 1022 to the LED driver 1024 that regulates and transmits power to LED 1015.

FIG. 51 shows a simple wiring schematic 1026 of a circuit for the toothbrush 1010 shown in FIG. 50. The LED driver 1024 is electrically connected between an electric source (the battery 1022) and the first switch 1012. When the first switch 1012 is in the first, or "off" position, the circuit 1028 is open and there is no voltage across LED driver 1024. When the first switch 1012 is in the second, or "automatic" position, control of the current flow to LED driver 1024 is transferred to the second switch 1020. While the toothbrush 1010 is in the automatic mode, the LED driver 1024 is only engaged when a force (such as (F) shown in FIG. 1) is applied to the bristle head 1018. An exception to this occurs when the toothbrush is programmed with a "delayed off" feature, discussed in more detail below. With the delayed off feature, the LED 1015 continues to operate for a short time after the force is removed from the bristle head 1018.

A number of alternative electrical circuits can be used with the present invention, two of which are shown in FIGS. 52 and 53. In FIG. 52, a wiring schematic 1026' shows a LED driver 1024' wired between a battery 1022' and a first switch 1012'. The first switch 1012' is a three position switch, having a first position in which circuits 1028', 1030 are both open. While the first switch 1012' is in the first position, no current can flow to the LED driver 1024', and the LED 1015 remains off. The first switch 1012' has a second position in which control of the current flow to LED driver 1024' is transferred to a second switch 1020'. When the second switch 1020' is in a first position, the circuit 1028' is open, and LED 1015 remains off. When a force is applied to a bristle head of the toothbrush, the second switch 1020' automatically moves to a second position such that the circuit 1028' is closed and the LED driver 1024' is engaged. The first switch 1012' also has a third position, in which the circuit 1030 is closed, and the toothbrush operates continuously.

Yet another wiring configuration is illustrated in the wiring schematic 1026" shown in FIG. 53. In this configuration, there is only one switch 1020" to control the flow of current from a battery 1022" to a LED driver 1024". When the switch 1020" is in a first position, circuit 1028" is open, thereby preventing the LED 1015 from turning on. When the switch 1020" is in a second position, the circuit 1028" is closed and current flows to LED driver 1024". As in the previous wiring configurations, the switch 1020" automatically moves from the first position to the second position when a force is applied to a bristle head of the toothbrush. As described above, each of the switches 1020, 1020', and 1020" "automatically" moves from a first position to a second position when the toothbrush is used by an operator. This implies that the user need not manually place the switch in the second position. Rather, the contact between the user's teeth and the bristle head automatically places the switch 1020, 1020', or 1020" in the second position.

Toothbrushes in accordance with these embodiments can be configured such that applying a force to the handle portion, rather than the bristle head, effects operation of the LED 1015 when it is in the automatic mode. For example, any of the switches 1020, 1020', 1020" can be positioned within the handle portion 1013 of the toothbrush 1010, shown in FIG. 1. In such a case, the switch may be automatically moved from the first position to the second position not by a force applied to the bristle head 1018, but rather, by a force applied to some part of the handle portion 1013. Embodiments of the invention utilizing this feature are described in more detail below.

Each of the wiring configurations shown in FIGS. 51-53 allow a toothbrush to be used in an automatic mode. That is, the toothbrush motor is engaged whenever a force is applied to that portion of the toothbrush that contains the switch 1020, 1020', or 1020". This facilitates ease of use, eliminating the need to operate a typical button switch after the bristle head is placed in the user's mouth. Another advantage of such a configuration is that a consumer can engage the toothbrush motor while the toothbrush is still packaged—i.e., prior to sale. In this way, the consumer can evaluate the operation of the toothbrush before purchase. Some prior art toothbrushes have a multi-function switch configured such that the consumer operates the toothbrush in the package using one activation mode, then operates the toothbrush during normal use in another activation mode. Such is not the case with the present invention, which affords the consumer the opportunity to activate the toothbrush in the package substantially as it will be activated during normal use. In today's consumer savvy environment, this feature provides another advantage over prior art toothbrushes.

FIG. 52 shows an exploded view of the electric toothbrush 1010 in accordance with another embodiment. The toothbrush 1010 includes the handle portion 1013 and the removable head portion 1016, which is shown having first and second housing elements 1032, 1034. The handle portion 1013 will usually be made from a polymeric material, and may be opaque, clear, or translucent. When the handle portion 1013 is clear or translucent, the toothbrush operator may see the movement of some of the toothbrush components when the motor 1014 is engaged. In addition, aesthetically pleasing features such as flashing lights (not shown) can be added to the components within the handle portion 1013 to augment the visual appearance. The removable head portion 1016 also includes a shaft 1036 that on one end has a pinion carrier 1038 and on the other a yoke 1040 configured to attach to a drive shaft 1042. A pinion 1044 is attached to the bristle head 1018 with a threaded fastener 1046 and a washer 1048. The pinion 1044 interfaces with a rack 1050, only a portion of which is visible through an opening 1052 in the first housing element 1032. Also included in the removable head portion 1016 is a snap ring 1054 that is manufactured in different colors such that removable brush heads belonging to different users can have different colored snap rings for easy identification.

This embodiment includes a rocker element 1056, which serves a number of functions. First, it contains clips 1058 (only one of which is visible in this view) that help secure the removable head portion 1016 to the handle portion 1013. In addition, trunnions 1060 (only one of which is visible), rotate in apertures 1062 thereby allowing the rocker element 1056 to pivot as force is applied to the removable head portion 1016. As the rocker element 1056 pivots about the trunnions 1060, a pin 1064 moves within a slot 1066. The slot 1066 is located in a first casing portion 1068 which also contains one of the apertures 1062 in which one of the trunnions 1060 rotates. Also located in the first casing portion 1068 is the first switch 1020, which comprises first and second contact plates 1070, 1072. As noted above, the first switch 1020 is optional (see FIG. 53), in which case, the toothbrush 1010 will always be in the automatic mode.

The contact plates 1070, 1072 are attached to the first casing portion 1068 in such a way that movement of the pin 1064 within the slot 1066 selectively causes the contact plates 1070, 1072 to contact each other and electrically connect. Electrically connecting the contact plates 1070, 1072 places the second switch 1020 is in the second position. This means that when the toothbrush 1010 is in the automatic mode of operation—i.e., when the first switch 1012 is in the second position-electrical connection of the contact plates 1070, 1072 engages the LED driver 1024 and causes LED 1015 to turn on. Thus, when the toothbrush 1010 is in the automatic mode of operation, sufficient contact of the bristle head 1018 with the user's teeth will cause a slight deflection of the removable head portion 1016. This in turn causes the rocker element 1056 to pivot on its trunnions 1060, thereby moving the pin 1064 within the slot 1066. When the pin 1064 causes electrical connection of the contact plates 1070, 1072, the LED driver 1024 is engaged without the user having to manually actuate any switches. Hence, turning on of LED 1015 is "automatic". The contact plate 1070 also acts like a spring, so that when the bristle head 1018 is not in contact with the user's teeth, the contact plate 1070 pushes against the pin 1064 and biases away from the contact plate 1072. Thus, the second switch 1020 returns to the first position when the bristle head 1018 is no longer in contact with the user's teeth.

Although the second switch 1020 returns to the first position when the bristle head 1018 is no longer in contact with the user's teeth, the LED driver 1024 may not immediately disengage. The action of the LED driver 1024 in this situation is dependent upon the configuration of a printed circuit (PC) board 1074. The PC board 1074 is an electronic controller that controls the electrical components of the toothbrush 1010. The PC board 1074 can be configured such that the LED driver 1024 continues to operate for a finite time after the second switch 1020 is moved from the second position to the first position. The finite time can be a very short interval, perhaps as little as a fraction of a second. This feature may be useful when the bristle head 1018 momentarily disengages contact with the user's teeth during normal brushing. During the short interval, until the time the bristle head 1018 is again in contact with the user's teeth, the LED driver 1024 will continue to run.

Although the wires are removed from this figure for clarity, the simple wiring involved in the present invention is easily understood by one skilled in the art. The PC board 1074 is wired to the motor 1014 at terminals 1076, 1078. Similarly, battery terminals 1080, 1082 are wired to the PC board 1074 through spring terminals 1084, 1086. The PC board 1074 can also be configured to control other functions in addition to the "delayed off" feature. For example, the PC board 1074 may not only control the delay of turning on/off LED 1015, but also the intensity of LED 1015 output. In addition, if indicator lights are used in conjunction with a transparent or translucent cover, as described above, the PC board 1074 can be configured to control the colors, duration, and sequence of such lights. In addition, the PC board 1074 can be configured to control sound elements, either alone, or in combination with the LED or indicator lights.

The first switch 1012 includes a switch cover 1088 and a switch button 1090. When an operator presses the switch cover 1088 the switch button 1090 contacts an electrical component 1092 of the PC board 1074, thereby placing the switch 1012 in the second position. Further pressing of the switch cover 1088 toggles the switch 1012 between the first and second positions. The handle portion 1013 also includes a drive shaft seal 1094 and a seal support 1096. The drive shaft seal 1094 helps to ensure that fluid does not reach the electrical components of the toothbrush 1010. The PC board 1074 includes an indicator LED 1098 that is visible to a user through a translucent cover 1100. The indicator LED 1098 may be used to indicate when the first switch 1012 is in the second position—i.e., when the toothbrush 1010 is in the automatic mode—or may be used to indicate when the battery 1022 is being charged. The battery 1022 is held in place by an end cap 1102 that is provided with an O-ring seal 1104 to further ensure that fluids do not reach the electrical components of the toothbrush 1010. Also included in the handle portion 1013 is a seat element 1106 that allows the toothbrush 1010 to be laid on a flat surface such that the bristle head 1018 remains pointing upward. This helps to keep the toothbrush 1010 stationary on a surface that is not level, and keeps the bristle head 1018 from contacting the surface. Aesthetic features 1108 are added to enhance the visual appeal of the toothbrush 1010.

The sensors described in these embodiments may be used in any type of dental hygiene implement. In the embodiments shown in FIGS. 54, 58-60, the dental hygiene implement is a motorized toothbrush. The reciprocating movement of the drive shaft 1042 is guided by a bushing 1108. The actual movement of the drive shaft 1042 resembles a typical slider crank mechanism. The motor 1014 has a rotating motor shaft 1110 that has a spur gear 1112 attached to it. The spur gear 1112 intermeshes with and rotates a ring gear 1114 that has integrally attached to it a cam 1116. The ring gear 1114 and the cam 1116 are held in a second casing portion 1118 with a pin 1120. The cam 1116 rotates within a cam follower 1122 that is attached to the drive shaft 1042. Thus, the rotational motion of the motor shaft 1110 is translated into reciprocating motion of the drive shaft 1042. When the removable head portion 1016 is attached to the handle portion 1013, the yoke 1040 connects to a head 1124 on the drive shaft 1042 such that the shaft 1036 reciprocates along with the drive shaft 1042. This in turn moves the pinion 1044 along the rack 1050 which causes the bristle head 1018 to translate and rotate simultaneously.

Figure 55:
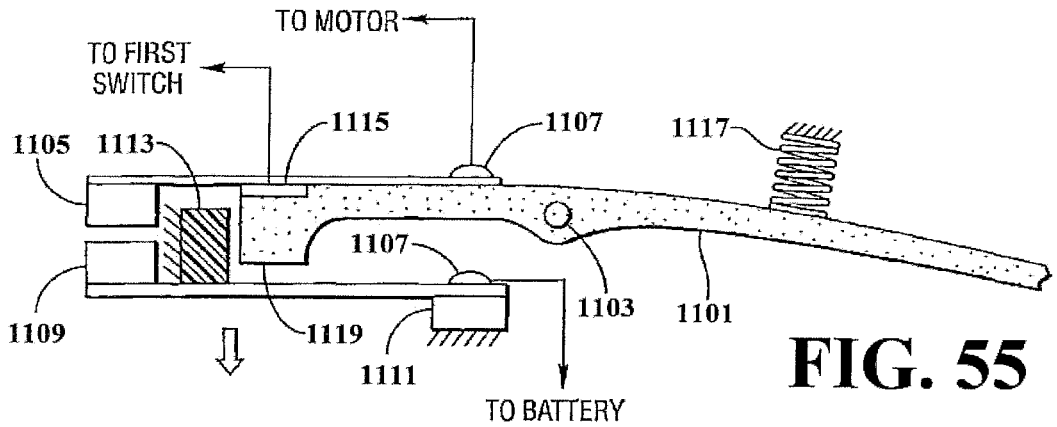
FIG. 55 shows an alternative configuration for the contact plates shown in FIG. 54.
Figure 56:
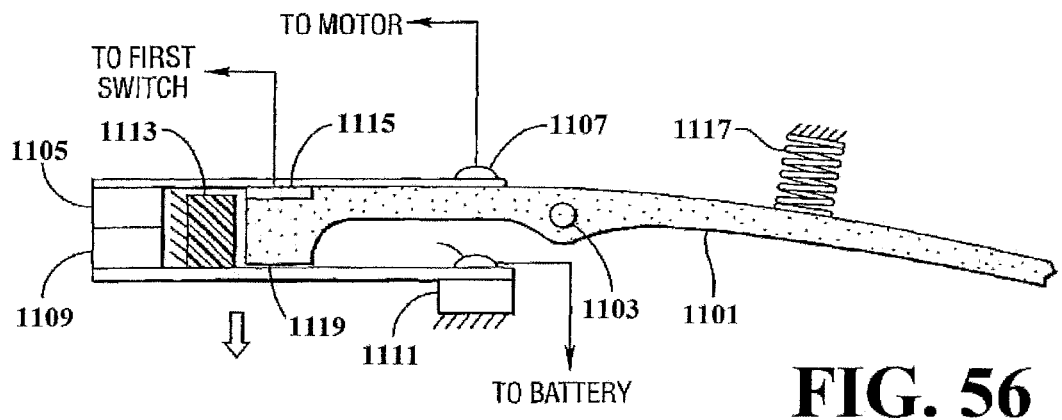
FIG. 56 shows the contact plates of FIG. 55 when a force is applied to the bristle head of the toothbrush.
Figure 57:
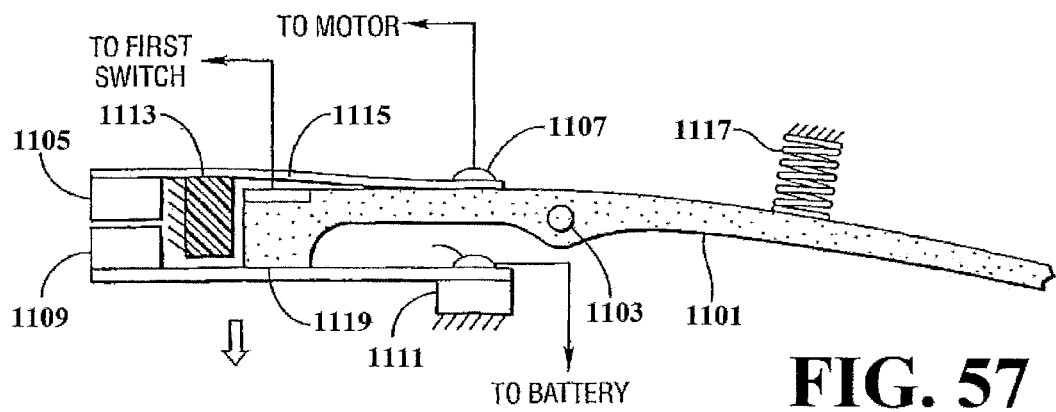
FIG. 57 shows the contact plates of FIG. 55 when the force applied to the bristle head exceeds a predetermined level.
Figures 58, 59:
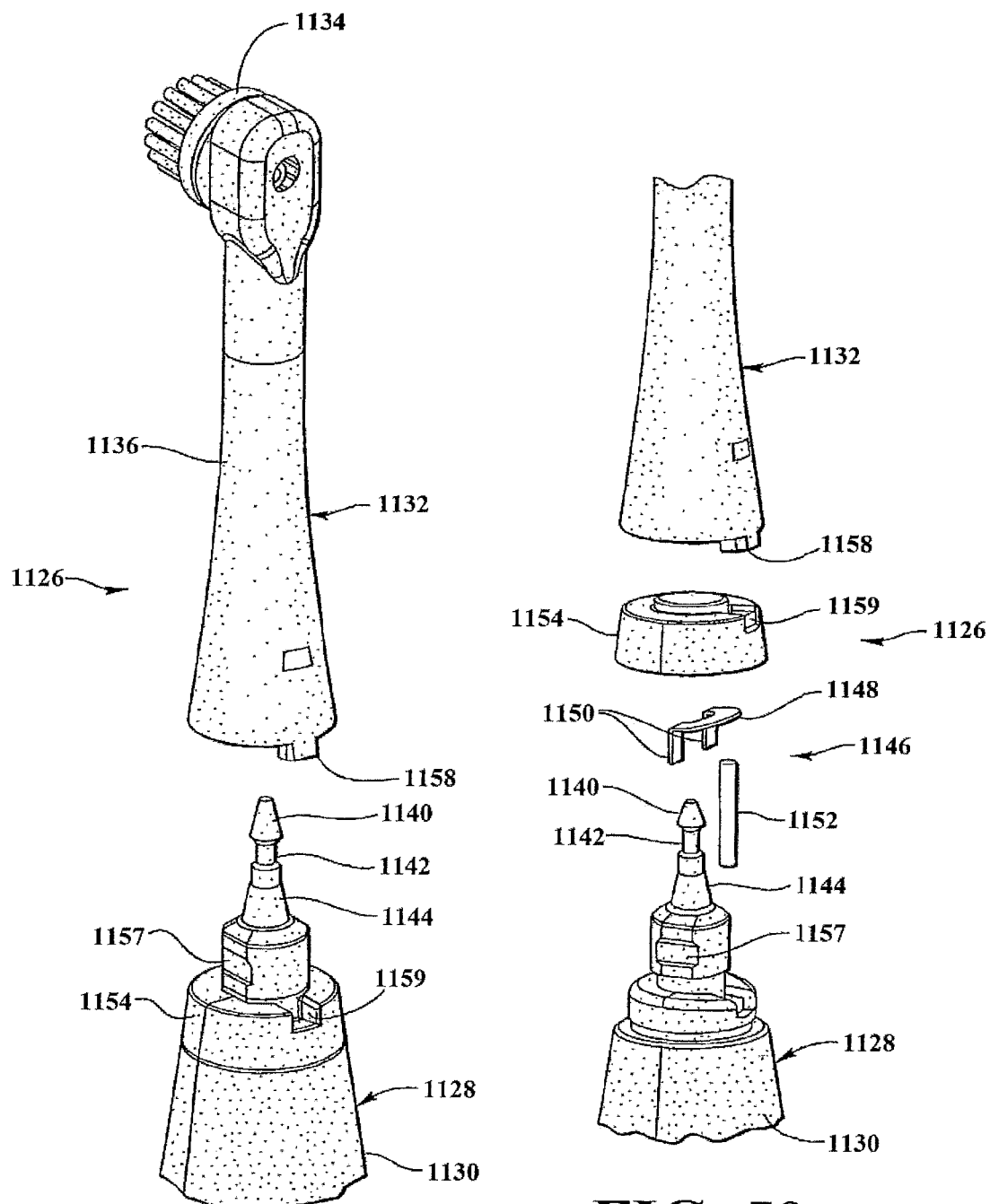
FIG. 58 shows a perspective view of a portion of a toothbrush in accordance with another embodiment of the invention where the sensor is a pressure sensor.
FIG. 59 shows a partially exploded perspective view of a portion of the toothbrush shown in FIG. 58.

An alternative configuration for the second switch 1020 is shown in FIGS. 55-57. This configuration provides for automatically stopping operation of LED 1015 on the toothbrush when the force on the bristle head in response to contact with the operator's teeth exceeds a predetermined level. FIG. 55 shows a portion of a rocker element 1101 that pivots about trunnions 1103 (only one of which is visible). A first contact plate 1105 is attached to the rocker element 1101 with a fastener 1107. A second contact plate 1109 is attached to a casing with another fastener 1107, a portion of the casing being shown as 1111. The casing has a stop block 1113 integrally formed therewith. The rocker element 1101 includes an electrically conductive contact pad 1115, which is an option that can be used when the first switch is a three-position switch (see FIG. 51). As illustrated in FIG. 55, the contact pad 1115 is electrically connected to the contact plate 1105, and when a three-position first switch is used, the contact pad 1115 will be wired to the first switch. Thus, when the first switch is in the third position, the toothbrush motor (such as 1014 shown in FIG. 51) will operate continuously. A spring 1117 is disposed between the rocker element 1101 and another portion of the casing (not shown), and biases the first contact plate 1105 away from the second contact plate 1109.

FIG. 56 is illustrative of automatic operation of the toothbrush. As the bristle head contacts the operator's teeth, the rocker element 1101 pivots about the trunnions 1103, thereby electrically connecting the contact plates 1105, 1109. As illustrated in FIGS. 55-57, the first contact plate 1105 is wired to the LED driver, and the second contact plate 1109 is wired to the battery. Thus, when the first switch is in the second position, or when there is only one switch (see FIG. 52), the electrical connection of the contact plates 1105, 1109 causes operation of LED 1015 on the toothbrush. If the operator continues to apply force to the bristle head beyond a predetermined level, the first contact plate 1105 will impinge on stop block 1113, but the rocker element 1101 will continue to pivot (see FIG. 57). A protrusion 1119 on the rocker element 1101 then contacts the second contact plate 1109 and pushes it away from the first contact plate 1105. This opens an electric circuit and turns off the LED 1015. Even if the toothbrush has a "continuous on" feature, the LED 1015 will still turn off when the first contact plate 1105 impinges on the stop block 1113. This is because the contact pad 1115 will no longer be in contact with the first contact plate 1105. The predetermined level at which the LED 1015 turns off can be easily adjusted by changing the spring 1117, the size of the stop block 1113, or the size of the protrusion 1119.

FIGS. 58-62 show portions of a toothbrush 1126 in accordance with another embodiment of the present invention. The toothbrush 1126 comprises a handle portion 1128 that includes a first housing 1130, and a removable head portion 1132 that includes a bristle head 1134 and a second housing 1136. This includes a shaft and a pinion which interfaces with a rack to drive the bristle head 1134. A yoke 1138, seen in FIGS. 60 and 61, connects to a head 1140 of a drive shaft 1142 which reciprocates when a motor (not shown) is engaged. A seal 1144 is disposed around the drive shaft 1142 to protect the electrical components of the toothbrush 1126 from contamination by fluids.

As in the previous embodiment, the toothbrush 1126 includes an automatic mode of operation. To facilitate the automatic mode of operation, the toothbrush 1126 has a first switch (not shown) that is configured as in the previous embodiment. A second switch 1146, seen in FIGS. 59 and 61, includes a contact plate 1148 having legs 1150 and a contact rod 1152. The contact plate 1148 and the contact rod 1152 are disposed within the handle portion 1128 and are covered by a seal 1154. Similar to the contact plates 1070, 1072 used in the first embodiment, the contact plate 1148 and the contact rod 1152 are wired to a PC board (not shown).

Figure 61:
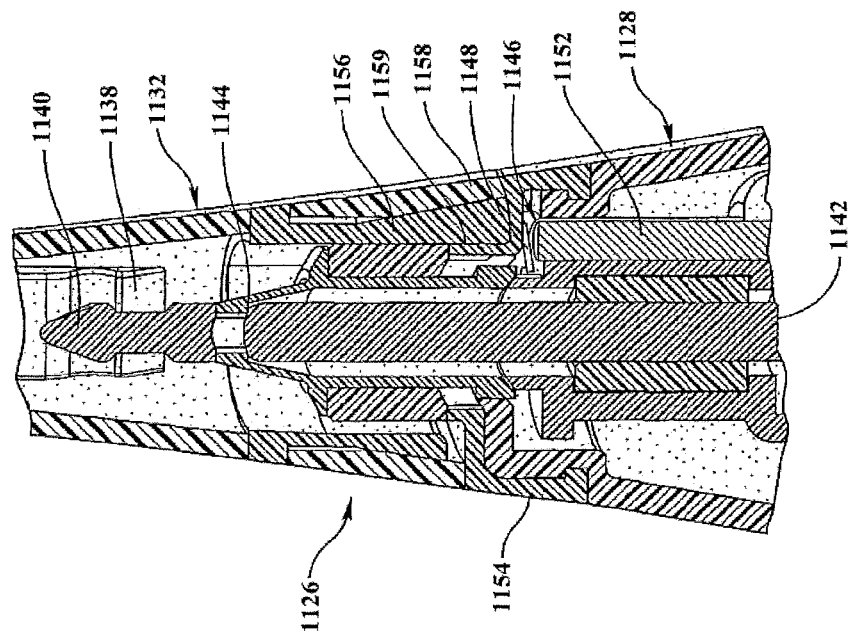
FIG. 61 shows another sectional view of the toothbrush shown in FIG. 58.
Figure 60:
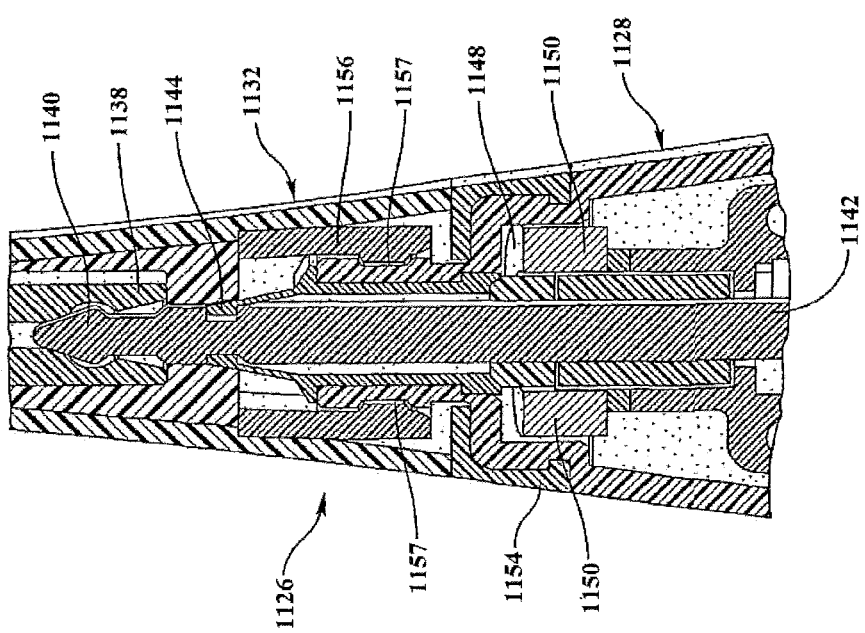
FIG. 60 shows a sectional view of a portion of the toothbrush shown in FIG. 58.

The method by which the removable head portion 1132 attaches to the handle portion 1128 is also different from the first embodiment. An adaptor 1156, seen in FIGS. 60 and 61, is located inside the housing 1136 of the removable head portion 1132, and snaps into recesses 1157 in the handle portion 1128, (see FIG. 60). This attachment allows the removable head portion 1132 to be securely attached to the handle portion 1128, and at the same time allows the head portion 1132 to pivot in relation to the handle portion 1128 when the bristle head 1134 sufficiently contacts the user's teeth. As consistently used throughout the various embodiments, "sufficiently contacts" merely implies a contact that is sufficient to cause a slight movement of at least a part of the removable head portion 1132.

As the removable head portion 1132 undergoes the slight pivoting motion caused by contact with the user's teeth, a projection 1158 pushes into a notch 1159 in the seal 1154. As the projection 1158 moves into the notch 1159, it pushes the seal 1154 against the contact plate 1148. With the legs 1150 held stationary, the contact plate 1148 deflects in a spring-like fashion until it contacts the contact rod 1152. This places the second switch 1146 in the second position, and enables LED 1015 to turn on when it is in the automatic mode. The spring-like deflection of the contact plate 1148 also acts to bias it away from the contact rod 1152, to turn off LED 1015 when the bristle head is not in contact with the user's teeth. As in the previous embodiment, the PC board can be configured such that the LED 1015 does not disengage immediately, but rather, remains engaged for a short time after the bristle head is removed from the user's teeth.

Although both of the embodiments described above have a two-position first switch, as illustrated schematically in FIG. 51, a three-position switch (as shown in FIG. 52) can be used. Alternatively, the first switch can be eliminated, as in FIG. 53, so that the toothbrush is always in the automatic mode. The two toothbrushes described above include removable brush head portions; however, either can be made with a non-removable brush head portion. In fact, any of the embodiments described herein can be made with a non-removable brush head portion, which may be particularly well suited to disposable toothbrush designs.

Figures 62, 63:
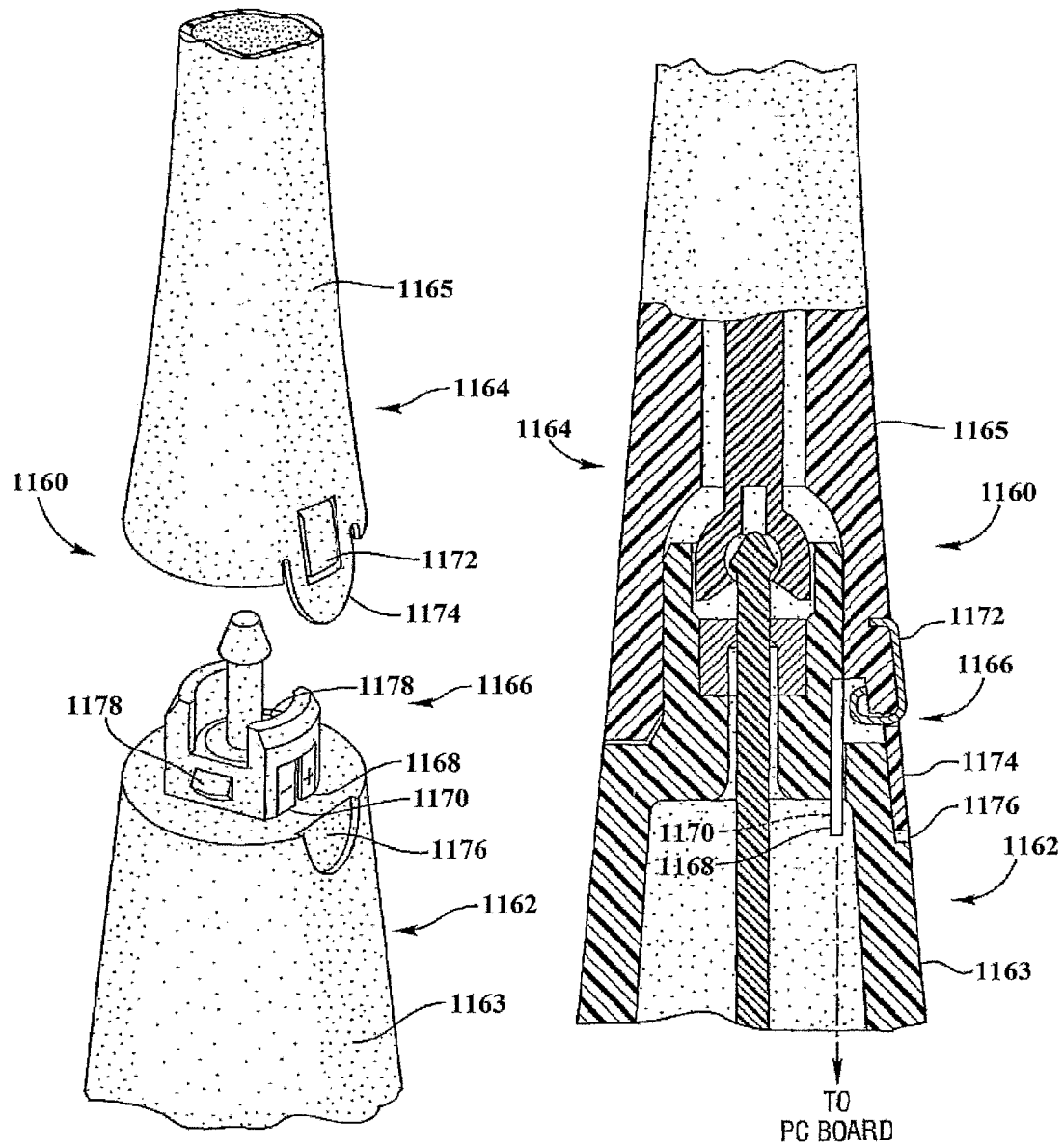
FIG. 62 shows a partially exploded perspective view of a portion of a toothbrush in accordance with another embodiment of the invention where the sensor is a pressure sensor.
FIG. 63 shows a sectional view of a portion of the toothbrush shown in FIG. 62.

Portions of a third embodiment of the present invention are shown in FIGS. 62 and 63. In this embodiment, a toothbrush 1160 includes a handle portion 1162 that has a first housing 1163, and a removable head portion 1164 that has a second housing 1165 and a bristle head (not shown). As in the previous embodiments, the toothbrush 1160 includes a first switch (not shown) having a first, or "off" position that prevents the LED 1015 from turning on, and a second, or "automatic" position that allows the LED 1015 to function in an automatic mode. A second switch 1166 comprises first and second stationary contact plates 1168, 1170, and a third contact plate 1172. The removable head portion 1164 includes a projection 1174 that fits into a notch 1176 in the first housing 1163 of the handle portion 1162.

The removable head portion 1164 attaches to the handle portion 1162 at snaps 1178. This connection allows the removable head portion 1164 be securely attached to the handle portion 1162, and at the same time allows the head portion 1164 to pivot in relation to the handle portion 1162 when a bristle head (not shown) sufficiently contacts the user's teeth. As the removable head portion 1164 pivots, the third contact plate 1172 contacts, and thereby electrically connects, the stationary contact plates 1168, 1170. This places the second switch 1166 in the second position, and causes LED 1015 to turn on when it is in the automatic mode. The projection 1174 also acts as a spring as the removable head portion 1164 pivots, thereby keeping the third plate 1172 biased away from the stationary plates 1168, 1170 when the bristle head is not in contact with the user's teeth.

In each of the embodiments described above, the second switch was automatically moved from the first position to the second position when a force was applied to the bristle head. Specifically, a force on the bristle head in response to its contact with the operator's teeth caused the second switch to move to the second position and the motor was engaged. As previously noted however, the second switch need not be activated by a force on the bristle head. Rather, the second, switch may be located such that it is automatically placed in the second position when the user grips the handle portion. One way to accomplish this is to provide the handle portion with a compressible portion, and dispose the second switch in relation to the compressible portion such that compressing the compressible portion moves the second switch from the first position to the second position, thereby turning on LED 1015.

FIGS. 64 and 65 illustrate two embodiments of toothbrushes having differently configured handle portions. FIG. 64 illustrates a toothbrush 1180 having a compressible portion 1182. The compressible portion 1182 can be molded integrally with toothbrush handle housing 1184, or may be attached in a separate operation. The compressible portion 1182 is typically made from a polymeric material that deflects when the toothbrush is used in a normal brushing operation. The handle housing 1184 may be configured with a relatively small, or a relatively large compressible portion. In this embodiment, the compressible portion 1182 occupies a large area of the handle housing 1184, thereby helping to ensure that users having different gripping preferences will be accommodated.

FIG. 65 illustrates a toothbrush 1186 having a compressible portion 1188 located in a housing 1190 of a handle portion 1192. In this embodiment, the compressible portion 1188 includes a rigid portion 1194 and a non-rigid portion 1196. When a user compresses the compressible portion 1188, the non-rigid portion deflects, thereby moving a switch (not shown) from a first position to a second position to turn on LED 1015. Having a two-piece compressible portion such as 1188 not only changes the look, but also the feel of the toothbrush when compared to a toothbrush having a single piece compressible portion. Thus, the designer is allowed flexibility with regard to both form and function.

FIG. 66 shows a toothbrush 1198 that includes a removable head portion 1200 and a handle portion 1202. The handle portion 1202 includes a first switch 1204 which has first and second positions for respectively turning off and on LED 1015. The handle portion 1202 includes a handle housing 1206 that has a compressible portion 1208. Disposed within the handle portion 1202 in close proximity to the compressible portion 1208, is a second switch 1210, shown in detail in FIG. 67.

The switch 1210 shown in FIG. 67 includes a magnet 1212, a magnetic plate 1214, and a non-magnetic plate 1216. When the first switch 1204 is in the second position, motorized operation of the toothbrush 1198 occurs only when a force (F) is exerted on the compressible portion 1208. This force causes the magnet 1212 to move in close proximity to the magnetic and non-magnetic plates 1214, 1216. When the distance between the magnet 1212 and the magnetic plate 1214 drops below a fixed distance 1218, the two plates 1214, 1216 contact each other (see FIG. 68). When the first switch 1204 is in the second position, and the two plates 1214, 1216 contact each other, the LED driver is engaged (not shown), thereby causing LED 1215 to turn on.

Figure 69:
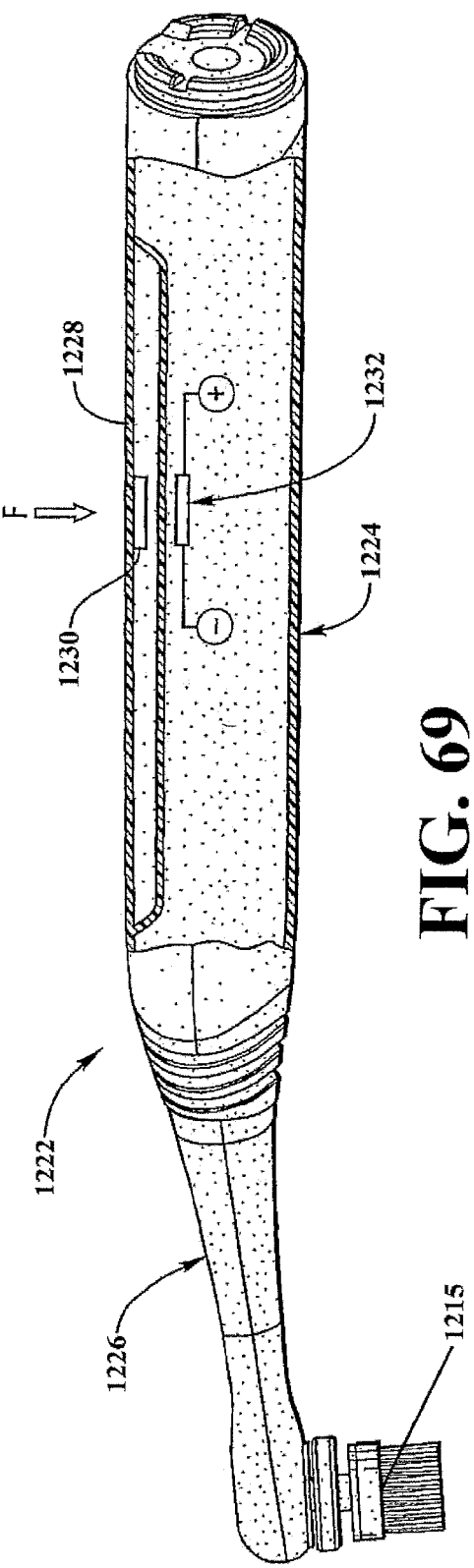
FIG. 69 shows a simplified descriptive view of a toothbrush in accordance with another embodiment of the present invention.

FIG. 69 shows another embodiment of a toothbrush 1222. The toothbrush 1222 has a handle portion 1224 and a removable head portion 1226. The handle portion 1224 includes a compressible portion 1228. In this embodiment, toothbrush 1222 only has one switch 1229 which comprises a magnet 1230 and a Hall effect sensor 1232. The magnet 1230 is located beneath the compressible portion 1228, and application of force (F) to the compressible portion 1228 causes the distance between the magnet 1230 and the Hall effect sensor 1232 to decrease. When this distance is small enough, current flows through the Hall effect sensor 1232, and LED 1215 turns on.

In another embodiment of the invention, the sensor is a moisture detection—uses a moisture sensor to detect a highly moist environment such as the mouth. This can be accomplished through various types of moisture sensors for example; capacitive or chilled mirror dew point sensors. Such a sensor is disclosed in US 2009/0087813 to Cai et al, and hereby incorporated by reference.

These motion sensor embodiments of the present invention relate to a bio-active oral care instrument, having the ability to active an LED automatically, when the instrument or a portion thereof is exposed to one or more conditions, such as the ambient electrical conductivity, existing in the oral environment. Other conditions and combinations of conditions, such as pH, temperature, solute concentrations, etc. could likewise be detected and used as the basis for automatic operation. Furthermore, aspects of these embodiments are illustrated in the remainder of this disclosure with reference to an electric motorized toothbrush, although it is understood that the operation of any number of oral care instruments, together with the associated advantageous features and/or beneficial effects described herein, could likewise be achieved. Other oral care instruments, for example, include those used in dental drilling, polishing, and grinding;

oral suction instruments, oral surgical instruments; and other instruments used in the oral cavity which are powered by motorized devices and especially electrical devices.

The representative toothbrush illustrated in FIG. 70 has a handle 901 and a head 905 carrying one or more cleaning elements, which are depicted in FIG. 70 as a plurality of bristles 906. Also illustrated is a neck 904 located between, and connecting, handle 901 and head 905. The bristles 906, as shown, form clusters that are anchored to the head 905 and provide a profiled brushing surface with their free ends. Other bristle configurations are of course possible, as well as removable/exchangeable bristle clusters. Different types of cleaning elements (e.g., elastomeric wipers, nodules, pointed structures, etc.) may also be carried on head 905 instead of, or in addition to, bristles.

The neck 904 is provided with electrical conducting elements 907 (e.g., an anode and a cathode) that are exposed to the exterior surface of the toothbrush. In other embodiments, the electrical conducting elements 907 can be located on the head 905, for example on the surface opposite that which carries bristles 906. The use of electrical conducting elements 907 on different parts of the toothbrush is also possible. A plurality of electrical conducting elements 907 can also be incorporated in various positions to activate the instrument in the event that sufficient electrical conductivity is established between any given pair(s) of electrical conducting elements 907 located at any desired position. Integrated in the region of the neck 904 which is adjacent to the head 905 is a LED driver 911 that is operably connected to LED 960. The motorized device 911 is operably connected, via electrical connections 934 in the neck 904 to a power source (e.g., a battery, not shown), which may be accommodated in the handle 901. Operably connected and operably connectable refer to the ability of the electrical connections, or other elements, to readily form an electrical circuit (e.g., when a switch is depressed or when a power source is connected or installed). Operably connected and operably connectable may also refer to the ability of mechanical components to be connected to one another in such a manner as to allow or provide for physical movement of one or more elements. The LED driver may be alternatively incorporated in the head 905 or handle 901 of the toothbrush. In representative embodiments, electrical connections 934 may be metal wire or electrically conductive plastic tracks.

In particular embodiments where the toothbrush uses a vibratory device, it will have a vibratory element which can be in the form of an eccentric, which produces mechanical vibrations and can be rotated about an axis located in the longitudinal direction of the toothbrush. Alternatively, instead of an eccentric which can be driven in rotation, it would also be possible to have a vibratory element which can be driven in a translational manner. Otherwise, the bristle-carrying head 905 can be arranged such that it can be moved in relation to the neck 904 in order for the latter, in the case of vibrations produced by motorized device 911, to move in relation to the rest of the toothbrush.

As shown, also accommodated in the handle 901 is a sheath or sleeve 920 which extends in the longitudinal direction of the handle 901 and is made of electrically conductive material. In the representative embodiment shown, both the handle 901 and the sleeve 920 are open to the rear, thus forming a cavity 921 which can be closed from the rear by a closure part 922 and into which it is possible to insert a battery, such as a commercially available, non-rechargeable cylindrical battery, with a defined voltage (e.g. 1.5 V), as the power or voltage source for LED driver 911.

It would also be possible, however, for a button cell or for a rechargeable storage batter to be used as the power source. An external power source such as a conventional electrical outlet or a combination of voltage sources may be employed as the power source.

Also shown in the particular illustrative embodiment of FIG. 70 is a spring contact 929 for a positive pole of a battery (not shown), which is fitted in the sleeve 920, on a transverse wall 92S, and is electrically connected to the LED driver 911 through the electrical connections 934 and switch 932, which is installed in the sleeve 920 and can be actuated from the outside of the handle 901. Switch 932 may also be, for example, a magnetic switch pulse switch or a pulse switch arranged on a printed circuit board with further electronic components that store the switching state. In other embodiments, closure part 922 can itself act as a switch, such that electrical contact between the power source and LED driver 911 is established or interrupted by turning closure part 922 to alter the position of contact surface 922b relative to the negative pole of a battery.

It is to be appreciated, as discussed in greater detail below, that switch 932 is not necessary due to the ability of the toothbrush to turn on automatically when in the user's mouth. In some embodiments, therefore, the toothbrush can be "switchless" or "buttonless."

Switch 932 may be depressed or adjusted by the user to effect a number of operating modes. For example, in "on" and "off" positions or settings, electrical communication or an electrical circuit between the power source and LED driver 911 may be continually established or continually interrupted, respectively. In the former case, for example, the electrical conducting elements 907 may be bypassed to allow continuous operation of motorized device 911, regardless of the presence of a conductive medium between electrical conducting elements 907. Switch 932 may also have a position corresponding to conditional completion of the electrical circuit.

Also as shown in FIG. 70, the closure part 922 is provided with a threaded stub 922a made of an electrically conductive material, which may be the same material (e.g., a metal such as copper or a conductive plastic) used for the electrical conducting elements 907, electrical connections 934, spring contact 929, and/or sleeve 920. Closure part 922 can be screwed into the handle 901 and/or into the sleeve 920 by way of said threaded stub 922a. The threaded stub 922a is provided with a contact surface 922b which, with the closure part 922 screwed in, comes into abutment against the negative pole of a battery (not shown) when inserted into the sleeve 920. During operation of the motorized toothbrush, this negative pole is electrically connected to LED driver 911 via the threaded stub 922a, the sleeve 920 itself, and electrical connections 934 connecting sleeve 920 to LED driver 911. It would also be possible, instead of through the use of sleeve 920, for the power from the negative pole to be transmitted in some other way, for example using wires or electrically conductive plastic tracks. Instead of the rear closure part 922 being screwed to the handle 901, it would, of course, also be possible to have some other type of releasable connection (e.g. plug-in connection, bayonet connection, etc.) and a corresponding configuration of the contact part interacting with the negative pole of the battery.

One representative characteristic of the oral environment which differs significantly from the surrounding or ambient "non-use" environment is electrical conductivity, which increases directionally with the concentration of electrolytes in the surrounding medium (e.g., saliva). In some embodiments, this "non-use" environment may even include rinsing or submersing the portion of the instrument that is normally placed in the mouth (e.g., the head 905 of the toothbrush) in water (e.g., for pre-wetting or rinsing purposes), since the electrical conductivity of saliva is higher than that of water. This difference can thus be utilized to allow the instrument to "detect" when it is being used and thereby operate in an automatic mode.

Additionally, the combination of water, saliva, and dentifrice (e.g., toothpaste or other ingredient that is generated in the mouth during use of the instrument) often affords even a significantly higher electrical conductivity than saliva alone. This is due to the generation of ions, often in large concentrations, from typical oral care products, including tooth fluoridating, whitening, and/or remineralization products which contain or form aqueous cations, such as sodium ($Na^+$), potassium ($K^+$), calcium ($Ca^{+2}$), magnesium ($Mg^{+2}$), iron ($Fe^{+3}$), etc. and anions, such as phosphate ($PO_4^{-3}$), diphosphate ($P_2O_7^{-4}$), carbonate ($CO_3^{-2}$), fluoride ($F^-$), chloride ($Cl^-$), etc.

In view of the above, the increase in electrical conductivity surrounding a portion of the toothbrush, e.g., head 905 or head 905 and neck 904, when placed in the mouth, can be used to complete an electrical circuit, together with an electrical power or voltage source such as an external electrical outlet or an internal battery to activate LED driver 911, causing LED 960 to turn on.

In an "auto" position or setting, LED driver 911 is powered by the power source only in the event that sufficient electrical conductivity (e.g., a threshold level of conductivity, or sufficiently low resistance) exists between electrical conducting elements 907 in the neck 904. The required electrical conductivity, as needed for the "conditional completion" of the electrical circuit to power motorized device it, may be provided, for example, by an electrolyte solution containing ions (e.g., calcium, phosphate, fluoride, or peroxide ions) such as that generated from a combination of saliva, water, and toothpaste existing in the oral environment during use. When the electrical conductivity between conducting elements 907 is no longer present, the electrical circuit is incomplete, thereby deactivating LED driver 911 and LED 960. Thus, in an "auto" or automatic operating mode, LED driver 911 and LED 960 will not be activated when the toothbrush is stored since air is the medium between electrical conducting elements 907. According to some embodiments, when the brush is being rinsed outside the mouth, the water between electrical conducting elements 907 will not have sufficient electrical conductivity to activate LED driver 911 and LED 960.

According to some embodiments, it may be desired to require that the electrolyte solution (e.g., saliva or a water/saliva/toothpaste mixture), to which the toothbrush is exposed during use, have a threshold (or minimum) level of conductivity before LED driver 911 is activated. This threshold level of conductivity, for example, may be based on a threshold (or minimum) current needed to activate LED driver 911. This threshold conductivity, required to automatically turn on the toothbrush, may be associated with the electrical conductivity of saliva alone or an electrolyte solution having a relatively higher conductivity (e.g., an aqueous solution of toothpaste) or lower (e.g., a mixture of saliva and water) conductivity. For example, the threshold conductivity may be associated with a standard or model electrolyte solution designed to mimic the electrical conductivity of saliva having one or more specified, additional concentrations of dissolved ions such as calcium phosphate, fluoride, peroxide, and other ions or mixtures of ions.

In this manner, the automatic functioning of the oral care instrument can be made more or less sensitive to the particular conditions or conditions associated with the environment in which the instrument is used (i.e., the "use" condition(s) required to activate the instrument). It is also possible that the sensitivity of the instrument can be adjusted by, set by, or tailored to, the user (e.g., to avoid either activation of the instrument during "non-use" conditions or non-activation during "use" conditions) and thereby ensure effective functioning of the instrument in automatic mode.

In certain embodiments, the change in conductivity of the medium between electrical conducting elements 907 is measured by a sensing device 938, such as a circuit board 938 or other suitable sensing device, connected to electrical conducting elements 907 by electrical connections 940. In certain embodiments, sensing device 938 may measure the drop in resistance between conducting elements 907. When the conductivity change reaches a preset value as detected by sensing device 938, switch 932 may be activated so as to complete the electrical circuit to power LED driver 911. In such an embodiment, the electrical circuit need not include the electrolyte solution between conducting elements 907. That is, the electrolyte solution is used as a trigger to activate switch 932 by way of sensing device 938, but does not actually form part of the electrical circuit that powers LED driver 911.

In other embodiments, switch 932 could be activated based on the differential change in conductivity between conducting elements 907. It is to be appreciated that the level of electrolyte in the medium will vary from person to person, and/or may vary based on the formula of the oral care solution used. In such embodiments, these variations will not affect the current level delivered to the motor. Thus, for example, when using a sensitivity type toothpaste product having 5% $KNO_3$, the toothbrush would not operate differently than when used with a standard toothpaste product having a lower ionic strength.

According to other embodiments, when exposed to a solution with a threshold level of electrical conductivity, LED driver 911 and, therefore, the LED 960 itself may be set or adjusted (e.g., using a timer) to activate for a minimum duration. This ensures that the toothbrush or other instrument will function for at least enough time to effectively accomplish a given task (e.g., tooth cleaning and/or whitening). This also promotes continuous operation, even if contact between the instrument and the electrolyte solution is temporarily lost, for example, when a toothbrush is temporarily removed from the mouth during brushing. The minimum duration for activation of the LED (e.g., two minutes) may be fixed or may otherwise be set or adjusted according to a user's preferences.

As discussed above, the ability of a dental instrument to "activate" (e.g., to turn on a motor) when exposed to the environment in which it is used (e.g., an electrolyte solution in the mouth) can obviate the need for an "on/off" switch or button, creating a simplified operation. Another embodiment of a motorized device activated when conducting elements 907 are exposed to an electrolyte solution is shown in FIG. 71. A reservoir 944 is provided in handle 901 for storing an active agent. Conducting elements 907 are used to activate a pump 946, which causes a predetermined quantity of the active agent to be delivered from reservoir 944 through a channel 948 leading to a plurality of outlets 950 located in head 905. An exemplary delivery system for an active agent is described in U.S. application Ser. No. 11/457,086, the entire disclosure of which is incorporated herein. Other examples of oral care instruments that can activate an LED upon exposure of conducting elements 907 to an electrolyte solution will become readily apparent to those skilled in the art, given the benefit of this disclosure.

Figure 72:
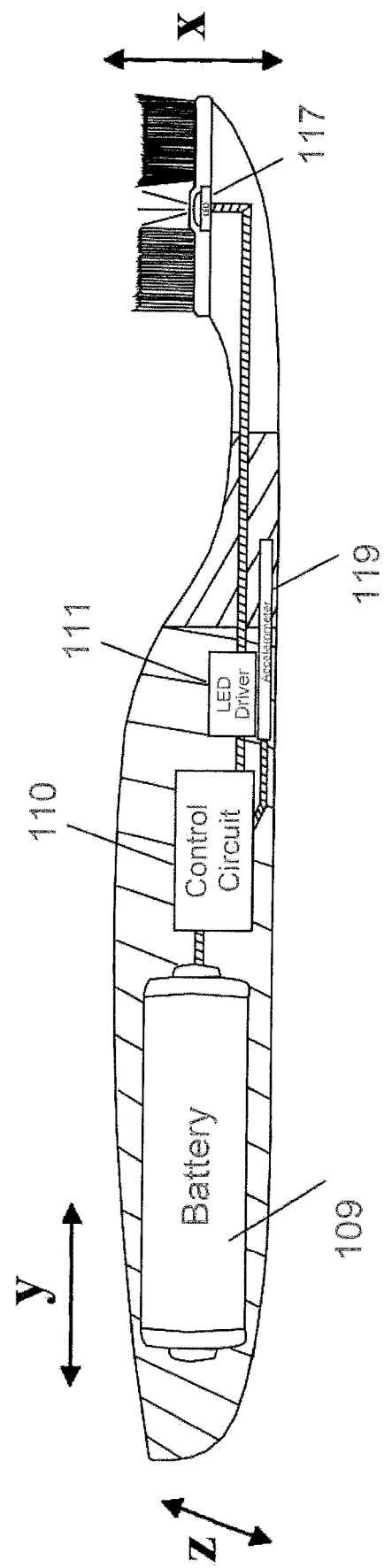
FIG. 72 shows an embodiment of the present invention wherein the sensor is an accelerometer.

In yet another embodiment, the sensor may be one or more accelerometers within a dental hygiene implement that detect the user's brushing movement and compare it to previously stored brushing profiles to determine if the brush is in use or not. In the embodiment shown in FIG. 72, the dental hygiene implement is a toothbrush 100 with an accelerometer 119 connected to a control circuit 110. If the accelerometer 119 detects that the brush is in use, the control circuit 110 will signal to the LED driver 111 to maintain the light source 117 until the brushing time has expired. The brushing time is adjustable, and may be set by either the manufacturer or the user. If the brushing time has expired, then the light source 117 will turn off and an indicator (not shown) will signal to the user that brushing has been completed. In one embodiment, the indicator is an additional LED light located on the handle of the toothbrush. In another embodiment, the indicator is an audio signal relayed to the user.

One or more accelerometers may be installed in the toothbrush to measure the x-, y- and z-axis of the toothbrush at any given moment while the user is brushing his teeth. The control circuit may signal to the LED driver to turn on the light source when the accelerometers indicate that the toothbrush is in an orientation within a predetermined range. In another embodiment of the invention, there is a time delay between the moment the accelerometers indicate that the toothbrush is in a brushing orientation and the moment where the control circuit signals to the LED driver to turn on the light source.

In yet another embodiment, the user may pre-program his brushing pattern to the control circuit such that the LED driver will only activate the light source only when the control circuit recognizes the user's brushing pattern. In one embodiment, the control circuit signals to the LED driver to activate the light source for a predetermined amount of time set by either the manufacturer or user. Alternatively, in another embodiment, the control circuit may continuously signal to the LED driver to keep the light source on until the accelerometer indicates that the user is no longer brushing.

In other embodiments of the invention, the sensor is a combination of two or more of these sensor types.

Embodiments may further include a mechanism for alerting a user that LED 117 is about to be powered on. In some embodiments, toothbrush 100 may include a light emitter to signal the status of LED 117. The light emitter may be controlled in such a matter as to alert the user that the light is about to come on to full radiant power, through a gradual increase in power from 0% of full power, up to 100% of full power, for a period of between 0.5 seconds to 2 seconds, using a linear, exponential, geometric, logarithmic or other non-linear radiant power curve before a complete and full power is achieved on the light emitting toothbrush. In one embodiment, the light emitter may be an additional LED on toothbrush 100. In various embodiments, the light emitter may operate by providing a short burst of low frequency light pulses or flashes, using a rectangular, saw-tooth, pulsed, sinusoidal or other types of common periodic waveforms, in the range of 2-10 Hertz at partial or full power, for a period of between about 0.5 seconds to about 5 seconds before full power is achieved on the LED in the toothbrush 100. In combination or in the alternative, light emitter may also emit color-coded signals dependent on the amount of power supplied to LED 117. The color of the light emitter may gradually change from a first color to at least a second color as power to the LED 117 gradually increases. Alternatively, the color of the light emitter may change in discrete increments from a first color to at least a second color as LED 117 gradually increases in power. In a preferred embodiment the warning light and the therapeutic light are the same. The advantage of a 0.5-5 second ramp-up of the therapeutic light is that the bright light will trigger the human eye's natural aversion/blink reflex before it poses a hazard to the user. Thus, such a feature acts as a secondary, redundant safety feature in conjunction with the above disclosed eye protection sensors. The light source radiant power may be controlled by adjusting the analog current or through use of pulse width modulation (PWM).

Other mechanisms may be used to alert a user of the power status of LED 117. In one embodiment, a vibrator such as a motor may be incorporated into toothbrush 100. The vibrator may operate by providing a series of pulsed vibration for a short duration of time, such as between about 0.5 seconds to about 2 seconds, before LED 117 is fully powered. In another embodiment, the vibrator may provide a constant vibration with increasing intensity as the power of LED 117 gradually increases. The vibrator may be a motor used to drive the brush head of a motorized toothbrush. In yet another embodiment, toothbrush 100 may further include an auditory device for emitting a sound to alert a user of the power status of LED 117. For example, the speaker may provide a pulsating beep for a short duration to indicate that LED 117 is about to emit at full power.

One or more mechanisms may be included with toothbrush 100 to indicate the upcoming power status of LED 117. These and other identifiers may be useful as a safety feature to prevent a user from inadvertently looking directly at LED 117 while it is fully powered.

It may be possible to inadvertently and momentarily break the interlock safety circuit during normal brushing while the brush head is still in the mouth. For example, when using the current loop embodiment of FIGS. 1-8, such a momentary break may happen when the brush head is moved from one side of the mouth to the other, breaking the biological circuit between the brush head and the brush handle. This break could cause the light to momentarily shut-off while still in use, creating an unintentional flicker. To prevent this situation, the micro-controller circuit can be programmed to introduce a shut-off delay such that the circuit does not shut-off until the interlock circuit has been broken for more than a predefined period of time. In one embodiment, the predefined period of time is between about 0.1 to about 0.5 seconds. In another embodiment, the break could cause the light to dim for a short period, such as between about 0.1 to about 0.5 seconds before actually shutting off. If the interlock circuit is reengaged during this dimmed time, the light goes back to full power without the need to alert the user.

Figure 73:
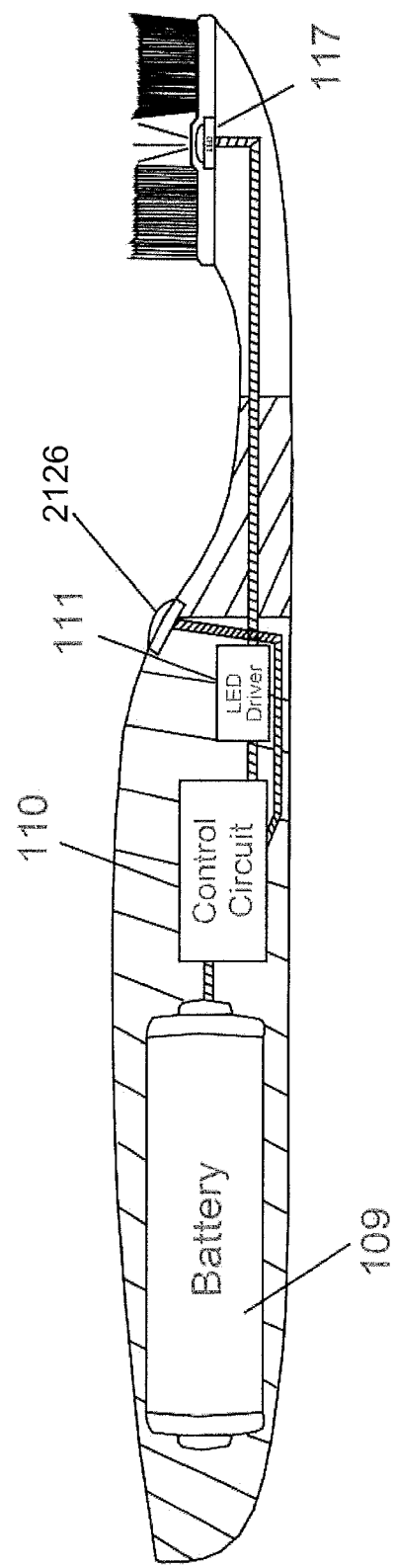
FIG. 73 shows an embodiment of a toothbrush including a fingerprint sensing module.

These embodiments and others may further include a fingerprint module mounted on the handle to verify if the user is authorized. In particular, to keep children from playing with the device and defeating the safety measures that prevent the LED from coming on unless it is in a user's mouth, the fingerprint module may be included to only allow the LED to come on if a finger of a hand of an authorized adult is detected. The fingerprint reader may be a button or simply a surface. Various fingerprint sensors are known and can be used in combination with the embodiments disclosed. The fingerprint reader preferably includes a memory for storage of fingerprint data of authorized users and sufficient processing capability to compare stored fingerprint data with new data read as a user attempts to use the toothbrush. Alternatively, the toothbrush could include a data link as in the "internet of things" to compare the fingerprint data remotely and return a "match" or "no match" decision. In the embodiment shown in FIG. 73, the dental hygiene implement is a toothbrush 100 having a LED 117 at the brush head connected to a LED driver 111 located in the handle of the toothbrush. The control circuit 110 is connected to the LED driver 111 as well as a battery 109 and a fingerprint module 2126. The fingerprint module 2126 may be initialized to recognize a user, with such information stored in the control circuit 110. Subsequent uses of the toothbrush will require the user to verify his identity by placing his fingerprint on the fingerprint module 2126.

In one embodiment, if the user's identity is correct, then the user may proceed to insert the brush head into his mouth and the LED will turn on in response to the installed sensor (not shown). If the user's identity is incorrect, then the LED will not turn on even if the installed sensor detects pressure, moisture, capacitance, etc. In another embodiment, the toothbrush 100 may further include an on/off switch where the fingerprint module and LED remain completely inactive in the "off" setting. In yet another embodiment, the toothbrush 100 further includes an additional indicator to indicate whether the user is authorized. This indicator may be a visual light source that turns green when a user is authorized to use the brush. A red light source may be activated to indicate that the user is not authorized to use the toothbrush. Other types of indicators may be used, such as an audio indicator.

Figure 74:
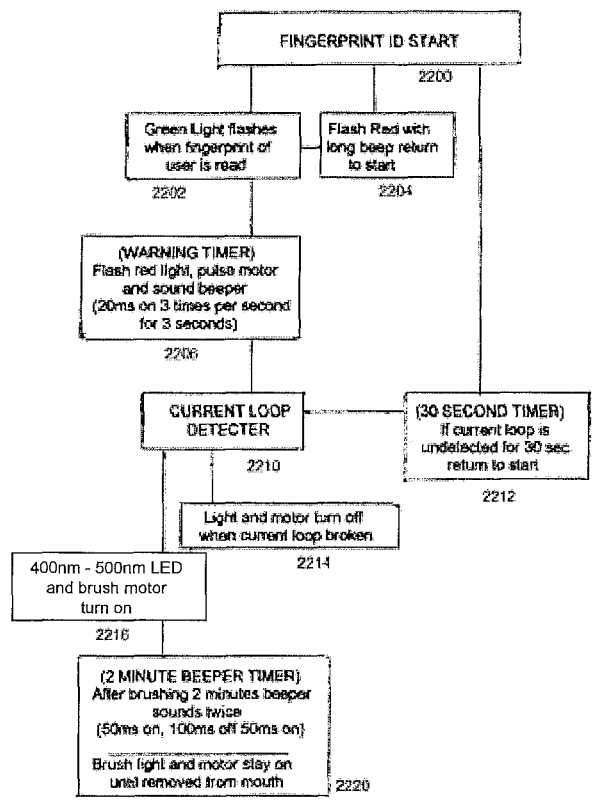
FIG. 74 is a flowchart illustrating an embodiment of steps for use of a toothbrush having a fingerprint sensing module and a plurality of LED status indicators.

FIG. 74 illustrates one example of a toothbrush having a fingerprint module for authorization. The fingerprint module may be presented as a start button for the user to depress and hold for a short duration 2200. The duration may be between about 1 to about 3 seconds. An indicator may be provided to alert the user that the fingerprint has been read. In the example provided, a green light flashes once the fingerprint is read 2202. If an error occurs, the light may flash red and emit a sound 2204. Once the fingerprint is authorized, the light emitter may flash red and provide a pulsing vibration and sound to alert the user that the LED is about to become fully powered 2206. Simultaneously, the current loop detector determines whether the toothbrush is being inserted into the mouth (or a detector using any of the mechanisms as described in the embodiments above) 2210. If no current is detected after a preset time interval, then the toothbrush shuts off 2212. If a current is detected, then the LED and brush motor are activated 2216. A timer indicates when a sufficient duration of brushing has been reached by beeping an auditory signal to the user 2220. Once the user removes the brush from the mouth, the current loop is broken 2214. If the toothbrush remains out of mouth for 30 seconds, the system turns off and the fingerprint reader will need to be used to reactivate system 2212.

Figure 75:
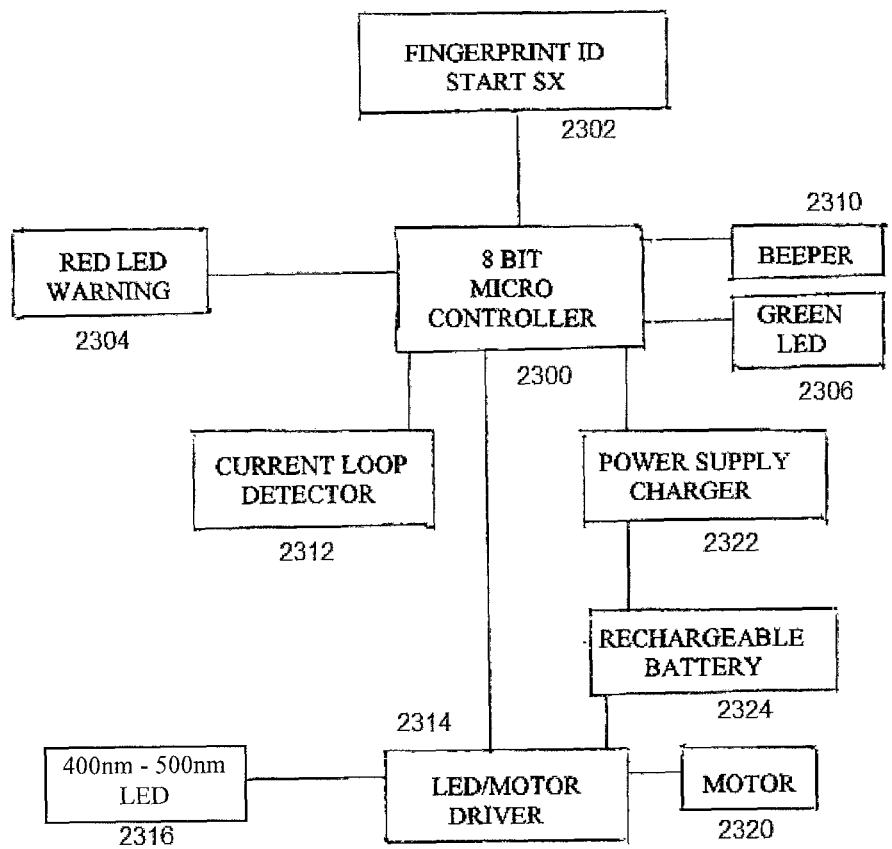
FIG. 75 is a simplified schematic of an embodiment of a toothbrush including a fingerprint sensing module and a plurality of LED status indicators.

FIG. 75 illustrates one embodiment of how the fingerprint module and status indicators are connected with other components of the toothbrush using a circuit block diagram. The microcontroller 2300 is wired to the following components: the fingerprint module 2302, a red LED 2304, a green LED 2306, a beeper 2310, a current loop detector 2312, a LED/motor driver 2314, and a power supply 2322/2324. The LED/motor driver 2314 is responsible for activating the UV LED 2316 and the brush head motor 2320. LED/motor driver 2314 is also connected to the power supply 2322/2324.

Of course, the fingerprint module and warning feature may be used with non-motorized toothbrushes.

In another embodiment, the fingerprint module 2126 acts as the sensor for toothbrush 100. The LED will turn on once an authorized user places his fingerprint over the module. In this embodiment, it is intended for the user to place the fingerprint over the module only after the brush head is inserted within the mouth.

The primary purpose of an interlock sensor is to protect the user's eyes from sudden and unexpected bright light. However, conventional designs allow only for either an on or off state, which presents two problems. First, the sudden transition from an "off" state to an "on" state could happen inadvertently, such as when the user applies pressure to the brush head with one hand whilst holding the handle in the other hand. This could expose the user's eyes to an unexpected bright burst of light. Second, the sudden transition from an "on" state to an "off" state could cause flickering during normal operation, such as when the brush head is moved from one side of the mouth to the other side of the mouth. This could shut off the light even when the brush is still in the user mouth. Furthermore, if a ramp-up sequence is implemented, this sequence could be triggered at the wrong time when the brush head is still inside the user's mouth.

These inadvertent problems could occur regardless of the types of sensor used. To address these problems, the microcontroller (for example Renesas RL78/G12 manufactured by Renesas Electronics) which regulates the functions of the light emitter can be programmed to implement four operating states with respect to light activation according to the state transition diagram depicted in FIG. 76.

Figure 76:
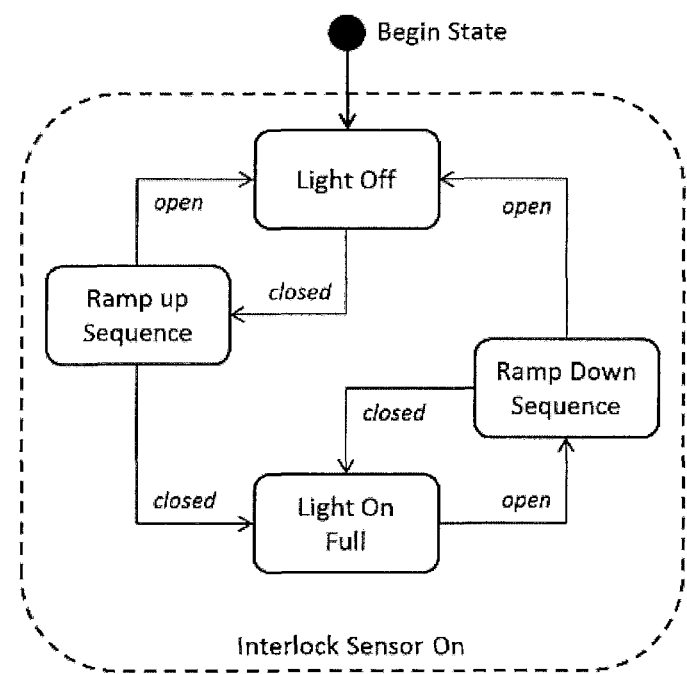
FIG. 76 illustrates an interlock sensor software state transition diagram.
Figure 77:
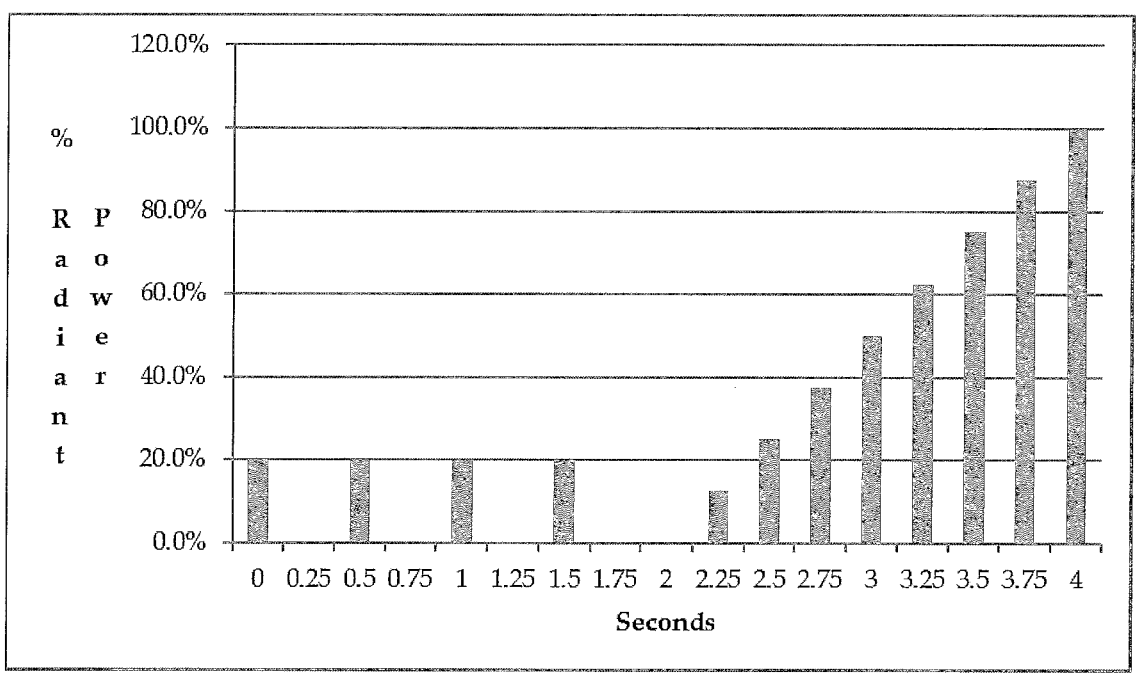
FIG. 77 illustrates one example of a ramp-up sequence in accordance with one embodiment.

The state transitions correspond to events detected by any of the various sensors which can be used to detect an "in-the-mouth" condition. FIG. 76 provides one example of the events that can trigger these transitions. The beginning state for the toothbrush is "light off." If a "closed" event is detected, the state transitions to the Ramp-up sequence. In one embodiment, the ramp up state can only occur immediately after the "light off" state and the interlock sensor detects a closed "in mouth" condition. For example, in one embodiment, the brush head LED emits between 1 and 10 perceptible light pulses of between 0.1 to 0.5 seconds each at between 10% and 50% radiant power output with interludes of between 0.1 to 0.5 seconds between each pulse. Then the power would gradually and continuously increase from no power to full power for a further 0.5 to 5 seconds as depicted in the example FIG. 77. Other types on ramp-up sequences can be programmed into the microcontroller, and this example is not limiting. The important characteristics of a ramp up sequence include a gradual increase in radiant power to allow ample time for the user to respond or trigger the eyes natural aversion reflex, such as blinking, if the light source is too bright for the eyes. While the flashing option can be used, the ramp-up without flashing is preferred.

Returning to FIG. 76, if the circuit opens during the ramp up sequence the interlock state reverts to light off. If it remains closed at the end of the ramp up sequence the interlock state transitions to "light on full." The light on full state occurs after the successful completion of a ramp-up sequence, or the unsuccessful exit of a ramp-down sequence and the sensor circuit is in a closed condition. Radiant power output is at or near its optimum operating threshold. This state can exit through a circuit open event, in which case the state transitions to the ramp-down sequence. The purpose of the ramp down sequence is to prevent flickering during normal brushing. The ramp down sequence can only occur after the "light on full" state. When the interlock circuit is opened, the brush head light switches to between 10% to 50% radiant output power for a transition period of between 0.1 to 1 second. If the circuit is closed at any time during the ramp down sequence, the state immediately reverts back to the "light on full" state. If the ramp down transition period completes without a "closed" event and the interlock circuit is still open then the interlock state transitions back to "light off."

The above software relating to the ramp-up/ramp-down sequence can operate with any type of interlock sensor that can detect an "in-the-mouth" condition to control the light source of a light emitting toothbrush. Such a toothbrush will have at least a portion of the handle and/or at least a portion of the distal end being equipped with a sensor to determine whenever the distal end is outside the environment of the mouth and permits activation of the source of light only when the source of light is inside the mouth of the user, the sensor selected from the group consisting of: a current signal loop which detects current flowing from the brush handle through the body of the user to the brush head, a capacitive sensor which detects current flowing through the body of a user when the brush head or bristles are in contact with the mouth and the handle is in contact with the hand; a capacitive displacement sensor that senses change of position of any conductive target such as the human body; an inductive sensor that uses an inductance loop to measure the proximity of conductors such as the human body; a passive thermal infrared that detects the warmth of the human mouth; a photoelectric sensor that detects reflected IR light emitted and absorbed by the sensor itself, a light sensor that is triggered by darkness inside the mouth; a light sensor that detects the reflection of light from a second light source on the brush when the brush is activated; an ultrasonic and active sonar sensors that uses echo location to detect the confines of the mouth; a magnetic detector that detects the proximity of metals such as the hemoglobin present in blood; a pressure sensor under the brush head that detects movement and pressure of the brush head being pressed against the teeth; a pressure sensor in the neck that detects torque and tension in the neck of the brush due to brushing action; a cantilever switch sensor under the brush head that detects movement and pressure of the brush head being pressed against the teeth; a cantilever switch sensor in the neck that detects torque and tension in the neck of the brush due to brushing action; a moisture sensor to detect a highly moist environment such as the mouth; and a combination of two or more of these sensor types. These sensors and their corresponding events which would alter the state of the safety interlock are depicted in FIG. 78.

In another embodiment, the toothbrush employing the current signal loop interlock for safe application of a visible therapeutic light source may be modified to further operate as an ionic toothbrush in combination with the therapeutic properties of blue and/or violet light. Experiments have shown that visible therapeutic light primarily affects Black Pigmented Bacteria (BPB) which are predominantly periodontal pathogenic strains such as; *Fusobacterium Nucleatum, Fusobacterium* Periodonticum, *Porphyromonas Gingivalis, Prevotella Intermedia, Prevotella Melaninogenica*, and *Prevotella Nigrescens*. However, visible therapeutic light has little or no effect on non-pigmented bacteria or those strains with a low concentration of pigment. Many pathogenic bacteria fall into this category; for example, *Streptococcus Mutans, Streptococcus Sobrinus* and *Lactobacillus* species are common and significant contributors to tooth decay (dental caries). Visible therapeutic light is ineffective against these and other non-pigmented strains.

The combination of visible therapeutic light and ionic action provides two non-mechanical modalities that disrupt pathogenic bacteria in places where a traditional toothbrush can't reach, such as between the teeth or below the gum line. This combination therapy enables all of the pathogenic strains to be targeted including periodontal pathogens as wells as pathogens that cause dental caries (tooth decay). Moreover, while visible therapeutic light can attrite and weaken the biofilm by killing *Fusobacterium Nucleatum*, a key plaque aggregant, an ionic toothbrush can also disaggregate bacteria using electrostatic forces. Therefore, visible therapeutic light and ionic action work in combination to disrupt the cohesion of plaque biofilm providing better cleaning results than either technology applied individually or separately.

Figure 79:
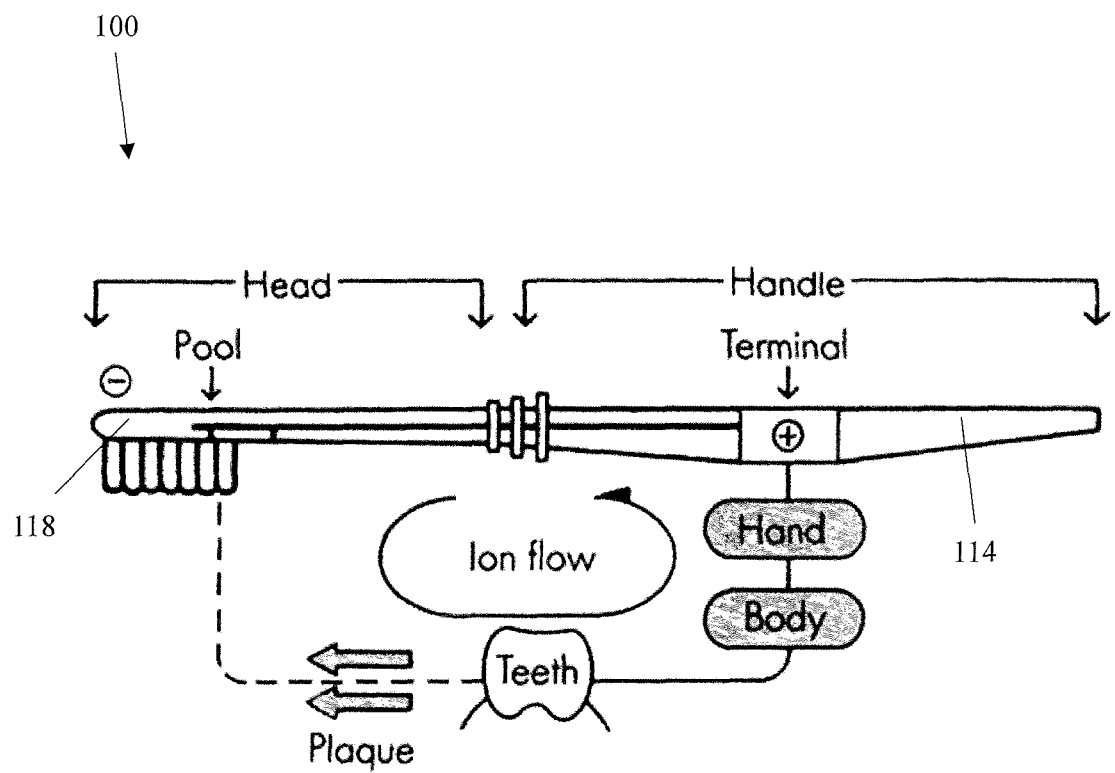
FIG. 79 is a schematic view of a toothbrush according to one embodiment wherein the interlock sensor is a current loop sensor with a cathode provided in the handle and an anode provided in the brush head for ionic therapy.

Ionic therapy using the signal loop equipped toothbrush may be implemented by providing the negatively charged anode in the brush head and the positively charged cathode in the brush handle, as seen in FIG. 79. Using a DC current with the signal loop sensor, the potential difference between the anode and cathode may be between about 1 volt and about 10 volts. In one embodiment, the potential difference is about 3 volts. Higher therapeutic currents may be achieved by ensuring the signal loop has low internal resistance compared to the resistance of the human body.

Figure 80A:
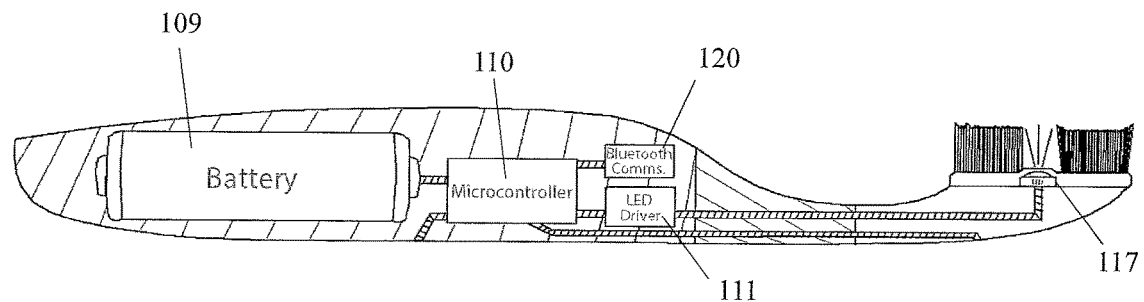
FIG. 80A is a schematic view of a toothbrush according to another embodiment wherein the toothbrush includes a communication module.

As seen in FIG. 80A, embodiments of toothbrush 100 may include a communication system 120 for sending and receiving signals to another device. For instance, communication system 120 may be a near-field communication module or Bluetooth® communication module used for pairing with a computing device. One suitable example of a Bluetooth® communication module compatible with toothbrush 100 is Bluetooth® V4.1 Smart (Low Energy) Single Mode Module sold by TDK as SESUB-PAN-D14580. Non-limiting examples of computing devices that toothbrush 100 may pair with include desktops, laptops, tablets or smartphones.

A software application may be installed on one or more computing devices to interact with toothbrush 100. The software may operate in the toothbrush, the paired device, or a further remote computer, or the software operation distributed among more than one of them. Data sent from toothbrush 100 may include its battery power levels, the current default settings, the microcontroller software version, and details of the user's brushing and light therapy events, such as start and end times and radiant power output levels. The data can be captured through the current signal loop or other eye protection sensor and recorded in a memory bank for later use. The toothbrush 100 may include a 24-hour clock for monitoring brushing and light therapy events. One example of a microcontroller with a clock suitable for inclusion in toothbrush 100 is Renasys RL78/12. The clock can be calibrated using the software application.

Using the software application, the computing device may also send data to toothbrush 100. For example, the software application may enable a user to select various preference settings and modify various features of the toothbrush, including modifying the power levels for the light source and motor, modifying the intensity of ionic potential, defining a fingerprint for an authorized user to be verified with a fingerprint sensor, modifying the ramp-up/ramp-down sequence, selecting a particular light and ionic therapy to be applied while brushing, or updating the onboard programming of the toothbrush. The selected preferences can then be uploaded to toothbrush 100 from the computing device. The computing device may also provide an identification key once it is paired with toothbrush 100 to ensure that neither is incorrectly paired with another toothbrush or computing device. For embodiments of toothbrush 100 incorporating a fingerprint security feature, the software application may provide security matching of the fingerprint ID to unlock the toothbrush.

The software application may also be used to monitor the brushing habits and progress of a prescribed therapy. In some embodiments, the software application may begin monitoring brushing habits and therapy progress once the toothbrush 100 detects that the brush head 118 is in the mouth using a current loop sensor or other interlock sensor described above. For instance, a user may be prescribed a specific light or ionic therapy by a dentist or physician. The software application is typically programmed to monitor the user's brushing habits and therapy progress each time the user inserts the brush head into his/her mouth.

The software application may include features that provide information regarding the user's brushing and therapy habits. Examples of information provided include the duration of light therapy sessions, radiant power output, the number of light therapy sessions per day, the duration of brushing sessions, the number of brushes per day, the wear state of the brush head (i.e., the percentage of maximum use), comparisons between the user's brush use and the recommendations of the American Dental Association (ADA) or other recommender, comparisons of brush use to consumer averages, and when to replace the brush head (e.g., after a predefined number of minutes of use or number of brushings). The data can be presented in raw form or as averages or other statistical measures.

Figure 87:
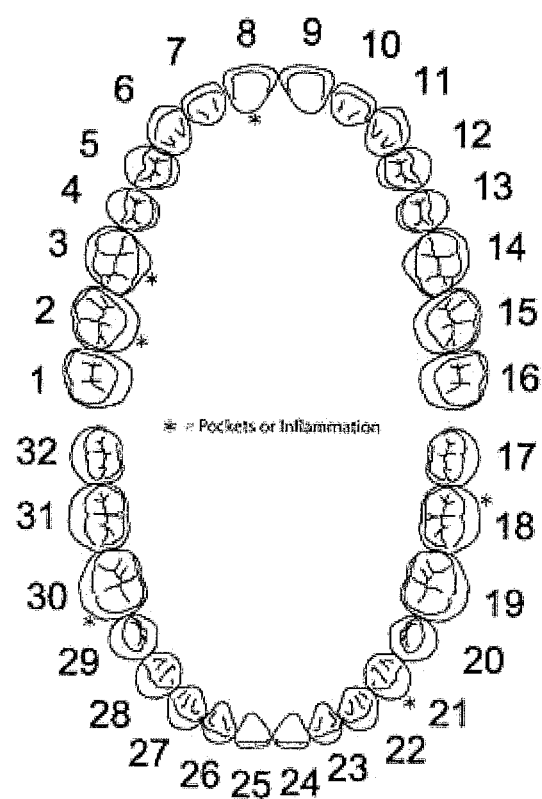
FIG. 87 is an example of a dentist's universal teeth numbering system chart.

The data may also be shared with others, such as a friend, parent, dentist or overseeing physician. Data shared by a patient to a dentist or physician may include progress of a prescribed light and ionic therapy. In one embodiment, the data may be sent via an email or text message. In another embodiment, shared data may be received from a software application. Users may also share their data via social media. Still, other means of application data sharing can be used in alternative embodiments. An overseeing dentist can highlight gum inflammation or gum pockets affecting certain teeth at the front side or back of the tooth using the dentist's universal teeth numbering system chart (see FIG. 87) and feed that data directly into the smart phone application or a cloud based application that is synchronized with the smart phone application. The dentist can then prescribe a recommended daily amount of light therapy in specific locations of the mouth using this application so that the patient can self-monitor their progress or share the therapeutic data with their physician through a data synchronized application. Software can be configured to monitor toothbrush position and inclination using sensors to monitor position and orientation such as accelerometers, IR temperature sensors, as taught in patents (e.g. WO 2002083257, US20120246858, WO 2014202250) so that the duration and intensity of light therapy applied to each of the afflicted gum pocket areas can be calculated from sensor data and compared to dentist prescribed therapy.

By sharing data with the software application, the overseeing dentist or physician can adjust and monitor the application of a prescribed therapy. For instance, the number of volts of potential difference can be adjusted by the therapist for a prescribed ionic therapy. The number of minutes of therapy as well as the number of Joules and watts of current can be monitored over time and adjusted as necessary.

The software application may also alert the user and overseeing health practitioner when a prescribed therapy is not being followed. For instance, the health prescriber could select the minimum number of Joules of light energy per day or a number of minutes at prescribed strength and wavelength per day and the application would alert if this benchmark is not met.

The software application may also provide incentives for users to establish proper brushing or light therapy habits. In one embodiment, the software application may include a system for rewarding users. For instance, the system may comprise an in-application currency that may be redeemed for rewards based on brushing habits. By way of example, a user's parent may give permission for the user to play a video game or watch a favorite TV show if the user accumulates a certain number of points that are earned over a number of brushing periods.

In some scenarios, the toothbrush and computing device may not be in range with each other and therefore cannot exchange data. Embodiments of the toothbrush can store collected data into the memory of microcontroller 110 until it is within range of a paired computing device to exchange data. When the toothbrush and computing device are in range during use, data may be actively exchanged while brushing.

The toothbrush and software application may further connect with and other accessories using communication system 120. For instance, the software application may monitor data collected from accessory sensor systems such as other oral biometric sensor devices. Examples include detecting: volatile sulfur compounds (VSC) in a person's breath which are associated with bad breath and halitosis; the presence of an active gum infection or other oral infection; changes in the oral flora with respect to caries progression focused on detection of bacterial pathogens, measurements of salivary and dental plaque pH, salivary buffering capacity and flow rate, among other parameters; monitoring the dynamics of periodontal disease, such as differentiating between progressive versus arrested states, responses to treatment, or monitoring of the presence of specific bacteria; detecting and monitoring of premalignant lesions; detecting viruses in the oral mucosa; and monitoring tooth enamel demineralization/remineralization. A prescribed therapy may be added or modified based on the results gathered from accessory sensor systems.

In another embodiment of the software application, the whiteness of the user's teeth can be measured and calculated algorithmically compared to a standard teeth whitening chart using color-adjusted photographs (for example, taken through a smart phone app). When the photograph also contains color calibration cards that can be recognized by the software through distinctive iconography, the accuracy of the teeth shade calculations is significantly improved. This may also be monitored and reported through the software application and may be shared with an overseeing therapist, such as a cosmetic dentist.

Figure 80B:
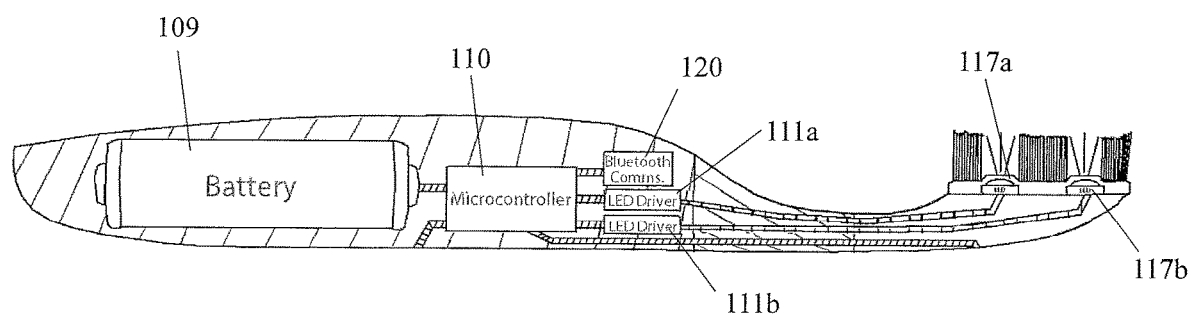
FIG. 80B is a schematic view of a toothbrush according to another embodiment wherein the toothbrush includes a first light source and a second light source.

FIG. 80B shows an embodiment wherein toothbrush 100 may include a first light source 117a and a second light source 117b. First light source 117a may comprise a blue and/or violet light having a wavelength in the range of between about 400 nm and about 500 nm, "isible therapeutic light." Second light source 117b may comprise a red light having a wavelength in the range of between about 600 nm and about 1000 nm, referred to herein as "infrared therapeutic light." Each light source is connected to its respective LED driver 111, which is connected to microcontroller 110.

During brushing, first light source 117a and second light source 117b may emit light simultaneously. In another embodiment, toothbrush 100 may include a single light source 117 incorporating two or more wavelengths or between about 400 nm to about 500 nm and about 600 nm to about 1000 nm, i.e. both visible therapeutic light and infrared therapeutic light. Toothbrush 100 may further include a Bluetooth® communications module 120 for modifying the light intensity, wavelength and other settings as described above.

Figure 81:
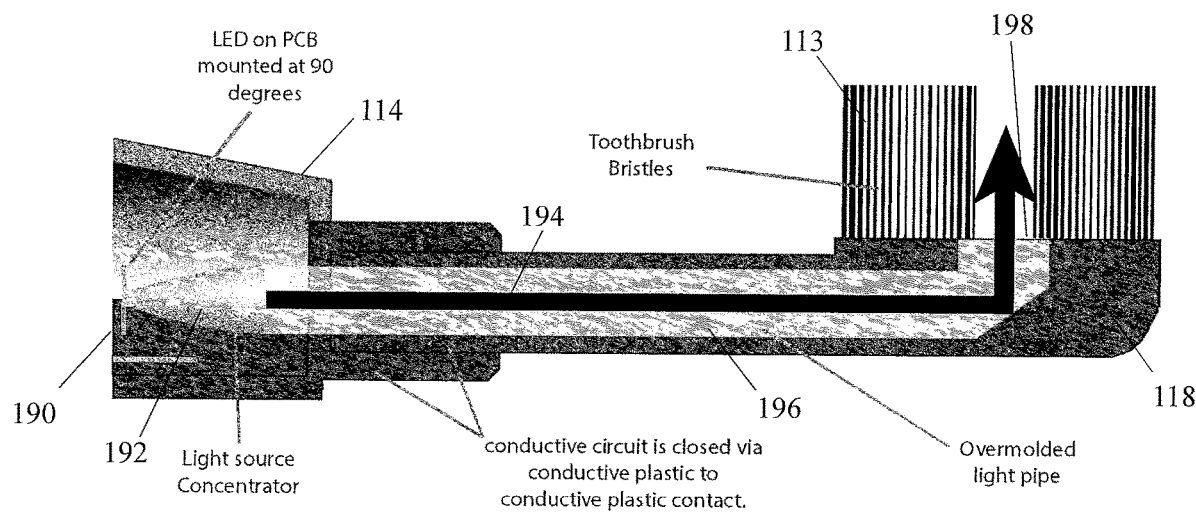
FIG. 81 is an enlarged schematic view of a toothbrush according to another embodiment wherein the light source is installed on the handle of the toothbrush.

FIG. 81 illustrates another embodiment wherein the light source is installed on the handle of toothbrush 100. In the embodiment shown, light source 190 is installed in the handle 114. Brush head 118 is a separate piece having a light pipe 196 that aligns with source 190 to carry light through an aperture 198 adjacent to bristles 113. Brush head 118 may be detachable from the handle 114 using a bayonet mount. Other mounting connections can be used such as male/female press fits, with either the handle or the neck of the distal end having the female fitting and the other having the male fitting.

Light pipe 196 may be housed in a non-conductive plastic sheath. A light source concentrator 192 is installed with light source 190 that increases the intensity of the emitted light 194 from light source 190. Preferably, both the light source concentrator 192 and light pipe 196 should be less than about 8 mm in diameter to remain comfortable for the user to use.

In some embodiments, the light source concentrator 192 comprises a parabolic concentrator that uses total internal reflection to direct emitted light 194 along light pipe 196 to aperture 198. In operation, the parabolic concentrator takes the form of a shifted and tilted parabola of revolution in accordance with the edge ray principle. One example of a suitable shape for a light source concentrator would be Part Number 10356 from Carclo Optics, with its size modified to be installed onto the handle 114 of toothbrush 100.

Figure 82:
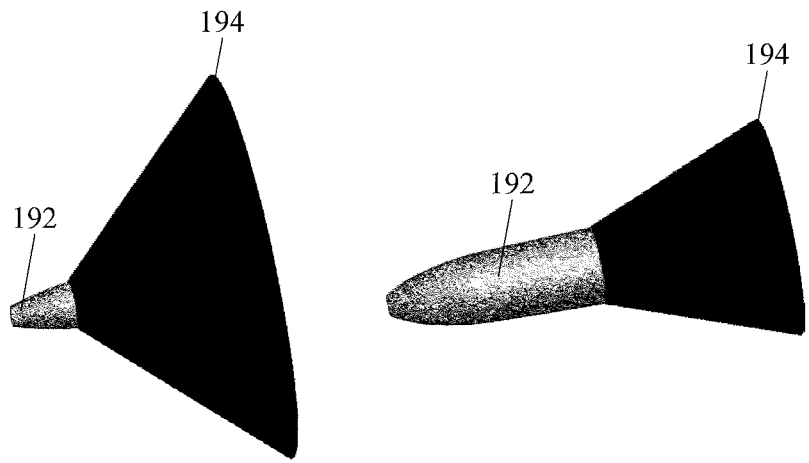
FIG. 82 is a table with an accompanied schematic of a light source concentrator disclosing how the angle of incidence varies with the size of the light source concentrator.

Preferably, the total internal reflection of the surface should have an efficiency of greater than about 80% to minimize transmission losses. Transmission losses may be minimized by keeping the angle of incidence (i.e., the angle at which the emitted light 194 enters light pipe 196) within a range where total internal reflection is achieved. This may be accomplished by selecting the proper sizing for the light source concentrator. In one embodiment, the toothbrush may include a 1 mm LED with a light source concentrator 192 and a light pipe 196 having a shared diameter of 4.4 mm. As seen in FIG. 82, the angle of incidence is a function of the ratio between the input diameter and output diameter and length of the light source concentrator.

Other mechanisms may be used to transmit emitted light 194 through light pipe 196. For example, light pipe 196 may comprise a mirrored or other curved surface to facilitate guiding emitted light 194 to aperture 198. Other beam-steering components, such as lenses, diffractive optics and prisms, may be installed in the brush head 118 to further control how emitted light 194 is distributed through the light pipe 196 and aperture 198.

Figure 83:
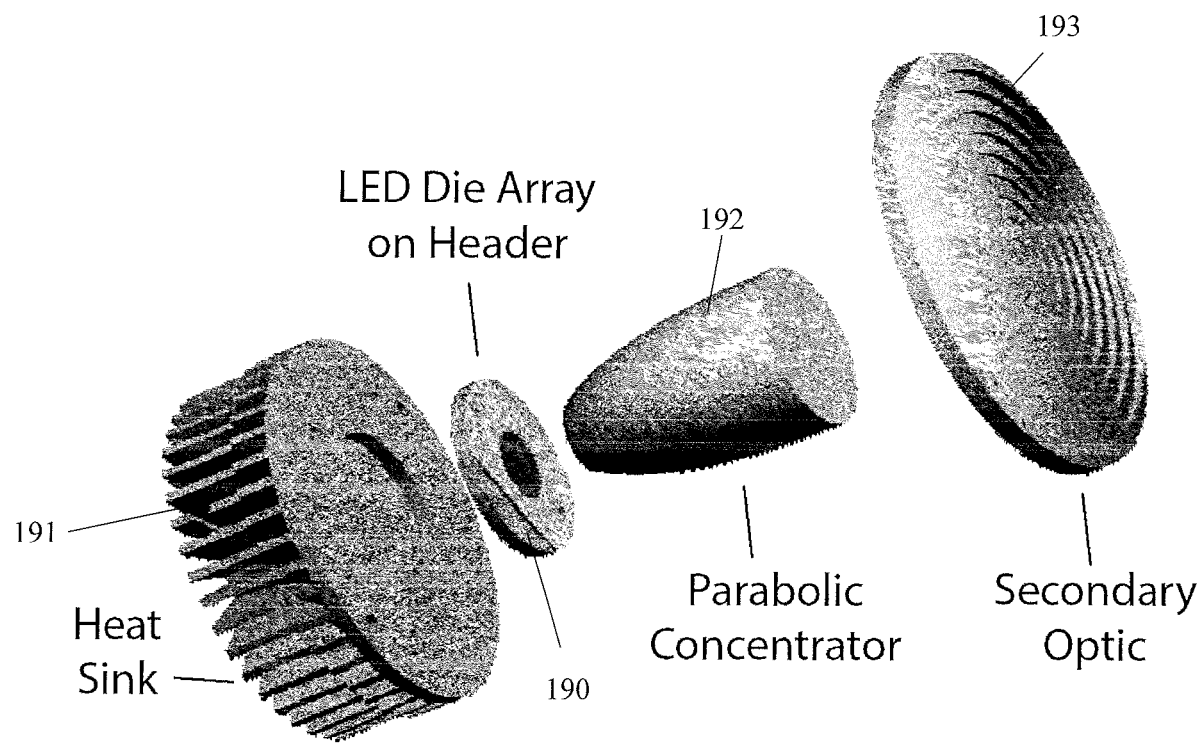
FIG. 83 is an exploded view of the light assembly in FIG. 81.

FIG. 83 shows an enlarged, exploded view of various components for the light assembly in FIG. 81. The light assembly includes light source 190 attached to a heat sink 191 to dissipate heat and a light source concentrator attached to the other end of light source 190. In the embodiment shown, light source 190 comprises an array of LEDs on a PCB board and light source concentrator 192 comprises a parabolic concentrator. A secondary optic 193 may be used to further steer emitted light. In other embodiments, light source 190 may comprise a laser diode instead of a light-emitting diode. For example, light source 190 may be a vertical-cavity surface-emitting laser (VCSEL). The VCSEL may be used as a potential source for emitting red and/or infrared light, "infrared therapeutic light." If an unfocused laser diode is used, the light source concentrator will likely not be required due to the inherently narrower beam concentration of laser diodes.

Figure 84:
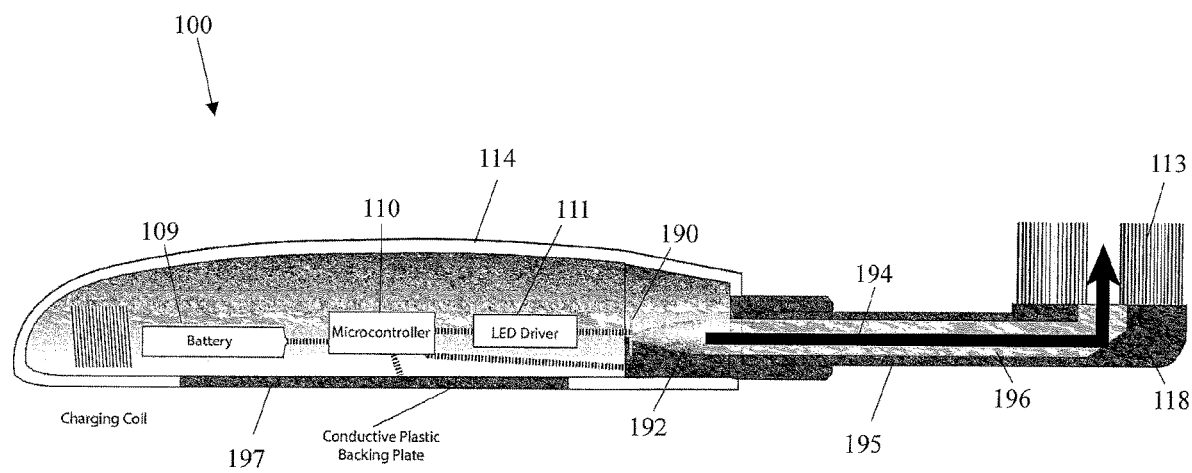
FIG. 84 is a schematic view of a toothbrush having a conductive plastic backing plate on the handle and a brush head comprising a conductive plastic with a light source installed on its handle.

FIG. 84 shows an embodiment of toothbrush 100 wherein light pipe 196 is encased in electrically conductive plastic 195 (e.g., a carbon-based plastic). Light source 190 is connected to LED driver 111, and LED driver 111 is connected to microcontroller 110 for regulating the functions of the light source. Microcontroller 110 is connected to the battery 109, the conductive plastic backing plate 197 on handle 114, and to the conductive plastic 195 forming the brush head 118 to form an electrical circuit when the user holds the handle 114 and the brush head 118 is placed in the mouth of the user. This condition is detected through the current signal loop to enable the therapeutic light.

Figure 85:
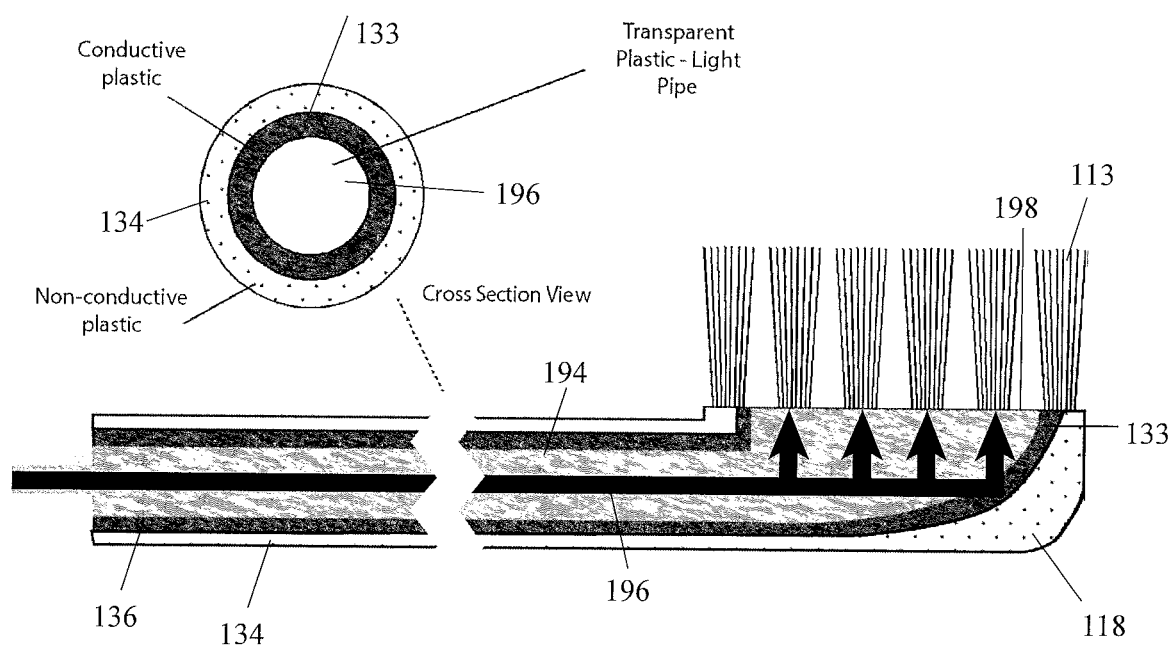
FIG. 85 is an enlarged schematic view of another embodiment wherein a light pipe is encased in conductive plastic and surrounded by a non-conductive plastic layer forming brush head.

An enlarged and cross-sectional view of another embodiment of brush head 118 is shown in FIG. 84. This brush head and the brush head shown in FIG. 85 are used with a handle like the handle shown in FIG. 83. Light pipe 196 is encased in conductive plastic 133 and surrounded by a non-conductive plastic layer 134 forming brush head 118. Conductive plastic 133 is exposed at the distal end of brush head 118 at aperture 198. As the user grabs the handle 114 and inserts the brush head 118 into the mouth, an electrical circuit is completed by the connection of the mouth in contact with plastic 133 that is also connected to the circuit in the handle (not shown), and the light source 190 is activated.

Figure 86:
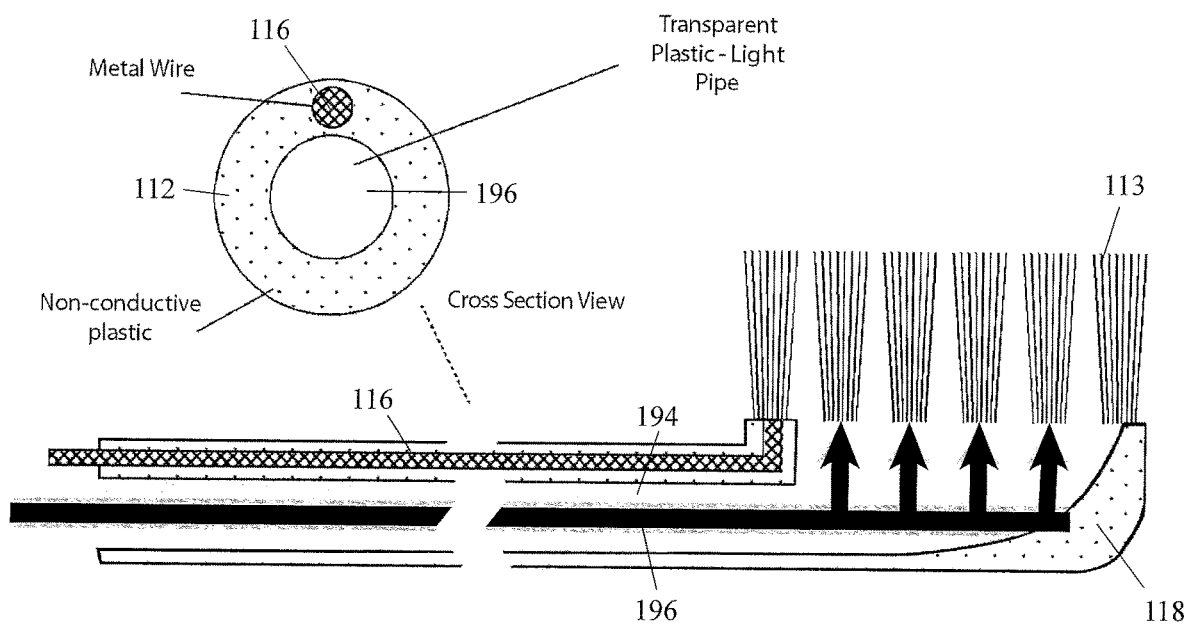
FIG. 86 is an enlarged schematic view of another embodiment wherein a light pipe is encased in non-conductive plastic and the toothbrush includes a metal wire for use as part of a sensor.

Another embodiment of brush head 118 is shown in FIG. 86, wherein the microcontroller 110 of FIG. 84 is connected to an embedded metal wire 116 that is exposed at the distal end of brush head 118 and on the surface of the handle 114. Light pipe 196 is encased in non-conductive plastic 112. An electrical circuit is formed when the user grabs the handle 114 and inserts bristles 113 into the mouth, wherein metal wire 116 comes into contact with the user's mouth and hand to establish the electrical circuit to the microcontroller 110.

Installing the light source 190 in the handle 114 provides several benefits. For instance, the light source 190 may be driven at greater power levels when installed at the handle 114 since there is no source of heat in the user's mouth. It also enables smaller and more compact designs, and allows the manufacturer to further modify the light distribution at aperture 198 using various secondary optics 193. The sizing of aperture 198 as well as the light intensity of emitted light 194 may also be modified; for example, the aperture may be sized larger than a standard LED diode. Having a larger aperture enables the emitted light to cover a greater surface area of the user's mouth while brushing. In one embodiment, aperture 198 covers between about 10% to about 50% of the surface area of brush head 118.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. A light emitting oral care instrument comprising:
a battery or compartment for a battery and a light source that produces a wavelength in the range of 400 nm to 500 nm,
electronics coupled to the battery or compartment for a battery and the light source to supply electricity from the battery or compartment for a battery to the source at current and voltage that causes the light source to emit light, the instrument including a handle and a distal end; the electronics configured to provide a ramp-up sequence to gradually modify the power of the light source before it reaches full power, at least a portion of the instrument being equipped with one or more sensors coupled to the electronics to determine whether the distal end is inside or outside of the mouth and the electronics ramps up power to the source of light when the electronics determine that the distal end of the instrument is in the mouth.

2. The instrument as claimed in claim 1 further including an alarm adapted to warn a user of a power status of the source of light before it reaches full power.

3. The instrument as claimed in claim 2, wherein the alarm incorporates a gradual color change of the therapeutic light from a first color to at least a second color.

4. The instrument as claimed in claim 2, wherein the alarm is a vibrator coupled with a light emitter to warn the user of the power status of the source of light.

5. The instrument as claimed in claim 4, wherein the vibrator operates by providing a series of pulsed vibration for a period of between about 0.5 seconds to about 5 seconds before the source of light reaches full power.

6. The instrument as claimed in claim 4, wherein the vibrator is a motor used to drive the bristles on the distal end of the brush.

7. The instrument as claimed in claim 2, wherein the alarm is an auditory device emitting a sound to warn the user of the power status of the source of light.

8. The instrument as claimed in claim 1, wherein the sensor or combination of sensors is selected from a group consisting of: a current signal loop whereby the user who uses the toothbrush to brush his or her teeth by grasping the handle and inserting the bristles into his or her mouth closes the open circuit to complete a signal loop and removal of the distal end from the mouth opens the circuit to break the signal loop, turning off the source of light; a capacitive sensor which detects current flowing through the body of a user when the brush head or bristles are in contact with the mouth and the handle is in contact with the hand; a capacitive displacement sensor that senses change of position of any conductive target such as the human body; an inductive sensor that uses an inductance loop to measure the proximity of conductors such as the human body; a passive thermal infrared that detects the warmth of the human mouth; a photoelectric sensor that detects reflected IR light emitted and absorbed by the sensor itself; a light sensor that is triggered by darkness inside the mouth; a light sensor that detects the reflection of light from a second light source on the brush when the brush is activated; an ultrasonic and active sonar sensors that uses echo location to detect the confines of the mouth; a magnetic detector that detects the proximity of metals such as the hemoglobin present in blood; a pressure sensor under the brush head that detects movement and pressure of the brush head being pressed against the teeth; a pressure sensor in the neck that detects torque and tension in the neck of the brush due to brushing action; a moisture sensor to detect a highly moist environment such as the mouth; and a combination of two or more of these sensor types.

9. The instrument as claimed in claim 1 further including a fingerprint sensor is mounted on the handle to verify if the user is authorized.

10. The instrument as claimed in claim 1 further including a secondary red or infrared therapeutic light source with a wavelength in the range of 600 nm to 1000 nm also having a ramp-up sequence.

11. The instrument as claimed in claim 1, wherein the control circuit has a ramp-down sequence that begins when the sensor switches from the closed state to the open state and returns to the therapeutic light on full state when the sensor switches from the open state to the closed state during the ramp-down sequence.

12. The instrument as claimed in claim 11, wherein the control circuit supplies power to the source of light at less than 100% for the duration of the ramp-down when the closed circuit becomes open.

13. The instrument as claimed in claim 12, wherein the control circuit supplies between about 10% to about 50% power to the light source for a transition period of between about 0.1 to about 1 second during the ramp-down sequence.

14. A light emitting oral care instrument comprising:
a battery or compartment for a battery and a therapeutic light source that produces a wavelength in the range of 400 nm to 500 nm, electronics coupled to the battery or the compartment for a battery and source of light to supply electricity from the battery or the compartment for a battery to the source at current and voltage that causes the light source to emit light, the instrument including a handle and a distal end;
at least a portion of the instrument being equipped with electronics wherein the electronics generates and stores data about light therapy events and is wirelessly connected to an external computing device to store data about the light therapy events.

15. The instrument as claimed in claim 14, wherein the instrument includes a handle and a distal end;
at least a portion of the instrument being equipped with one or more sensors coupled to the electronics to determine whether the distal end is inside or outside of the mouth and the electronics ramps up power to the source of light when the electronics determine that the distal end of the instrument is in the mouth; and
wherein the electronics provides a short burst of low frequency light pulses or flashes of the therapeutic light for a period of at least 0.5 seconds.

16. The instrument as claimed in claim 14, wherein the instrument includes a handle and a distal end;
at least a portion of the instrument being equipped with one or more sensors coupled to the electronics to determine whether the distal end is inside or outside of the mouth and the electronics ramps up power to the source of light when the electronics determine that the distal end of the instrument is in the mouth; and
wherein the electronics gradually increases intensity of the therapeutic light over a period of at least 0.5 seconds.

17. The instrument as claimed in claim 14, wherein the toothbrush is a manual toothbrush or motorized power toothbrush.

18. The instrument as claimed in claim 14, wherein the instrument includes a handle and a distal end;
wherein the light source is located in the handle of the toothbrush and directs light through a light pipe on the distal end and emitting light out of an aperture in the distal end.

19. The instrument as claimed in claim 14, wherein the instrument includes a handle and a distal end;
wherein the light source is located in the distal end.

20. The instrument as claimed in claim 14, wherein the therapeutic data captured comprises start and end times, duration of light therapy, and radiant power output levels.

21. The instrument as claimed in claim 14, wherein the instrument is equipped with software to monitor toothbrush position and inclination using sensors to monitor position and orientation so that the duration and intensity of light therapy applied to each of the afflicted gum pocket areas can be calculated from sensor data.

22. The instrument as claimed in claim 14, wherein the light therapy data is uploaded into a cloud-based databank for access by an application available to the end user or supervising medical practitioner or sharing on other platforms such as e-mail or social media.

23. The instrument as claimed in claim 14, wherein the external computing device is selected from the group consisting of a tablet, desktop, laptop, tablet and smartphone.

24. The instrument as claimed in claim 14, wherein the external computing device can be used to wirelessly control the therapeutic light intensity and wavelength.

25. The instrument as claimed in claim 14 further including a secondary emitter with a wavelength in the range of 600 nm to 1000 nm.

26. The instrument as claimed in claim 14, wherein the one or more sensors is selected from a group consisting of: a current signal loop whereby the user who uses the toothbrush to brush his or her teeth by grasping the handle and inserting the bristles into his or her mouth closes the open circuit to complete a signal loop and removal of the distal end from the mouth opens the circuit to break the signal loop, turning off the source of light; a capacitive sensor which detects current flowing through the body of a user when the brush head or bristles are in contact with the mouth and the handle is in contact with the hand; a capacitive displacement sensor that senses change of position of any conductive target such as the human body; an inductive sensor that uses an inductance loop to measure the proximity of conductors such as the human body; a passive thermal infrared that detects the warmth of the human mouth; a photoelectric sensor that detects reflected IR light emitted and absorbed by the sensor itself; a light sensor that is triggered by darkness inside the mouth; a light sensor that detects the reflection of light from a second light source on the brush when the brush is activated; an ultrasonic and active sonar sensors that uses echo location to detect the confines of the mouth; a magnetic detector that detects the proximity of metals such as the hemoglobin present in blood; a pressure sensor under the brush head that detects movement and pressure of the brush head being pressed against the teeth; a pressure sensor in the neck that detects torque and tension in the neck of the brush due to brushing action; a moisture sensor to detect a highly moist environment such as the mouth; and a combination of two or more of these sensor types.

27. The instrument as claimed in claim 14, wherein the instrument is selected from the group consisting of a toothbrush, flosser or water based flosser.

28. The instrument as claimed in claim 14, wherein the instrument is equipped with one or more sensors used to determine whenever the distal end is outside the environment of the mouth.

* * * * *